United States Patent
Furlan Freguia et al.

(10) Patent No.: US 12,318,434 B2
(45) Date of Patent: Jun. 3, 2025

(54) ALKALINE PHOSPHATE-BASED ONCOLOGY TREATMENTS

(71) Applicant: Theriva Biologics, Inc., Rockville, MD (US)

(72) Inventors: Christian Furlan Freguia, Rockville, MD (US); Michael Kaleko, Rockville, MD (US)

(73) Assignee: Theriva Biologics, Inc., Rockville, MD (US)

( * ) Notice: Subject to any disclaimer, the term of this patent is extended or adjusted under 35 U.S.C. 154(b) by 679 days.

(21) Appl. No.: 17/608,252

(22) PCT Filed: May 5, 2020

(86) PCT No.: PCT/US2020/031430
§ 371 (c)(1),
(2) Date: Nov. 2, 2021

(87) PCT Pub. No.: WO2020/227263
PCT Pub. Date: Nov. 12, 2020

(65) Prior Publication Data
US 2022/0202914 A1    Jun. 30, 2022

Related U.S. Application Data

(60) Provisional application No. 62/843,850, filed on May 6, 2019.

(51) Int. Cl.
*A61K 38/46* (2006.01)
*A61K 31/513* (2006.01)
*A61P 35/00* (2006.01)

(52) U.S. Cl.
CPC .......... *A61K 38/465* (2013.01); *A61K 31/513* (2013.01); *A61P 35/00* (2018.01); *C12Y 301/03001* (2013.01)

(58) Field of Classification Search
None
See application file for complete search history.

(56) References Cited

U.S. PATENT DOCUMENTS

| | | |
|---|---|---|
| 5,773,226 A | 6/1998 | Millan |
| 5,821,095 A | 10/1998 | Hattori et al. |
| 5,891,699 A | 4/1999 | Boulain et al. |
| 5,948,410 A | 9/1999 | Van Scharrenburg et al. |
| 6,183,784 B1 | 2/2001 | Read et al. |
| 6,290,952 B1 | 9/2001 | Poelstra et al. |
| 6,406,899 B1 | 6/2002 | Hoelke et al. |
| 6,638,531 B1 | 10/2003 | Amerongen et al. |
| 6,649,390 B1 | 11/2003 | Sheng et al. |
| 6,686,392 B1 | 2/2004 | Avram et al. |
| 6,756,063 B2 | 6/2004 | Kiss |
| 6,793,928 B1 | 9/2004 | Van Scharrenburg et al. |
| 6,884,602 B2 | 4/2005 | Mueller et al. |
| 6,905,689 B2 | 6/2005 | Schneidinger et al. |
| 7,011,965 B2 | 3/2006 | Kiss |
| 7,014,852 B2 | 3/2006 | Kiss |
| 7,048,914 B2 | 5/2006 | Kiss |
| 7,060,677 B1 | 6/2006 | Van Berkel et al. |
| 7,312,198 B2 | 12/2007 | Kiss |
| 7,374,754 B2 | 5/2008 | Kiss |
| 7,423,029 B1 | 9/2008 | Kiss |
| 7,501,116 B2 | 3/2009 | Kiss |
| 7,557,081 B2 | 7/2009 | Kiss |
| 7,589,083 B2 | 9/2009 | Kiss |
| 7,655,620 B2 | 2/2010 | Kiss |
| 7,695,714 B2 | 4/2010 | Kiss |
| 7,718,170 B2 | 5/2010 | Kiss |
| 7,763,712 B2 | 7/2010 | Crine et al. |
| 7,781,423 B2 | 8/2010 | Kiss |
| 7,786,082 B2 | 8/2010 | Kiss |
| 7,790,685 B2 | 9/2010 | Kiss |
| 7,858,085 B2 | 12/2010 | Kiss |
| 7,943,126 B2 | 5/2011 | Tomatsu et al. |
| 7,943,606 B2 | 5/2011 | Kiss |
| 7,960,529 B2 | 6/2011 | Crine et al. |
| 7,964,188 B2 | 6/2011 | Kiss |
| 8,372,638 B2 | 2/2013 | Kiss |
| 8,460,654 B2 | 6/2013 | Kiss |
| 8,557,545 B2 | 10/2013 | Velders et al. |
| 8,574,863 B2 | 11/2013 | Brands et al. |
| 8,586,032 B2 | 11/2013 | Pickkers et al. |
| 8,603,464 B2 | 12/2013 | Kiss |
| 8,647,854 B2 | 2/2014 | Lee et al. |

(Continued)

FOREIGN PATENT DOCUMENTS

| | | |
|---|---|---|
| EP | 1952823 A1 | 8/2008 |
| EP | 1759001 B1 | 4/2011 |

(Continued)

OTHER PUBLICATIONS

International Search Report & Written Opinion PCT Application No. PCT/US2020/31430, dated Aug. 27, 2020, 12 pages.

Furlan Freguia et al., "Oral intestinal alkaline phosphatase improves efficacy of 5-FU in a colorectal cancer mouse model," Oct. 1, 2019 (Oct. 1, 2019), XP093008225, DOI: doi.org/10.1093/annonc/mdz268.008.

Bajin-Katić et al., "Intestinal alkaline phosphatase activity as a molecular marker of enterotoxicity induced by single dose of 5-fluorouracil and protective role of orally administered glutamine," Archive of Oncology (2006).

Alshahrani, et al., "Stability-enhanced Hot-melt Extruded Amorphous Solid Dispersions via Combinations of Soluplus® and HPMCAS-HF," American Association of Pharmaceutical Scientists, vol. 16, No. 4, pp. 824-834, Aug. 2015.

(Continued)

*Primary Examiner* — Blaine Lankford
(74) *Attorney, Agent, or Firm* — Morgan, Lewis & Bockius LLP

(57) ABSTRACT

The present invention relates to methods and compositions for preventing, treating, or reducing chemotherapy treatment-mediated side effects, including gastrointestinal (GI) side effects, comprising administering to a subject intestinal alkaline phosphatases (IAP).

13 Claims, 5 Drawing Sheets

Specification includes a Sequence Listing.

(56) References Cited

U.S. PATENT DOCUMENTS

| | | | |
|---|---|---|---|
| 8,691,208 B2 | 4/2014 | Tomatsu et al. | |
| 8,735,087 B2 | 5/2014 | Brands et al. | |
| 8,778,674 B2 | 7/2014 | Kiss | |
| 8,784,805 B2 * | 7/2014 | Brands | C12Y 301/03001 |
| | | | 424/94.1 |
| 8,784,833 B2 | 7/2014 | Sly et al. | |
| 8,932,587 B2 | 1/2015 | Hodin et al. | |
| 9,133,446 B2 | 9/2015 | Aiba et al. | |
| 9,631,185 B2 | 4/2017 | Schyns et al. | |
| 9,926,544 B2 | 3/2018 | Raaben et al. | |
| 9,976,129 B2 | 5/2018 | Kamiya et al. | |
| 9,988,620 B2 | 6/2018 | Crine et al. | |
| 10,000,532 B2 | 6/2018 | Crine et al. | |
| 10,052,366 B2 | 8/2018 | Crine et al. | |
| 10,449,236 B2 | 10/2019 | Marozsan et al. | |
| 10,570,380 B2 | 2/2020 | Jonk et al. | |
| 10,603,361 B2 | 3/2020 | Odrijin | |
| 2004/0091530 A1 | 5/2004 | Ende et al. | |
| 2007/0148155 A1 | 6/2007 | Kiss | |
| 2007/0280922 A1 | 12/2007 | Kiss | |
| 2009/0136600 A1 | 5/2009 | Wu | |
| 2010/0158888 A1 | 6/2010 | Kiss | |
| 2010/0221234 A1 | 9/2010 | Crine et al. | |
| 2010/0297119 A1 | 11/2010 | Crine et al. | |
| 2011/0052560 A1 | 3/2011 | Brands | |
| 2011/0206654 A1 | 8/2011 | Hodin et al. | |
| 2012/0308526 A1 | 12/2012 | Ohtake et al. | |
| 2013/0045192 A1 | 2/2013 | Movalia et al. | |
| 2013/0108635 A1 | 5/2013 | Crine et al. | |
| 2013/0251701 A1 | 9/2013 | Kiss | |
| 2013/0280232 A1 | 10/2013 | Brands et al. | |
| 2013/0323244 A1 | 12/2013 | Crine et al. | |
| 2015/0216813 A1 | 8/2015 | Everett et al. | |
| 2017/0252327 A1 | 9/2017 | Hodin et al. | |

FOREIGN PATENT DOCUMENTS

| | | |
|---|---|---|
| EP | 2158319 B1 | 7/2011 |
| EP | 2368999 B1 | 3/2014 |
| EP | 2662448 B1 | 12/2016 |
| JP | 2017192381 | 10/2017 |
| WO | WO 1999/026654 A1 | 6/1999 |
| WO | WO 1999/033955 A1 | 7/1999 |
| WO | WO 1999/037678 A2 | 7/1999 |
| WO | WO 2000/032629 A2 | 6/2000 |
| WO | WO 2001/034641 A2 | 5/2001 |
| WO | WO 2001/056627 A1 | 8/2001 |
| WO | WO 2002/060503 A1 | 8/2002 |
| WO | WO 2004/054609 A1 | 7/2004 |
| WO | WO 2004/112494 A2 | 12/2004 |
| WO | WO 2005/055956 A2 | 6/2005 |
| WO | WO 2005/074978 A1 | 8/2005 |
| WO | WO 2005/103263 A1 | 11/2005 |
| WO | WO 2007/055760 A2 | 5/2007 |
| WO | WO 2007/081654 A2 | 7/2007 |
| WO | WO 2008/024103 A1 | 2/2008 |
| WO | WO 2008/094037 A1 | 8/2008 |
| WO | WO 2008/104199 A1 | 9/2008 |
| WO | WO 2008/104200 A1 | 9/2008 |
| WO | WO 2008/133511 A2 | 11/2008 |
| WO | WO 2008/138131 A1 | 11/2008 |
| WO | WO 2009/028943 A1 | 3/2009 |
| WO | WO 2009/106368 A1 | 9/2009 |
| WO | WO 2010/025267 A2 | 3/2010 |
| WO | WO 2010/151526 A1 | 12/2010 |
| WO | WO 2011/057250 A1 | 5/2011 |
| WO | WO 2011/134084 A1 | 11/2011 |
| WO | WO 2012/054057 A1 | 4/2012 |
| WO | WO 2012/169892 A2 | 12/2012 |
| WO | WO 2012/171077 A1 | 12/2012 |
| WO | WO 2012/177100 A2 | 12/2012 |
| WO | WO 2013/058833 A1 | 4/2013 |
| WO | WO 2013/059491 A1 | 4/2013 |
| WO | WO 2015/112015 A1 | 7/2015 |
| WO | WO 2015/112017 A2 | 7/2015 |
| WO | WO 2015/166045 A2 | 11/2015 |
| WO | WO 2016/090251 A1 | 6/2016 |
| WO | WO 2016/123342 A2 | 8/2016 |
| WO | WO 2017/031114 A1 | 2/2017 |
| WO | WO 2017/058822 A1 | 4/2017 |
| WO | WO 2017/074466 A1 | 5/2017 |
| WO | WO 2017/155569 A1 | 9/2017 |
| WO | WO 2017/173395 A1 | 10/2017 |
| WO | WO 2017/173413 A1 | 10/2017 |
| WO | WO 2017/214130 A1 | 12/2017 |
| WO | WO 2018/009555 A1 | 1/2018 |
| WO | WO 2018/035420 A1 | 2/2018 |
| WO | WO 2018/127363 A1 | 7/2018 |
| WO | WO 2018/164995 A1 | 9/2018 |
| WO | WO 2018/175413 A1 | 9/2018 |
| WO | WO 2018/183720 A1 | 10/2018 |
| WO | WO 2017/203426 A1 | 2/2019 |
| WO | WO 2018/183720 A9 | 7/2019 |
| WO | WO 2019/139891 A1 | 7/2019 |
| WO | WO 2019/172766 A1 | 9/2019 |
| WO | WO 2019/183209 A1 | 9/2019 |
| WO | WO 2019/190752 A1 | 10/2019 |
| WO | WO 2019/245938 A1 | 12/2019 |
| WO | WO 2020/033867 A2 | 2/2020 |
| WO | WO 2020/227263 A1 | 11/2020 |
| WO | WO 2020/247421 A1 | 12/2020 |
| WO | WO 2021/011754 A1 | 1/2021 |

OTHER PUBLICATIONS

Beumer, et al., "Calf Intestinal Alkaline Phosphatase, A Novel Therapeutic Drug for Lipopolysaccharide (LPS)-Mediated Diseases, Attenuates LPS Toxicity in Mice and Piglets," The Journal of Pharmacology and Experimental Therapeutics, vol. 307, No. 2, pp. 737-744 (Jul. 2003).

Chen, et al., "A Role for Intestinal Alkaline Phosphatase in the Maintenance of Local Gut Community," Dig Dis Sci. Apr. 2011; 56(4): 1020-1027 (doi:10.1007/s10620-010-1396-x).

Chen, et al. "Identification of specific targets for the gut mucosal defense factor intestinal alkaline phosphatase," American Journal of Physiology, Aug. 2010, Epub May 2012, vol. 299, No. 2 pp. G467-G475.

Cui, et al., "Faecal microbiota transplantation protects against radiation-induced toxicity", EMBO Molecular Medicine vol. 9 | No. 4 | 2017, 14 pages.

Curatolo, et al., "Utility of Hydroxypropylmethylcellulose Acetate Succinate (HPMCAS) for Initiation and Maintenance of Drug Supersaturation in the GI Milieu," Pharmaceutical Research, vol. 26, No. 6, pp. 1419-1431 (Jun. 2009).

Economopoulos, et al., "Prevention of antibiotic-associated metabolic syndrome in mice by intestinal alkaline phosphatase," Diabetes, Obesity and Metabolism, vol. 18, No. 5., pp. 519-527 (May 2016).

Estaki, et al., "Interplay between intestinal alkaline phosphatase, diet, gut microbes and immunity," World Journal of Gastroenterology, 20(42), pp. 15650-15656 (Nov. 2014).

Friesen, et al., "Hydroxypropyl Methylcellulose Acetate Succinate-Based Spray-Dried Dispersions: An Overview," Molecular Pharmaceuticals, vol. 5, No. 6, pp. 1003-1019 (Dec. 2008).

Goldberg, et al., "Intestinal alkaline phosphatase is a gut mucosal defense factor maintained by enteral nutrition," PNAS, vol. 105, No. 9, pp. 3551-3556 (Mar. 2008).

Hauer-Jensen, et al., "Radiation Enteropathy—Pathogenesis, Treatment, and Prevention", Nat Rev Gastroenterol Hepatol. Aug. 2014; 11(8): 470-479. doi:10.1038/nrgastro.2014.46, 27 pages.

International Search Report & Written Opinion, PCT/US2018/023327, May 25, 2018, 12 pages.

Kaliannan, et al., "Intestinal alkaline phosphatase prevents metabolic syndrome in mice," PNAS, vol. 110, No. 17, pp. 7003-7008 (Apr. 2013).

Kühn, et al., "Intestinal alkaline phosphatase targets the gut barrier to prevent aging," JCI Insight. 2020;5(6):e134049. https://doi.org/10.1172/ici.insight.134049, 16 pages.

(56) References Cited

OTHER PUBLICATIONS

Lallès, "Intestinal alkaline phosphatase: novel functions and protective effects," Nutrition Reviews, vol. 72(2), pp. 82-94 (2014).

Liu, et al., "Intestinal Alkaline Phosphatase Regulates Tight Junction Protein Levels", J Am Coll Surg. Jun. 2016: 222(6): 1009-1017. doi:10.1016/j.jamcollsurg.2015.12.006.

Malo, et al., "Intestinal alkaline phosphatase preserves the normal homeostasis of gut microbiota," Gut 2010;59:1476-1484 (doi:10.1136/gut.2010.211706).

Parlato, et al., "Human ALPI deficiency causes inflammatory bowel disease and highlights a key mechanism of gut homeostasis," EMBO Molecular Medicine, e8483, pp. 1-12 (Mar. 2018).

Peters, et al., "The Potential of Alkaline Phosphatase as a Treatment for Sepsis-Associated Acute Kidney Injury," Nephron Clin Pract 2014; 127: pp. 144-148 (Sep. 2014).

Ramasamy, et al., "Intestinal Alkaline Phosphatase Has Beneficial Effects in Mouse Models of Chronic Colitis", Inflamm Bowel Dis. Feb. 2011; 17(2): 532-542. doi:10.1002/ibd.21377.

Rentea, et al., "Radiation-induced changes in intestinal and tissue-nonspecific alkaline phosphatase: implications for recovery after radiation therapy", The American Journal of Surgery (2016) 212, 602-608, 7 pages.

Rieder, et al., "Animal models of intestinal fibrosis: new tools for the understanding of pathogenesis and therapy of human disease", Am J Physiol Gastrointest Liver Physiol 303: G786-G801, 2012, 16 pages.

Shah, et al., "Improved Human Bioavailability of Vemurafenib, a Practically Insoluble Drug, Using an Amorphous Polymer-Stabilized Solid Dispersion Prepared by a Solvent-Controlled Coprecipitation Process," Journal of Pharmaceutical Sciences, vol. 102, No. 3, pp. 967-981 (Mar. 2013).

\* cited by examiner

SEQUENCE LISTING

<160> NUMBER OF SEQ ID NOS: 41

<210> SEQ ID NO 1
<211> LENGTH: 528
<212> TYPE: PRT
<213> ORGANISM: Artificial Sequence
<220> FEATURE:
<223> OTHER INFORMATION: Synthetic polymer.

<400> SEQUENCE: 1

```
Met Gln Gly Pro Trp Val Leu Leu Leu Gly Leu Arg Leu Gln Leu
1               5                   10                  15

Ser Leu Gly Val Ile Pro Ala Glu Glu Asn Pro Ala Phe Trp Asn
                20                  25                  30

Arg Gln Ala Ala Glu Ala Leu Asp Ala Ala Lys Lys Leu Gln Pro Ile
                35                  40                      45

Gln Lys Val Ala Lys Asn Leu Ile Leu Phe Leu Gly Asp Gly Leu Gly
        50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
                100                 105                 110

Ala Thr Ala Thr Ala Tyr Leu Cys Gly Val Lys Ala Asn Phe Gln Thr
                115                 120                 125

Ile Gly Leu Ser Ala Ala Ala Arg Phe Asn Gln Cys Asn Thr Thr Arg
        130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
                180                 185                 190

Met Pro Ala Ser Ala Arg Gln Glu Gly Cys Gln Asp Ile Ala Thr Gln
                195                 200                 205

Leu Ile Ser Asn Met Asp Ile Asp Val Ile Leu Gly Gly Gly Arg Lys
        210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
                260                 265                 270

Met Gln Ala Ser Leu Asp Gln Ser Val Thr His Leu Met Gly Leu Phe
                275                 280                 285

Glu Pro Gly Asp Thr Lys Tyr Glu Ile His Arg Asp Pro Thr Leu Asp
        290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
                340                 345                 350

Phe Asp Asp Ala Ile Glu Arg Ala Gly Gln Leu Thr Ser Glu Glu Asp
```

-continued

```
                355                 360                 365
Thr Leu Thr Leu Val Thr Ala Asp His Ser His Val Phe Ser Phe Gly
    370                 375                 380
Gly Tyr Thr Leu Arg Gly Ser Ser Ile Phe Gly Leu Ala Pro Ser Lys
385                 390                 395                 400
Ala Gln Asp Ser Lys Ala Tyr Thr Ser Ile Leu Tyr Gly Asn Gly Pro
                405                 410                 415
Gly Tyr Val Phe Asn Ser Gly Val Arg Pro Asp Val Asn Glu Ser Glu
            420                 425                 430
Ser Gly Ser Pro Asp Tyr Gln Gln Ala Ala Val Pro Leu Ser Ser
                435                 440                 445
Glu Thr His Gly Gly Glu Asp Val Ala Val Phe Ala Arg Gly Pro Gln
    450                 455                 460
Ala His Leu Val His Gly Val Gln Glu Gln Ser Phe Val Ala His Val
465                 470                 475                 480
Met Ala Phe Ala Ala Cys Leu Glu Pro Tyr Thr Ala Cys Asp Leu Ala
                485                 490                 495
Pro Pro Ala Cys Thr Thr Asp Ala Ala His Pro Val Ala Ala Ser Leu
                500                 505                 510
Pro Leu Leu Ala Gly Thr Leu Leu Leu Gly Ala Ser Ala Ala Pro
                515                 520                 525
```

<210> SEQ ID NO 2
<211> LENGTH: 420
<212> TYPE: PRT
<213> ORGANISM: Artificial Sequence
<220> FEATURE:
<223> OTHER INFORMATION: Synthetic polymer.

<400> SEQUENCE: 2

```
Met Gln Gly Ala Cys Val Leu Leu Leu Gly Leu His Leu Gln Leu
1               5                   10                  15
Ser Leu Gly Leu Ile Pro Ala Glu Glu Asn Pro Ala Phe Trp Asn
                20                  25                  30
Arg Gln Ala Ala Gln Ala Leu Asp Val Ala Lys Lys Leu Gln Pro Ile
            35                  40                  45
Gln Thr Ala Ala Lys Asn Val Ile Leu Phe Leu Gly Asp Gly Met Gly
    50                  55                  60
Val Pro Thr Val Thr Ala Thr Arg Ile Leu Lys Gly Gln Met Asn Gly
65                  70                  75                  80
Lys Leu Gly Pro Glu Thr Pro Leu Ala Met Asp Gln Phe Pro Tyr Val
                85                  90                  95
Ala Leu Ser Lys Thr Tyr Asn Val Asp Arg Gln Val Pro Asp Ser Ala
                100                 105                 110
Gly Thr Ala Thr Ala Tyr Leu Cys Gly Val Lys Gly Asn Tyr Arg Thr
            115                 120                 125
Ile Gly Val Ser Ala Ala Arg Tyr Asn Gln Cys Asn Thr Thr Arg
    130                 135                 140
Gly Asn Glu Val Thr Ser Val Ile Asn Arg Ala Lys Lys Ala Gly Lys
145                 150                 155                 160
Ala Val Gly Val Val Thr Thr Thr Arg Val Gln His Ala Ser Pro Ala
                165                 170                 175
Gly Ala Tyr Ala His Thr Val Asn Arg Asn Trp Tyr Ser Asp Ala Asp
            180                 185                 190
Leu Pro Ala Asp Ala Gln Lys Asn Gly Cys Gln Asp Ile Ala Ala Gln
```

```
                195                 200                 205
Leu Val Tyr Asn Met Asp Ile Asp Val Ile Leu Gly Gly Gly Arg Met
    210                 215                 220

Tyr Met Phe Pro Glu Gly Thr Pro Asp Pro Glu Tyr Pro Asp Asp Ala
225                 230                 235                 240

Ser Val Asn Gly Val Arg Lys Asp Lys Gln Asn Leu Val Gln Glu Trp
                245                 250                 255

Gln Ala Lys His Gln Gly Ala Gln Tyr Val Trp Asn Arg Thr Ala Leu
            260                 265                 270

Leu Gln Ala Ala Asp Asp Ser Ser Val Thr His Leu Met Gly Leu Phe
        275                 280                 285

Glu Pro Ala Asp Met Lys Tyr Asn Val Gln Gln Asp His Thr Lys Asp
    290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
                325                 330                 335

Gly His His Asp Gly Lys Ala Tyr Met Ala Leu Thr Glu Ala Ile Met
            340                 345                 350

Phe Asp Asn Ala Ile Ala Lys Ala Asn Glu Leu Thr Ser Glu Leu Asp
        355                 360                 365

Thr Leu Ile Leu Val Thr Ala Asp His Ser His Val Phe Ser Phe Gly
    370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
                405                 410                 415

Gly Tyr Ala Leu
            420

<210> SEQ ID NO 3
<211> LENGTH: 530
<212> TYPE: PRT
<213> ORGANISM: Artificial Sequence
<220> FEATURE:
<223> OTHER INFORMATION: Synthetic polymer.

<400> SEQUENCE: 3

Met Gln Trp Ala Cys Val Leu Leu Leu Gly Leu Trp Leu Gln Leu
1               5                   10                  15  Leu

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Ala Arg Tyr Asn Gln Cys Asn Thr Thr Ser
```

```
            130                 135                 140
Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                    165                 170                 175

Gly Ala Tyr Ala His Thr Val Asn Arg Asn Trp Tyr Ser Asp Ala Asp
                180                 185                 190

Leu Pro Ala Asp Ala Gln Thr Tyr Gly Cys Gln Asp Ile Ala Thr Gln
            195                 200                 205

Leu Val Asn Asn Met Asp Ile Asp Val Ile Leu Gly Gly Arg Met
210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                    245                 250                 255

Gln Ala Lys His Gln Gly Ala Gln Tyr Val Trp Asn Arg Thr Glu Leu
                260                 265                 270

Leu Gln Ala Ala Asn Asp Pro Ser Val Thr His Leu Met Gly Leu Phe
            275                 280                 285

Glu Pro Ala Asp Met Lys Tyr Asn Val Gln Gln Asp Pro Thr Lys Asp
290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                    325                 330                 335

Gly His His Glu Gly Lys Ala Tyr Met Ala Leu Thr Asp Thr Val Met
                340                 345                 350

Phe Asp Asn Ala Ile Ala Lys Ala Asn Glu Leu Thr Ser Glu Leu Asp
            355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                    405                 410                 415

Gly Tyr Val Leu Gly Gly Leu Arg Pro Asp Val Asn Asp Ser Ile
                420                 425                 430

Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                    485                 490                 495

Ala Pro Ser Gly Leu Ser Asp Ala Ala His Leu Ala Ala Ser Pro Pro
                500                 505                 510

Ser Leu Ala Leu Leu Ala Gly Ala Met Leu Leu Leu Ala Pro Ala
            515                 520                 525

Leu Tyr
    530

<210> SEQ ID NO 4
```

```
<211> LENGTH: 503
<212> TYPE: PRT
<213> ORGANISM: Artificial Sequence
<220> FEATURE:
<223> OTHER INFORMATION: Synthetic polymer.

<400> SEQUENCE: 4

Met Gln Gly Pro Trp Val Leu Leu Leu Gly Leu Arg Leu Gln Leu
1               5                   10                  15

Ser Leu Gly Val Ile Pro Ala Glu Glu Asn Pro Ala Phe Trp Asn
                20                  25                  30

Arg Gln Ala Ala Glu Ala Leu Asp Ala Ala Lys Lys Leu Gln Pro Ile
                35                  40                  45

Gln Lys Val Ala Lys Asn Leu Ile Leu Phe Leu Gly Asp Gly Leu Gly
50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
                100                 105                 110

Ala Thr Ala Thr Ala Tyr Leu Cys Gly Val Lys Ala Asn Phe Gln Thr
                115                 120                 125

Ile Gly Leu Ser Ala Ala Ala Arg Phe Asn Gln Cys Asn Thr Thr Arg
130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
                180                 185                 190

Met Pro Ala Ser Ala Arg Gln Glu Gly Cys Gln Asp Ile Ala Thr Gln
                195                 200                 205

Leu Ile Ser Asn Met Asp Ile Asp Val Ile Leu Gly Gly Gly Arg Lys
210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
                260                 265                 270

Met Gln Ala Ser Leu Asp Gln Ser Val Thr His Leu Met Gly Leu Phe
                275                 280                 285

Glu Pro Gly Asp Thr Lys Tyr Glu Ile His Arg Asp Pro Thr Leu Asp
                290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
                340                 345                 350

Phe Asp Asp Ala Ile Glu Arg Ala Gly Gln Leu Thr Ser Glu Glu Asp
                355                 360                 365

Thr Leu Thr Leu Val Thr Ala Asp His Ser His Val Phe Ser Phe Gly
                370                 375                 380
```

```
Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
            420                 425                 430

Ser Gly Ser Pro Asp Tyr Gln Gln Ala Ala Val Pro Leu Ser Ser
        435                 440                 445

Glu Thr His Gly Gly Glu Asp Val Ala Val Phe Ala Arg Gly Pro Gln
    450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Gly Thr Thr Asp
            500

<210> SEQ ID NO 5
<211> LENGTH: 506
<212> TYPE: PRT
<213> ORGANISM: Artificial Sequence
<220> FEATURE:
<223> OTHER INFORMATION: Synthetic polymer.

<400> SEQUENCE: 5

Met Gln Gly Ala Cys Val Leu Leu Leu Gly Leu His Leu Gln Leu
1               5                   10                  15

Ser Leu Gly Leu Ile Pro Ala Glu Glu Asn Pro Ala Phe Trp Asn
                20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
                100                 105                 110

Gly Thr Ala Thr Ala Tyr Leu Cys Gly Val Lys Gly Asn Tyr Arg Thr
            115                 120                 125

Ile Gly Val Ser Ala Ala Arg Tyr Asn Gln Cys Asn Thr Thr Arg
        130                 135                 140

Gly Asn Glu Val Thr Ser Val Ile Asn Arg Ala Lys Lys Ala Gly Lys
145                 150                 155                 160

Ala Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Lys Asn Gly Cys Gln Asp Ile Ala Ala Gln
        195                 200                 205

Leu Val Tyr Asn Met Asp Ile Asp Val Ile Leu Gly Gly Gly Arg Met
    210                 215                 220

Tyr Met Phe Pro Glu Gly Thr Pro Asp Pro Glu Tyr Pro Asp Asp Ala
225                 230                 235                 240
```

```
Ser Val Asn Gly Val Arg Lys Asp Lys Gln Asn Leu Val Gln Glu Trp
            245                 250                 255

Gln Ala Lys His Gln Gly Ala Gln Tyr Val Trp Asn Arg Thr Ala Leu
        260                 265                 270

Leu Gln Ala Ala Asp Asp Ser Ser Val Thr His Leu Met Gly Leu Phe
            275                 280                 285

Glu Pro Ala Asp Met Lys Tyr Asn Val Gln Gln Asp His Thr Lys Asp
290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
            325                 330                 335

Gly His His Asp Gly Lys Ala Tyr Met Ala Leu Thr Glu Ala Ile Met
            340                 345                 350

Phe Asp Asn Ala Ile Ala Lys Ala Asn Glu Leu Thr Ser Glu Leu Asp
            355                 360                 365

Thr Leu Ile Leu Val Thr Ala Asp His Ser His Val Phe Ser Phe Gly
        370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
            405                 410                 415

Gly Tyr Ala Leu Gly Gly Gly Ser Arg Pro Asp Val Asn Gly Ser Thr
            420                 425                 430

Ser Glu Glu Pro Ser Tyr Arg Gln Gln Ala Ala Val Pro Leu Ala Ser
            435                 440                 445

Glu Thr His Gly Gly Glu Asp Val Ala Val Phe Ala Arg Gly Pro Gln
        450                 455                 460

Ala His Leu Val His Gly Val Gln Glu Glu Thr Phe Val Ala His Ile
465                 470                 475                 480

Met Ala Phe Ala Gly Cys Val Glu Pro Tyr Thr Asp Cys Asn Leu Pro
            485                 490                 495

Ala Pro Ala Thr Ala Thr Ser Ile Pro Asp
            500                 505

<210> SEQ ID NO 6
<211> LENGTH: 503
<212> TYPE: PRT
<213> ORGANISM: Artificial Sequence
<220> FEATURE:
<223> OTHER INFORMATION: Synthetic polymer.

<400> SEQUENCE: 6

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95
```

```
Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
            115                 120                 125

Ile Gly Val Ser Ala Ala Arg Tyr Asn Gln Cys Asn Thr Thr Ser
130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                    165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
            195                 200                 205

Leu Val Asn Asn Met Asp Ile Asp Val Ile Leu Gly Gly Gly Arg Met
210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                    245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
            275                 280                 285

Glu Pro Ala Asp Met Lys Tyr Asn Val Gln Gln Asp Pro Thr Lys Asp
            290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                    325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
            355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                    405                 410                 415

Gly Tyr Val Leu Gly Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
            450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                    485                 490                 495

Ala Pro Ser Gly Leu Ser Asp
            500
```

```
<210> SEQ ID NO 7
<211> LENGTH: 508
<212> TYPE: PRT
<213> ORGANISM: Artificial Sequence
<220> FEATURE:
<223> OTHER INFORMATION: Synthetic polymer.

<400> SEQUENCE: 7

Met Gln Trp Ala Cys Val Leu Leu Leu Gly Leu Trp Leu Gln Leu
1               5                   10                  15

Ser Leu Thr Phe Ile Pro Ala Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
    290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
        355                 360                 365
```

```
Thr Leu Ile Leu Ala Thr Ala Asp His Ser His Val Phe Ser Phe Gly
        370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
                435                 440                 445

Glu Ser His Gly Gly Glu Asp Val Ala Val Phe Ala Arg Gly Pro Gln
450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly Leu Ser Asp Ala Ala His Leu Ala
                500                 505

<210> SEQ ID NO 8
<211> LENGTH: 754
<212> TYPE: PRT
<213> ORGANISM: Artificial Sequence
<220> FEATURE:
<223> OTHER INFORMATION: Synthetic polymer.

<400> SEQUENCE: 8

Met Gln Gly Ala Cys Val Leu Leu Leu Gly Leu His Leu Gln Leu
1               5                   10                  15

Ser Leu Gly Leu Ile Pro Ala Glu Glu Asn Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Arg Thr
        115                 120                 125

Ile Gly Val Ser Ala Ala Arg Tyr Asn Gln Cys Asn Thr Thr Arg
    130                 135                 140

Gly Asn Glu Val Thr Ser Val Ile Asn Arg Ala Lys Lys Ala Gly Lys
145                 150                 155                 160

Ala Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Lys Asn Gly Cys Gln Asp Ile Ala Ala Gln
        195                 200                 205

Leu Val Tyr Asn Met Asp Ile Asp Val Ile Leu Gly Gly Gly Arg Met
    210                 215                 220
```

```
Tyr Met Phe Pro Glu Gly Thr Pro Asp Pro Glu Tyr Pro Asp Asp Ala
225                 230                 235                 240

Ser Val Asn Gly Val Arg Lys Asp Lys Gln Asn Leu Val Gln Glu Trp
            245                 250                 255

Gln Ala Lys His Gln Gly Ala Gln Tyr Val Trp Asn Arg Thr Ala Leu
        260                 265                 270

Leu Gln Ala Ala Asp Asp Ser Ser Val Thr His Leu Met Gly Leu Phe
    275                 280                 285

Glu Pro Ala Asp Met Lys Tyr Asn Val Gln Gln Asp His Thr Lys Asp
290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
                325                 330                 335

Gly His His Asp Gly Lys Ala Tyr Met Ala Leu Thr Glu Ala Ile Met
            340                 345                 350

Phe Asp Asn Ala Ile Ala Lys Ala Asn Glu Leu Thr Ser Glu Leu Asp
        355                 360                 365

Thr Leu Ile Leu Val Thr Ala Asp His Ser His Val Phe Ser Phe Gly
370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
                405                 410                 415

Gly Tyr Ala Leu Gly Gly Ser Arg Pro Asp Val Asn Gly Ser Thr
            420                 425                 430

Ser Glu Glu Pro Ser Tyr Arg Gln Gln Ala Ala Val Pro Leu Ala Ser
            435                 440                 445

Glu Thr His Gly Gly Glu Asp Val Ala Val Phe Ala Arg Gly Pro Gln
    450                 455                 460

Ala His Leu Val His Gly Val Gln Glu Glu Thr Phe Val Ala His Ile
465                 470                 475                 480

Met Ala Phe Ala Gly Cys Val Glu Pro Tyr Thr Asp Cys Asn Leu Pro
                485                 490                 495

Ala Pro Ala Thr Ala Thr Ser Ile Pro Asp Gly Gly Ser Gly Gly Ser
            500                 505                 510

Gly Gly Gly Gly Ser Gly Gly Gly Ser Glu Pro Lys Ser Cys Asp
        515                 520                 525

Lys Thr His Thr Cys Pro Pro Cys Pro Ala Pro Glu Leu Leu Gly Gly
    530                 535                 540

Pro Ser Val Phe Leu Phe Pro Pro Lys Pro Lys Asp Thr Leu Met Ile
545                 550                 555                 560

Ser Arg Thr Pro Glu Val Thr Cys Val Val Val Asp Val Ser His Glu
                565                 570                 575

Asp Pro Gln Val Lys Phe Asn Trp Tyr Val Asp Gly Val Gln Val His
            580                 585                 590

Asn Ala Lys Thr Lys Pro Arg Glu Gln Gln Tyr Asn Ser Thr Tyr Arg
        595                 600                 605

Val Val Ser Val Leu Thr Val Leu His Gln Asn Trp Leu Asp Gly Lys
    610                 615                 620

Glu Tyr Lys Cys Lys Val Ser Asn Lys Ala Leu Pro Ala Pro Ile Glu
625                 630                 635                 640

Lys Thr Ile Ser Lys Ala Lys Gly Gln Pro Arg Glu Pro Gln Val Tyr
```

-continued

```
                645                 650                 655
Thr Leu Pro Pro Ser Arg Glu Glu Met Thr Lys Asn Gln Val Ser Leu
            660                 665                 670

Thr Cys Leu Val Lys Gly Phe Tyr Pro Ser Asp Ile Ala Val Glu Trp
            675                 680                 685

Glu Ser Asn Gly Gln Pro Glu Asn Asn Tyr Lys Thr Thr Pro Pro Val
            690                 695                 700

Leu Asp Ser Asp Gly Ser Phe Phe Leu Tyr Ser Lys Leu Thr Val Asp
705                 710                 715                 720

Lys Ser Arg Trp Gln Gln Gly Asn Val Phe Ser Cys Ser Val Met His
                725                 730                 735

Glu Ala Leu His Asn His Tyr Thr Gln Lys Ser Leu Ser Leu Ser Pro
            740                 745                 750

Gly Lys
```

<210> SEQ ID NO 9
<211> LENGTH: 751
<212> TYPE: PRT
<213> ORGANISM: Artificial Sequence
<220> FEATURE:
<223> OTHER INFORMATION: Synthetic polymer.

<400> SEQUENCE: 9

```
Met Gln Trp Ala Cys Val Leu Leu Leu Gly Leu Trp Leu Gln Leu
1               5                   10                  15

Ser Leu Thr Phe Ile Pro Ala Glu Glu Asp Pro Ala Phe Trp Asn
                20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
        50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255
```

-continued

```
Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Arg Ile Asp His
                325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
        355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
        435                 440                 445

Glu Ser His Gly Gly Glu Asp Val Ala Val Phe Ala Arg Gly Pro Gln
450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly Leu Ser Asp Gly Gly Ser Gly Ser Gly Gly Gly
            500                 505                 510

Gly Ser Gly Gly Gly Gly Ser Glu Pro Lys Ser Cys Asp Lys Thr His
        515                 520                 525

Thr Cys Pro Pro Cys Pro Ala Pro Glu Leu Leu Gly Gly Pro Ser Val
530                 535                 540

Phe Leu Phe Pro Pro Lys Pro Lys Asp Thr Leu Met Ile Ser Arg Thr
545                 550                 555                 560

Pro Glu Val Thr Cys Val Val Val Asp Val Ser His Glu Asp Pro Gln
                565                 570                 575

Val Lys Phe Asn Trp Tyr Val Asp Gly Val Gln Val His Asn Ala Lys
            580                 585                 590

Thr Lys Pro Arg Glu Gln Gln Tyr Asn Ser Thr Tyr Arg Val Val Ser
        595                 600                 605

Val Leu Thr Val Leu His Gln Asn Trp Leu Asp Gly Lys Glu Tyr Lys
610                 615                 620

Cys Lys Val Ser Asn Lys Ala Leu Pro Ala Pro Ile Glu Lys Thr Ile
625                 630                 635                 640

Ser Lys Ala Lys Gly Gln Pro Arg Glu Pro Gln Val Tyr Thr Leu Pro
                645                 650                 655

Pro Ser Arg Glu Glu Met Thr Lys Asn Gln Val Ser Leu Thr Cys Leu
            660                 665                 670
```

Val Lys Gly Phe Tyr Pro Ser Asp Ile Ala Val Glu Trp Glu Ser Asn
            675                 680                 685

Gly Gln Pro Glu Asn Asn Tyr Lys Thr Thr Pro Pro Val Leu Asp Ser
    690                 695                 700

Asp Gly Ser Phe Phe Leu Tyr Ser Lys Leu Thr Val Asp Lys Ser Arg
705                 710                 715                 720

Trp Gln Gln Gly Asn Val Phe Ser Cys Ser Val Met His Glu Ala Leu
                725                 730                 735

His Asn His Tyr Thr Gln Lys Ser Leu Ser Leu Ser Pro Gly Lys
            740                 745                 750

<210> SEQ ID NO 10
<211> LENGTH: 539
<212> TYPE: PRT
<213> ORGANISM: Artificial Sequence
<220> FEATURE:
<223> OTHER INFORMATION: Synthetic polymer.

<400> SEQUENCE: 10

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
            325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
            355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
            405                 410                 415

Gly Tyr Val Leu Gly Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Glu
            485                 490                 495

Val Leu Phe Gln Gly Pro Ala Pro Ala Gly Thr Thr Asp Ala Ala
            500                 505                 510

His Pro Gly Arg Ser Val Val Pro Ala Leu Leu Pro Leu Arg Ala Gly
            515                 520                 525

Thr Leu Leu Leu Leu Glu Thr Ala Thr Ala Pro
            530                 535

<210> SEQ ID NO 11
<211> LENGTH: 534
<212> TYPE: PRT
<213> ORGANISM: Artificial Sequence
<220> FEATURE:
<223> OTHER INFORMATION: Synthetic polymer.

<400> SEQUENCE: 11

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

```
Gly Thr Ala Thr Ala Tyr Leu Cys Gly Val Lys Gly Asn Tyr Lys Thr
            115                 120                 125
Ile Gly Val Ser Ala Ala Arg Tyr Asn Gln Cys Asn Thr Thr Ser
    130                 135                 140
Gly Asn Glu Val Thr Ser Val Met Asn Arg Ala Lys Lys Ala Gly Lys
145                 150                 155                 160
Ser Val Gly Val Val Thr Thr Ser Arg Val Gln His Ala Ser Pro Ala
                165                 170                 175
Gly Ala Tyr Ala His Thr Val Asn Arg Asn Trp Tyr Ser Asp Ala Asp
            180                 185                 190
Leu Pro Ala Asp Ala Gln Thr Tyr Gly Cys Gln Asp Ile Ala Thr Gln
            195                 200                 205
Leu Val Asn Asn Met Asp Ile Asp Val Ile Leu Gly Gly Gly Arg Met
210                 215                 220
Tyr Met Phe Pro Glu Gly Thr Pro Asp Pro Glu Tyr Pro Tyr Asp Val
225                 230                 235                 240
Asn Gln Thr Gly Val Arg Lys Asp Lys Arg Asn Leu Val Gln Glu Trp
                245                 250                 255
Gln Ala Lys His Gln Gly Ala Gln Tyr Val Trp Asn Arg Thr Glu Leu
            260                 265                 270
Leu Gln Ala Ala Asn Asp Pro Ser Val Thr His Leu Met Gly Leu Phe
275                 280                 285
Glu Pro Ala Asp Met Lys Tyr Asn Val Gln Gln Asp Pro Thr Lys Asp
            290                 295                 300
Pro Thr Leu Glu Glu Met Thr Glu Ala Ala Leu Gln Val Leu Ser Arg
305                 310                 315                 320
Asn Pro Gln Gly Phe Tyr Leu Phe Val Glu Gly Gly Arg Ile Asp His
                325                 330                 335
Gly His His Glu Gly Lys Ala Tyr Met Ala Leu Thr Asp Thr Val Met
            340                 345                 350
Phe Asp Asn Ala Ile Ala Lys Ala Asn Glu Leu Thr Ser Glu Leu Asp
            355                 360                 365
Thr Leu Ile Leu Ala Thr Ala Asp His Ser His Val Phe Ser Phe Gly
370                 375                 380
Gly Tyr Thr Leu Arg Gly Thr Ser Ile Phe Gly Leu Ala Pro Ser Lys
385                 390                 395                 400
Ala Ser Asp Asn Lys Ser Tyr Thr Ser Ile Leu Tyr Gly Asn Gly Pro
                405                 410                 415
Gly Tyr Val Leu Gly Gly Leu Arg Pro Asp Val Asn Asp Ser Ile
            420                 425                 430
Ser Glu Asp Pro Ser Tyr Arg Gln Gln Ala Ala Val Pro Leu Ser Ser
            435                 440                 445
Glu Ser His Gly Gly Glu Asp Val Ala Val Phe Ala Arg Gly Pro Gln
450                 455                 460
Ala His Leu Val His Gly Val Gln Glu Glu Thr Phe Val Ala His Val
465                 470                 475                 480
Met Ala Phe Ala Gly Cys Val Glu Pro Tyr Thr Asp Cys Asn Leu Ala
                485                 490                 495
Pro Pro Ala Gly Thr Thr Asp Ala Ala His Pro Ile Glu Gly Arg Ser
            500                 505                 510
Val Val Pro Ala Leu Leu Pro Leu Arg Ala Gly Thr Leu Leu Leu Leu
515                 520                 525
Glu Thr Ala Thr Ala Pro
```

<210> SEQ ID NO 12
<211> LENGTH: 1669
<212> TYPE: DNA
<213> ORGANISM: Artificial Sequence
<220> FEATURE:
<223> OTHER INFORMATION: Synthetic polymer.

<400> SEQUENCE: 12

| | | | | | |
|---|---|---|---|---|---|
| atgcaggggc | cctgggtgct | gctgctgctg | ggcctgaggc | tacagctctc | cctgggcgtc | 60 |
| atcccaggta | atgaggctcc | ccaagctgtt | ccacacacag | ggcaccccct | cagccaggct | 120 |
| gacctgatct | ctactctccc | cctggccagc | tgaggaggag | aacccggcct | tctggaaccg | 180 |
| ccaggcagct | gaggccctgg | atgctgccaa | gaagctgcag | cccatccaga | aggtcgccaa | 240 |
| gaacctcatc | ctcttcctgg | gcgatgggtt | ggggtgccc | acggtgacag | ccaccaggat | 300 |
| cctaaagggg | cagaagaatg | caaactggg | gcctgagacg | ccctggcca | tggaccgctt | 360 |
| cccatacctg | gctctgtcca | agacatacaa | tgtggacaga | caggtgccag | acagcgcagc | 420 |
| cacagccacg | gcctacctgt | gcggggtcaa | ggccaacttc | cagaccatcg | gcttgagtgc | 480 |
| agccgcccgc | tttaaccagt | gcaacacgac | acgcggcaat | gaggtcatct | ccgtgatgaa | 540 |
| ccgggccaag | caagcaggaa | agtcagtagg | agtggtgacc | accacacggg | tgcagcacgc | 600 |
| ctcgccagcc | ggcacctacg | cacacacagt | gaaccgcaac | tggtactcag | atgctgacat | 660 |
| gcctgcctca | gcccgccagg | aggggtgcca | ggacatcgcc | actcagctca | tctccaacat | 720 |
| ggacattgac | gtgatccttg | gcggaggccg | caagtacatg | tttcccatgg | ggacccccaga | 780 |
| ccctgagtac | ccagctgatg | ccagccagaa | tggaatcagg | ctggacggga | agaacctggt | 840 |
| gcaggaatgg | ctggcaaagc | accagggtgc | ctggtatgtg | tggaaccgca | ctgagctcat | 900 |
| gcaggcgtcc | ctggaccagt | ctgtgaccca | tctcatgggc | ctctttgagc | ccggagacac | 960 |
| gaaatatgag | atccaccgag | accccacact | ggacccctcc | ctgatggaga | tgacagaggc | 1020 |
| tgccctgcgc | ctgctgagca | ggaaccccccg | cggcttctac | ctctttgtgg | agggcggccg | 1080 |
| catcgaccat | ggtcatcatg | agggtgtggc | ttaccaggca | ctcactgagg | cggtcatgtt | 1140 |
| cgacgacgcc | attgagaggg | cgggccagct | caccagcgag | gaggacacgc | tgacccctcgt | 1200 |
| caccgctgac | cactcccatg | tcttctcctt | tggtggctac | accttgcgag | ggagctccat | 1260 |
| cttcgggttg | gcccccagca | aggctcagga | cagcaaagcc | tacacgtcca | tcctgtacgg | 1320 |
| caatggcccg | ggctacgtgt | tcaactcagg | cgtgcgacca | gacgtgaatg | agagcgagag | 1380 |
| cgggagcccc | gattaccagc | agcaggcggc | ggtgccctg | tcgtccgaga | cccacggagg | 1440 |
| cgaagacgtg | gcggtgtttg | cgcgcggccc | gcaggcgcac | ctggtgcatg | gtgtgcagga | 1500 |
| gcagagcttc | gtagcgcatg | tcatggcctt | cgctgcctgt | ctggagccct | acacggcctg | 1560 |
| cgacctggcg | cctcccgcct | gcaccaccga | cgccgcgcac | ccagttgccg | cgtcgctgcc | 1620 |
| actgctggcc | gggaccctgc | tgctgctggg | ggcgtccgct | gctcccctga | | 1669 |

<210> SEQ ID NO 13
<211> LENGTH: 1671
<212> TYPE: DNA
<213> ORGANISM: Artificial Sequence
<220> FEATURE:
<223> OTHER INFORMATION: Synthetic polymer.

<400> SEQUENCE: 13
atgcaggggc cctgggtgct gctgctgctg ggcctgaggc tacagctctc cctgggcgtc    60

```
atcccagctg aggaggagaa cccggccttc tggaaccgcc aggcagctga ggccctggat      120
gctgccaaga agctgcagcc catccagaag gtcgccaaga acctcatcct cttcctgggc      180
gatgggttgg gggtgcccac ggtgacagcc accaggatcc taaagggca gaagaatggc      240 aaactgggc ctgagacgcc cctggccatg accgcttcc catacctggc tctgtccaag        300
acatacaatg tggacagaca ggtgccagac agcgcagcca cagccacggc ctacctgtgc      360
ggggtcaagg ccaacttcca gaccatcggc ttgagtgcag ccgcccgctt taaccagtgc      420
aacacgacac gcggcaatga ggtcatctcc gtgatgaacc gggccaagca agcaggaaag      480
tcagtaggag tggtgaccac cacacgggtg cagcacgcct cgccagccgg cacctacgca      540
cacacagtga accgcaactg gtactcagat gctgacatgc ctgcctcagc ccgccaggag      600
gggtgccagg acatcgccac tcagctcatc tccaacatgg acattgacgt gatccttggc      660
ggaggccgca agtacatgtt tcccatgggg accccagacc ctgagtaccc agctgatgcc      720
agccagaatg gaatcaggct ggacgggaag aacctggtgc aggaatggct ggcaaagcac      780
cagggtgcct ggtatgtgtg aaccgcact gagctcatgc aggcgtccct ggaccagtct        840
gtgacccatc tcatgggcct cttgagccc ggagacacga aatatgagat ccaccgagac       900
cccacactgg accctccct gatggagatg acagaggctg ccctgcgcct gctgagcagg       960 aaccccgcg gcttctacct ctttgtggag gcggccgca tcgaccatgg tcatcatgag        1020
ggtgtggctt accaggcact cactgaggcg gtcatgttcg acgacgccat tgagagggcg     1080
ggccagctca ccagcgagga ggacacgctg accctcgtca ccgctgacca ctcccatgtc     1140
ttctcctttg gtggctacac cttgcgaggg agctccatct tcgggttggc ccccagcaag     1200
gctcaggaca gcaaagccta cacgtccatc ctgtacggca atggcccggg ctacgtgttc     1260
aactcaggcg tgcgaccaga cgtgaatgag agcgagagcc ggagccccga ttaccagcag     1320
caggcggcgg tgcccctgtc gtccgagacc cacggaggcg aagacgtggc ggtgtttgcg     1380
cgcggcccgc aggcgcacct ggtgcatggt gtgcaggagc agagcttcgt agcgcatgtc     1440
atggccttcg ctgcctgtct ggagccctac acggccgcg acctggcgcc tcccgcctgc      1500
accaccgacg ccgcgcaccc agttgccgcg tcgctgccac tgctggccgg gaccctgctg     1560
ctgctggggg cgtccgctgc tccctgattt actaaaacct gaaataaaa ttgtaaaaca      1620 tcagtttgaa ggcctgactc tcagggtagt tctttttaa ttctgggttt t               1671
```

<210> SEQ ID NO 14
<211> LENGTH: 1672
<212> TYPE: DNA
<213> ORGANISM: Artificial Sequence
<220> FEATURE:
<223> OTHER INFORMATION: Synthetic polymer.

<400> SEQUENCE: 14

```
atgcagtggg cctgtgtgct gctgctgctg ggcctgtggc tacagctctc cctcaccttc       60
atcccaggta atcaggcggc tcccagcagc ccctactcac aggggcggct ctaggctgac      120
ctgaccaaca ctctcccctt gggcagctga ggaggaagac cccgccttct ggaaccgcca      180
ggcagcccag gcccttgatg tagccaagaa gttgcagccg atccagacag ctgccaagaa     240
tgtcatcctc ttcttggggg atgggatggg ggtgcctacg gtgacagcca ctcggatcct     300
aaaggggcag atgaatggta agctgggacc tgagacaccc ctggccatgg accagttccc      360
atacgtggct ctgtccaaga catacaacgt ggacagacag gtgccagaca gcgcaggcac      420
```

```
tgccactgcc tacctgtgtg gggtcaaggg caactacaaa accattggtg taagtgcagc    480
cgcccgctac aaccagtgca acacaacaag tggcaatgag gtcacgtctg tgatgaaccg    540
ggccaagaaa gcaggaaagt cagtgggagt ggtgaccacc tccagggtgc agcatgcctc    600
cccagccggt gcttatgcac acacggtgaa ccgaaactgg tactcagatg ccgacctgcc    660
tgccgatgca cagacgtatg gctgccagga catcgccaca caactggtca acaacatgga    720
tattgacgtg atcctgggtg gaggccgaat gtacatgttt cctgagggga ccccggatcc    780
tgaatacccca tacgatgtca atcagactgg agtccggaag gacaagcgga atctggtgca    840
ggagtggcag gccaagcacc agggagccca gtatgtgtgg aaccgcacgg agctccttca    900
ggcagccaat gaccccagtg taacacacct catgggcctc tttgagccgg cagacatgaa    960
gtataatgtt cagcaagacc ccaccaagga cccgaccctg gaggagatga cggaggcggc   1020
cctgcaagtg ctgagcagga accccaggg cttctacctc ttcgtggagg aggccgcat    1080
tgaccacggt caccatgaag gcaaagctta tatggcactg actgatacag tcatgtttga    1140
caatgccatc gccaaggcta acgagctcac tagcgaactg acacgctga tccttgccac    1200
tgcagaccac tcccatgtct tctcttttgg tggctacaca ctgcgtggga cctccatttt    1260
cggtctggcc cccagcaagg cctcagacaa caagtcctac acctccatcc tctatggcaa    1320
tggccctggc tacgtgcttg gtgggggctt aaggcccgat gttaatgaca gcataagcga    1380
ggaccccteg taccggcagc aggcggccgt gcccctgtct agtgagtccc acgggggcga    1440
ggacgtggcg gtgttcgcgc gaggcccgca ggcgcacctg gtgcacggcg tgcaggagga    1500
gaccttcgtg gcgcacgtca tggccttgc gggctgcgtg gagccctaca ccgactgcaa    1560
tctgccggcc ccctctggcc tctccgacgc cgcgcacctg cggccagcc cgccttcgct    1620
ggcgctgctg gccggggcga tgctgctgct gctggcgcct gccttgtact ga             1672
```

<210> SEQ ID NO 15
<211> LENGTH: 1869
<212> TYPE: DNA
<213> ORGANISM: Artificial Sequence
<220> FEATURE:
<223> OTHER INFORMATION: Synthetic polymer.

<400> SEQUENCE: 15

```
atgcagtggg cctgtgtgct gctgctgctg ggcctgtggc tacagctctc cctcaccttc     60
atcccagctg aggaggaaga ccccgccttc tggaaccgcc aggcagccca ggcccttgat    120
gtagccaaga agttgcagcc gatccagaca gctgccaaga atgtcatcct cttcttgggg    180
gatgggatgg gggtgcctac ggtgacagcc actcggatcc taaagggca gatgaatggt    240
aagctgggac ctgagacacc cctggccatg gaccagttcc catacgtggc tctgtccaag    300
acatacaacg tggacagaca ggtgccagac agcgcaggca ctgccactgc ctacctgtgt    360
ggggtcaagg gcaactacaa aaccattggt gtaagtgcag ccgcccgcta caaccagtgc    420
aacacaacaa gtggcaatga ggtcacgtct gtgatgaacc gggccaagaa agcaggaaag    480
tcagtgggag tggtgaccac ctccagggtg cagcatgcct ccccagccgg tgcttatgca    540
cacacggtga accgaaactg gtactcagat gccgacctgc ctgccgatgc acagacgtat    600
ggctgccagg acatcgccac acaactggtc aacaacatgg atattgacgt gatcctgggt    660
ggaggccgaa tgtacatgtt tcctgagggg accccggatc ctgaataccc atacgatgtc    720
aatcagactg gagtccggaa ggacaagcgg aatctggtgc aggagtggca ggccaagcac    780
cagggagccc agtatgtgtg gaaccgcacg gagctccttc aggcagccaa tgaccccagt    840
```

| | | | | |
|---|---|---|---|---|
| gtaacacacc | tcatgggcct | ctttgagccg | gcagacatga | agtataatgt | tcagcaagac | 900 |
| cccaccaagg | acccgaccct | ggaggagatg | acggaggcgg | ccctgcaagt | gctgagcagg | 960 |
| aaccccagg | gcttctacct | cttcgtggag | ggaggccgca | ttgaccacgg | tcaccatgaa | 1020 |
| ggcaaagctt | atatggcact | gactgataca | gtcatgtttg | acaatgccat | cgccaaggct | 1080 |
| aacgagctca | ctagcgaact | ggacacgctg | atccttgcca | ctgcagacca | ctcccatgtc | 1140 |
| ttctcttttg | gtggctacac | actgcgtggg | acctccattt | tcggtctggc | ccccagcaag | 1200 |
| gcctcagaca | caagtccta | cacctccatc | ctctatggca | atggccctgg | ctacgtgctt | 1260 |
| ggtgggggct | taaggcccga | tgttaatgac | agcataagcg | aggaccctc | gtaccggcag | 1320 |
| caggcggccg | tgcccctgtc | tagtgagtcc | cacggggcg | aggacgtggc | ggtgttcgcg | 1380 |
| cgaggcccgc | aggcgcacct | ggtgcacggc | gtgcaggagg | agaccttcgt | ggcgcacgtc | 1440 |
| atggcctttg | cgggctgcgt | ggagccctac | accgactgca | atctgccggc | ccctctggc | 1500 |
| ctctccgacg | ccgcgcacct | ggcggccagc | ccgccttcgc | tggcgctgct | ggccggggcg | 1560 |
| atgctgctgc | tgctggcgcc | tgccttgtac | tgagggacc | cggggtggg | gacacaggcc | 1620 |
| ccgccctccc | tgggaggcag | gaagcagctc | tcaaataaac | tgttctaagt | atgatacagg | 1680 |
| agtgatacat | gtgtgaagag | aagcccttag | gtggggcac | agagtgtctg | ggtgaggggg | 1740 |
| gtcagggtca | catcaggagg | ttagggaggg | gttgatgaag | ggctgacgtt | gagcaaagac | 1800 |
| caaaggcaac | tcagaaggac | agtggtgcag | gactgggtgt | ggtcagcagg | gggactggtt | 1860 |
| gggggatcc | | | | | | 1869 |

<210> SEQ ID NO 16
<211> LENGTH: 1260
<212> TYPE: DNA
<213> ORGANISM: Artificial Sequence
<220> FEATURE:
<223> OTHER INFORMATION: Synthetic polymer.

<400> SEQUENCE: 16

| | | | | |
|---|---|---|---|---|
| aaaaaacaag | acaaagctga | gatcagaaat | gtcattgtga | tgataggcga | cggcatgggg | 60 |
| acgccttaca | taagagccta | ccgttccatg | aaaaataacg | gtgacacacc | gaataacccg | 120 |
| aagttaacag | aatttgaccg | gaacctgaca | ggcatgatga | tgacgcatcc | ggatgaccct | 180 |
| gactataata | ttcagattc | agcagcagcc | ggaacagcat | tagcgacagg | cgttaagaca | 240 |
| tataacaatg | caattggcgt | cgataaaaac | ggaaaaaag | tgaaatctgt | acttgaagag | 300 |
| gccaaacagc | aaggcaagtc | aacagggctt | gtcgccacgt | ctgaaattaa | ccacgccact | 360 |
| ccagccgcat | atggcgccca | caatgaatca | cggaaaaaca | tggaccaaat | cgccaacagc | 420 |
| tatatggatg | acaagataaa | aggcaaacat | aaaatagacg | tgctgctcgg | cggcggaaaa | 480 |
| tcttattta | accgcaagaa | cagaaacttg | acaaaggaat | tcaaacaagc | cggctacagc | 540 |
| tatgtgacaa | ctaaacaagc | attgaaaaaa | aataaagatc | agcaggtgct | cgggcttttc | 600 |
| gcagatggag | ggcttgctaa | agcgctcgac | cgtgacagta | aaacaccgtc | tctcaaagac | 660 |
| atgacggttt | cagcaattga | tcgcctgaac | caaaataaaa | aaggattttt | cttgatggtc | 720 |
| gaagggagcc | agattgactg | gcggccccat | gacaatgata | cagtaggagc | catgagcgag | 780 |
| gttaaagatt | ttgaacaggc | ctataaagcc | gcgattgaat | ttgcgaaaaa | agacaaacat | 840 |
| acacttgtga | ttcaactgc | tgaccataca | accggcggct | ttaccattgg | cgcaaacggg | 900 |
| gaaaagaatt | ggcacgcaga | accgattctc | tccgctaaga | aaacacctga | attcatggcc | 960 |

```
aaaaaaatca gtgaaggcaa gccggttaaa gatgtgctcg cccgctatgc caatctgaaa    1020
gtcacatctg aagaaatcaa aagcgttgaa gcagctgcac aggctgacaa aagcaaaggg    1080
gcctccaaag ccatcatcaa gattttaat acccgctcca acagcggatg gacgagtacc     1140
gatcataccg gcgaagaagt accggtatac gcgtacggcc ccggaaaaga aaaattccgc    1200
ggattgatta caatacgga ccaggcaaac atcatattta agattttaaa aactggaaaa     1260
```

<210> SEQ ID NO 17
<211> LENGTH: 420
<212> TYPE: PRT
<213> ORGANISM: Artificial Sequence
<220> FEATURE:
<223> OTHER INFORMATION: Synthetic polymer.

<400> SEQUENCE: 17

```
Lys Lys Gln Asp Lys Ala Glu Ile Arg Asn Val Ile Val Met Ile Gly
1               5                   10                  15

Asp Gly Met Gly Thr Pro Tyr Ile Arg Ala Tyr Arg Ser Met Lys Asn
            20                  25                  30

Asn Gly Asp Thr Pro Asn Asn Pro Lys Leu Thr Glu Phe Asp Arg Asn
        35                  40                  45

Leu Thr Gly Met Met Met Thr His Pro Asp Asp Pro Asp Tyr Asn Ile
    50                  55                  60

Thr Asp Ser Ala Ala Ala Gly Thr Ala Leu Ala Thr Gly Val Lys Thr
65                  70                  75                  80

Tyr Asn Asn Ala Ile Gly Val Asp Lys Asn Gly Lys Lys Val Lys Ser
                85                  90                  95

Val Leu Glu Glu Ala Lys Gln Gln Gly Lys Ser Thr Gly Leu Val Ala
            100                 105                 110

Thr Ser Glu Ile Asn His Ala Thr Pro Ala Ala Tyr Gly Ala His Asn
        115                 120                 125

Glu Ser Arg Lys Asn Met Asp Gln Ile Ala Asn Ser Tyr Met Asp Asp
    130                 135                 140

Lys Ile Lys Gly Lys His Lys Ile Asp Val Leu Leu Gly Gly Gly Lys
145                 150                 155                 160

Ser Tyr Phe Asn Arg Lys Asn Arg Asn Leu Thr Lys Glu Phe Lys Gln
                165                 170                 175

Ala Gly Tyr Ser Tyr Val Thr Thr Lys Gln Ala Leu Lys Lys Asn Lys
            180                 185                 190

Asp Gln Gln Val Leu Gly Leu Phe Ala Asp Gly Gly Leu Ala Lys Ala
        195                 200                 205

Leu Asp Arg Asp Ser Lys Thr Pro Ser Leu Lys Asp Met Thr Val Ser
    210                 215                 220

Ala Ile Asp Arg Leu Asn Gln Asn Lys Lys Gly Phe Phe Leu Met Val
225                 230                 235                 240

Glu Gly Ser Gln Ile Asp Trp Ala Ala His Asp Asn Asp Thr Val Gly
                245                 250                 255

Ala Met Ser Glu Val Lys Asp Phe Glu Gln Ala Tyr Lys Ala Ala Ile
            260                 265                 270

Glu Phe Ala Lys Lys Asp Lys His Thr Leu Val Ile Ala Thr Ala Asp
        275                 280                 285

His Thr Thr Gly Gly Phe Thr Ile Gly Ala Asn Gly Glu Lys Asn Trp
    290                 295                 300

His Ala Glu Pro Ile Leu Ser Ala Lys Lys Thr Pro Glu Phe Met Ala
305                 310                 315                 320
```

```
Lys Lys Ile Ser Glu Gly Lys Pro Val Lys Asp Val Leu Ala Arg Tyr
            325                 330                 335

Ala Asn Leu Lys Val Thr Ser Glu Glu Ile Lys Ser Val Glu Ala Ala
            340                 345                 350

Ala Gln Ala Asp Lys Ser Lys Gly Ala Ser Lys Ala Ile Ile Lys Ile
            355                 360                 365

Phe Asn Thr Arg Ser Asn Ser Gly Trp Thr Ser Thr Asp His Thr Gly
            370                 375                 380

Glu Glu Val Pro Val Tyr Ala Tyr Gly Pro Gly Lys Glu Lys Phe Arg
385                 390                 395                 400

Gly Leu Ile Asn Asn Thr Asp Gln Ala Asn Ile Ile Phe Lys Ile Leu
            405                 410                 415

Lys Thr Gly Lys
            420

<210> SEQ ID NO 18
<211> LENGTH: 776
<212> TYPE: PRT
<213> ORGANISM: Artificial Sequence
<220> FEATURE:
<223> OTHER INFORMATION: Synthetic polymer.

<400> SEQUENCE: 18

Met Gln Gly Pro Trp Val Leu Leu Leu Leu Gly Leu Arg Leu Gln Leu
1               5                   10                  15

Ser Leu Gly Val Ile Pro Ala Glu Glu Asn Pro Ala Phe Trp Asn
            20                  25                  30

Arg Gln Ala Ala Glu Ala Leu Asp Ala Ala Lys Lys Leu Gln Pro Ile
            35                  40                  45

Gln Lys Val Ala Lys Asn Leu Ile Leu Phe Leu Gly Asp Gly Leu Gly
        50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
            85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr
            115                 120                 125

Ile Gly Leu Ser Ala Ala Ala Arg Phe Asn Gln Cys Asn Thr Thr Arg
        130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
            165                 170                 175

Gly Thr Tyr Ala His Thr Val Asn Arg Asn Trp Tyr Ser Asp Ala Asp
            180                 185                 190

Met Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Gly Arg Lys
        210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
            245                 250                 255
```

```
Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
        275                 280                 285

Glu Pro Gly Asp Thr Lys Tyr Glu Ile His Arg Asp Pro Thr Leu Asp
    290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Arg Ile Asp His
                325                 330                 335

Gly His His Glu Gly Val Ala Tyr Gln Ala Leu Thr Glu Ala Val Met
            340                 345                 350

Phe Asp Asp Ala Ile Glu Arg Ala Gly Gln Leu Thr Ser Glu Glu Asp
        355                 360                 365

Thr Leu Thr Leu Val Thr Ala Asp His Ser His Val Phe Ser Phe Gly
    370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
            420                 425                 430

Ser Gly Ser Pro Asp Tyr Gln Gln Gln Ala Ala Val Pro Leu Ser Ser
        435                 440                 445

Glu Thr His Gly Gly Glu Asp Val Ala Val Phe Ala Arg Gly Pro Gln
    450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Cys Thr Thr Asp Ala Ala His Pro Val Ala Ala Ser Leu
            500                 505                 510

Pro Leu Leu Ala Gly Thr Leu Leu Leu Gly Ala Ser Ala Ala Pro
        515                 520                 525

Gly Gly Ser Gly Gly Ser Gly Gly Gly Ser Gly Gly Gly Gly Ser
530                 535                 540

Glu Pro Lys Ser Cys Asp Lys Thr His Thr Cys Pro Pro Cys Pro Ala
545                 550                 555                 560

Pro Glu Leu Leu Gly Gly Pro Ser Val Phe Leu Phe Pro Pro Lys Pro
                565                 570                 575

Lys Asp Thr Leu Met Ile Ser Arg Thr Pro Glu Val Thr Cys Val Val
            580                 585                 590

Val Asp Val Ser His Glu Asp Pro Gln Val Lys Phe Asn Trp Tyr Val
        595                 600                 605

Asp Gly Val Gln Val His Asn Ala Lys Thr Lys Pro Arg Glu Gln Gln
    610                 615                 620

Tyr Asn Ser Thr Tyr Arg Val Val Ser Val Leu Thr Val Leu His Gln
625                 630                 635                 640

Asn Trp Leu Asp Gly Lys Glu Tyr Lys Cys Lys Val Ser Asn Lys Ala
                645                 650                 655

Leu Pro Ala Pro Ile Glu Lys Thr Ile Ser Lys Ala Lys Gly Gln Pro
            660                 665                 670
```

Arg Glu Pro Gln Val Tyr Thr Leu Pro Pro Ser Arg Glu Glu Met Thr
                675                 680                 685

Lys Asn Gln Val Ser Leu Thr Cys Leu Val Lys Gly Phe Tyr Pro Ser
    690                 695                 700

Asp Ile Ala Val Glu Trp Glu Ser Asn Gly Gln Pro Glu Asn Asn Tyr
705                 710                 715                 720

Lys Thr Thr Pro Pro Val Leu Asp Ser Asp Gly Ser Phe Phe Leu Tyr
                725                 730                 735

Ser Lys Leu Thr Val Asp Lys Ser Arg Trp Gln Gln Gly Asn Val Phe
                740                 745                 750

Ser Cys Ser Val Met His Glu Ala Leu His Asn His Tyr Thr Gln Lys
                755                 760                 765

Ser Leu Ser Leu Ser Pro Gly Lys
                770                 775

<210> SEQ ID NO 19
<211> LENGTH: 16
<212> TYPE: PRT
<213> ORGANISM: Artificial Sequence
<220> FEATURE:
<223> OTHER INFORMATION: Synthetic polymer.

<400> SEQUENCE: 19

Gly Gly Ser Gly Gly Ser Gly Gly Gly Ser Gly Gly Gly Gly Ser
1               5                   10                  15

<210> SEQ ID NO 20
<211> LENGTH: 5
<212> TYPE: PRT
<213> ORGANISM: Artificial Sequence
<220> FEATURE:
<223> OTHER INFORMATION: Synthetic polymer.

<400> SEQUENCE: 20

Gly Gly Gly Gly Ser
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 21

Gly Gly Gly Gly Ser Gly Gly Gly Gly Ser
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Synthetic polymer.

<400> SEQUENCE: 22

Gly Gly Gly Gly Ser Gly Gly Gly Gly Ser Gly Gly Gly Gly Ser
1               5                   10                  15

<210> SEQ ID NO 23
<211> LENGTH: 20
<212> TYPE: PRT
<213> ORGANISM: Artificial Sequence
<220> FEATURE:

```
<223> OTHER INFORMATION: Synthetic polymer.

<400> SEQUENCE: 23

Gly Gly Gly Gly Ser Gly Gly Gly Ser Gly Gly Gly Ser Gly
1               5                   10                  15

Gly Gly Gly Ser
            20

<210> SEQ ID NO 24
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 24

Gly Gly Gly Gly Gly Gly Gly Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic polymer.

<400> SEQUENCE: 25

Gly Gly Gly Gly Gly Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic polymer.

<400> SEQUENCE: 26

Glu Ala Ala Ala Lys
1               5

<210> SEQ ID NO 27
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 27

Glu Ala Ala Ala Lys Glu Ala Ala Ala Lys
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Synthetic polymer.

<400> SEQUENCE: 28

Glu Ala Ala Ala Lys Glu Ala Ala Ala Lys Glu Ala Ala Ala Lys
1               5                   10                  15

<210> SEQ ID NO 29
<211> LENGTH: 12
<212> TYPE: PRT
```

```
<213> ORGANISM: Artificial Sequence
<220> FEATURE:
<223> OTHER INFORMATION: Synthetic polymer.

<400> SEQUENCE: 29

Ala Glu Ala Ala Ala Lys Glu Ala Ala Ala Lys Ala
1               5                   10

<210> SEQ ID NO 30
<211> LENGTH: 17
<212> TYPE: PRT
<213> ORGANISM: Artificial Sequence
<220> FEATURE:
<223> OTHER INFORMATION: Synthetic polymer.

<400> SEQUENCE: 30

Ala Glu Ala Ala Ala Lys Glu Ala Ala Ala Lys Glu Ala Ala Ala Lys
1               5                   10                  15

Ala

<210> SEQ ID NO 31
<211> LENGTH: 22
<212> TYPE: PRT
<213> ORGANISM: Artificial Sequence
<220> FEATURE:
<223> OTHER INFORMATION: Synthetic polymer.

<400> SEQUENCE: 31

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 32
<211> LENGTH: 27
<212> TYPE: PRT
<213> ORGANISM: Artificial Sequence
<220> FEATURE:
<223> OTHER INFORMATION: Synthetic polymer.

<400> SEQUENCE: 32

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 33
<211> LENGTH: 46
<212> TYPE: PRT
<213> ORGANISM: Artificial Sequence
<220> FEATURE:
<223> OTHER INFORMATION: Synthetic polymer.

<400> SEQUENCE: 33

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
                35                  40                  45

<210> SEQ ID NO 34
<211> LENGTH: 5
<212> TYPE: PRT
```

```
<213> ORGANISM: Artificial Sequence
<220> FEATURE:
<223> OTHER INFORMATION: Synthetic polymer.

<400> SEQUENCE: 34

Pro Ala Pro Ala Pro
1               5

<210> SEQ ID NO 35
<211> LENGTH: 18
<212> TYPE: PRT
<213> ORGANISM: Artificial Sequence
<220> FEATURE:
<223> OTHER INFORMATION: Synthetic polymer.

<400> SEQUENCE: 35

Lys Glu Ser Gly Ser Val Ser Ser Glu Gln Leu Ala Gln Phe Arg Ser
1               5                   10                  15

Leu Asp

<210> SEQ ID NO 36
<211> LENGTH: 13
<212> TYPE: PRT
<213> ORGANISM: Artificial Sequence
<220> FEATURE:
<223> OTHER INFORMATION: Synthetic polymer.

<400> SEQUENCE: 36

Glu Gly Lys Ser Ser Gly Ser Gly Ser Glu Ser Lys Ser
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic polymer.

<400> SEQUENCE: 37

Gly Ser Ala Gly Ser Ala Ala Gly Ser Gly Glu Phe
1               5                   10

<210> SEQ ID NO 38
<211> LENGTH: 13
<212> TYPE: DNA
<213> ORGANISM: Artificial Sequence
<220> FEATURE:
<223> OTHER INFORMATION: Synthetic polymer.

<400> SEQUENCE: 38
gccgccacca tgg                                                          13

<210> SEQ ID NO 39
<211> LENGTH: 4
<212> TYPE: DNA
<213> ORGANISM: Artificial Sequence
<220> FEATURE:
<223> OTHER INFORMATION: Synthetic polymer.

<400> SEQUENCE: 39 atgc                                                                     4

<210> SEQ ID NO 40
<211> LENGTH: 4
<212> TYPE: DNA
<213> ORGANISM: Artificial Sequence
```

```
<220> FEATURE:
<223> OTHER INFORMATION: Synthetic polymer.

<400> SEQUENCE: 40 atgg                                                              4

<210> SEQ ID NO 41
<211> LENGTH: 487
<212> TYPE: PRT
<213> ORGANISM: Artificial Sequence
<220> FEATURE:
<223> OTHER INFORMATION: Synthetic polymer.

<400> SEQUENCE: 41
```

Leu Ile Pro Ala Glu Glu Asn Pro Ala Phe Trp Asn Arg Gln Ala
1               5                   10                  15

Ala Gln Ala Leu Asp Val Ala Lys Lys Leu Gln Pro Ile Gln Thr Ala
            20                  25                  30

Ala Lys Asn Val Ile Leu Phe Leu Gly Asp Gly Met Gly Val Pro Thr
        35                  40                  45

Val Thr Ala Thr Arg Ile Leu Lys Gly Gln Met Asn Gly Lys Leu Gly
    50                  55                  60

Pro Glu Thr Pro Leu Ala Met Asp Gln Phe Pro Tyr Val Ala Leu Ser
65                  70                  75                  80

Lys Thr Tyr Asn Val Asp Arg Gln Val Pro Asp Ser Ala Gly Thr Ala
                85                  90                  95

Thr Ala Tyr Leu Cys Gly Val Lys Gly Asn Tyr Arg Thr Ile Gly Val
            100                 105                 110

Ser Ala Ala Ala Arg Tyr Asn Gln Cys Asn Thr Thr Arg Gly Asn Glu
        115                 120                 125

Val Thr Ser Val Ile Asn Arg Ala Lys Lys Ala Gly Lys Ala Val Gly
    130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
                165                 170                 175

Asp Ala Gln Lys Asn Gly Cys Gln Asp Ile Ala Ala Gln Leu Val Tyr
            180                 185                 190

Asn Met Asp Ile Asp Val Ile Leu Gly Gly Gly Arg Met Tyr Met Phe
        195                 200                 205

Pro Glu Gly Thr Pro Asp Pro Glu Tyr Pro Asp Asp Ala Ser Val Asn
    210                 215                 220

Gly Val Arg Lys Asp Lys Gln Asn Leu Val Gln Glu Trp Gln Ala Lys
225                 230                 235                 240

His Gln Gly Ala Gln Tyr Val Trp Asn Arg Thr Ala Leu Leu Gln Ala
                245                 250                 255

Ala Asp Asp Ser Ser Val Thr His Leu Met Gly Leu Phe Glu Pro Ala
            260                 265                 270

Asp Met Lys Tyr Asn Val Gln Gln Asp His Thr Lys Asp Pro Thr Leu
        275                 280                 285

Ala Glu Met Thr Glu Ala Ala Leu Gln Val Leu Ser Arg Asn Pro Arg
    290                 295                 300

Gly Phe Tyr Leu Phe Val Glu Gly Gly Arg Ile Asp His Gly His His
305                 310                 315                 320

Asp Gly Lys Ala Tyr Met Ala Leu Thr Glu Ala Ile Met Phe Asp Asn
                325                 330                 335

```
Ala Ile Ala Lys Ala Asn Glu Leu Thr Ser Glu Leu Asp Thr Leu Ile
            340             345             350

Leu Val Thr Ala Asp His Ser His Val Phe Ser Phe Gly Gly Tyr Thr
        355             360             365

Leu Arg Gly Thr Ser Ile Phe Gly Leu Ala Pro Gly Lys Ala Leu Asp
    370             375             380

Ser Lys Ser Tyr Thr Ser Ile Leu Tyr Gly Asn Gly Pro Gly Tyr Ala
385             390             395             400

Leu Gly Gly Gly Ser Arg Pro Asp Val Asn Gly Ser Thr Ser Glu Glu
                405             410             415

Pro Ser Tyr Arg Gln Gln Ala Ala Val Pro Leu Ala Ser Glu Thr His
            420             425             430

Gly Gly Glu Asp Val Ala Val Phe Ala Arg Gly Pro Gln Ala His Leu
            435             440             445

Val His Gly Val Gln Glu Glu Thr Phe Val Ala His Ile Met Ala Phe
    450             455             460

Ala Gly Cys Val Glu Pro Tyr Thr Asp Cys Asn Leu Pro Ala Pro Ala
465             470             475             480

Thr Ala Thr Ser Ile Pro Asp
            485
```

ALKALINE PHOSPHATE-BASED ONCOLOGY TREATMENTS

CROSS-REFERENCE TO RELATED APPLICATIONS

This application is a 371 national stage filing of International Application No. PCT/US2020/031430, filed May 5, 2020, which claims the benefit of U.S. Provisional Application No. 62/843,850, filed May 6, 2019, the entire contents of which are hereby incorporated by reference in their entirety.

TECHNICAL FIELD

The present invention relates, inter alia, to methods for prevention and/or reduction of chemotherapy-mediated gastrointestinal side effects by administering therapeutic intestinal alkaline phosphatases.

DESCRIPTION OF THE TEXT FILE SUBMITTED ELECTRONICALLY

The content of the text file submitted electronically herewith is incorporated herein by reference in their entirety: A computer readable format copy of the Sequence Listing (Filename: "SYN-046PC_ST25.txt"; Date created: May 4, 2020; File size: 84,284 bytes).

BACKGROUND

Chemotherapy is the common approach to cancer treatment that has been widely used, and various chemotherapeutic agents have been developed for cancer treatment. However, many chemotherapeutic agents have side effects, including moderate to severe side effects, which can include gastrointestinal (GI) distress such as, for example, diarrhea and/or colitis. Some chemotherapeutic agents have been linked to dysbiosis in the intestinal microbiome, which is one of the main causes of intestinal mucositis. The side effects limit the application of chemotherapeutic agents.

Given the need for improved cancer therapies and mitigation of harmful side effects to allow for improved cancer patient care, there is a growing need for therapeutic compositions that prevent and/or reduce the side effects associated with administration of various anticancer agents.

Alkaline phosphatase ("AP," EC 3.1.3.1) is a hydrolase enzyme that can remove phosphate groups from various targets including nucleotides and proteins. Alkaline phosphatases are found in prokaryotic as well as eukaryotic organisms ranging from *E. coli* to mammals. In particular, mammalian APs have been shown to play important roles in gut homeostasis, mucosal barrier function, promotion of commensal bacteria, and defense from pathogens. Mammalian APs exert their properties by primarily targeting LPS (a TLR4 agonist), flagellin (a TLR5 agonist) and CpG DNA (a TLR9 agonist). APs also degrade intestine luminal NTPs (e.g., ATP, GTP, etc.), which promote the growth of good bacteria and reverses dysbiosis. Accordingly, APs may find clinical use in, for example, preventing and/or reducing the side effects associated with administration of anticancer agents.

SUMMARY

Accordingly, the present invention provides methods for using an intestinal alkaline phosphatase (IAP), along with a chemotherapeutic treatment, for treating and/or preventing side effects of the chemotherapeutic treatment.

In some aspects, the present invention provides a method for enhancing the therapeutic efficacy of a chemotherapeutic treatment comprising a nucleoside analog in a subject in need thereof that includes administering to the subject an effective amount of an IAP.

In some aspects of the present invention, a method for treating or preventing at least one side effect of a chemotherapeutic treatment with a nucleoside analog in a subject is provided, comprising administering to the subject an intestinal alkaline phosphatase (IAP), wherein the subject has undergone or is undergoing a treatment of a cancer using the chemotherapeutic treatment.

The IAP can be administered sequentially, simultaneously, or intermittently with the administration of the nucleoside analog. The IAP can be administered orally. In some embodiments, the nucleoside analog can is a purine or pyrimidine analog or derivatives thereof. Non-limiting examples of the nucleoside analog include 5-fluorouracil, 5'-deoxyfluorouridine, 5-fluoro-2'-deoxyuridine triphosphate, fluorouridine, 5-fluoro-2'-deoxycytidine, luoropyrimidine, 2'-deoxyfluorouridine, fluorocytosine, trifluoromethyl-2'-deoxyuridine, cyclocytidine, arabinosyl cytosine, 5-aza-2'-deoxycytidine, arabinosyl-5-azacytosine, azacytidine, 6-azacytidine, N-phosphonoacetyl-L-asparticacid, pyrazofurin, 6-azauridine, azaribine, thymidine, fazarabine, and 3-deazauridine, cytarabine, gemcitabine, troxacitabine, decitabine, pseudoisocytidine, zebularine, ancitabine, capecitabine, N4-octadecyl-cytarabine, elaidic acid-cytarabine, cladribine, acyclovir, clofarabine, nelarabine, forodesine, 8-chloroadenosine, sapacitabine, thiarabine, and derivatives thereof. In embodiments, the nucleoside analog is 5-fluorouracil.

The administration of the IAP does not hinder the treatment of the cancer in the subject in accordance with embodiments of the present disclosure. In some embodiments, administration of the IAP allows reducing a length, dose and/or frequency of administration of the nucleoside analog. For example, in some embodiments, the use of IAP allows using a sub-therapeutic dose of the nucleoside analog. In some embodiments, the method in accordance with the present disclosure increases a therapeutic window of the nucleoside analog.

In some embodiments, administration of an IAP along with a chemotherapeutic treatment, prevents, eliminates, or reduces side effects associated with the chemotherapeutic treatment. Accordingly, in some aspects, the present disclosure provides a method of treating or preventing at least one side effect of a chemotherapeutic treatment with a nucleoside analog in a subject. The method comprises administering to the subject an IAP, wherein the subject has undergone or is undergoing a treatment of a cancer using the chemotherapeutic treatment. The side effect of the chemotherapeutic treatment can include one or more of diarrhea, colitis, mucositis, weight loss, pain, nausea, vomiting, constipation, anemia, malnutrition, alopecia, myelosuppression, renal toxicity, hair loss, numbness, changes in tastes, loss of appetite, thinned or brittle hair, mouth sores, memory loss, hemorrhage, cardiotoxicity, hepatotoxicity, ototoxicity, and post-chemotherapy cognitive impairment. The side effect of the chemotherapeutic treatment can comprise a gastrointestinal (GI) side effect, which can be caused by some chemotherapeutic treatments, such as, for example, nucleoside analogs (e.g., 5-fluorouracil). The method in accordance with the present disclosure allows treating or preventing GI side effects including mucositis and diarrhea.

BRIEF DESCRIPTION OF THE DRAWINGS

FIG. 1A shows assessment of weight change, as mean % of weight change±SEM for untreated (top curve), vehicle+5-FU (middle curve), and SYN BIAPII+5-FU (bottom curve) mice versus a number of days. FIG. 1B shows assessment of stool consistency, as a mean stool consistency score±SEM versus a number of days, of vehicle+5-FU and SYN BIAPII+5-FU mice relative to untreated mice data for which is shown as a baseline at the x-axis. As shown, the administration of 5-FU caused loose stools/diarrhea, and associated weight loss, in all of the treated animals, which peaked at day 6 and recovered by day 9. The administration of IAP shows a significantly faster recovery from the loose stools/diarrhea symptoms ($p<0.03$).

FIG. 2A depicts the mean daily body weight through 50% group survival is displayed as percent change over time compared to body weight at Day 0+SEM. FIG. 2B shows the results of Stool Consistency Scoring daily over Days 0-12; mean scores+SEM are shown. FIG. 2C depicts a graphical representation of the percentage of total animal-days with diarrhea by treatment group.

DETAILED DESCRIPTION

Figure 1A:
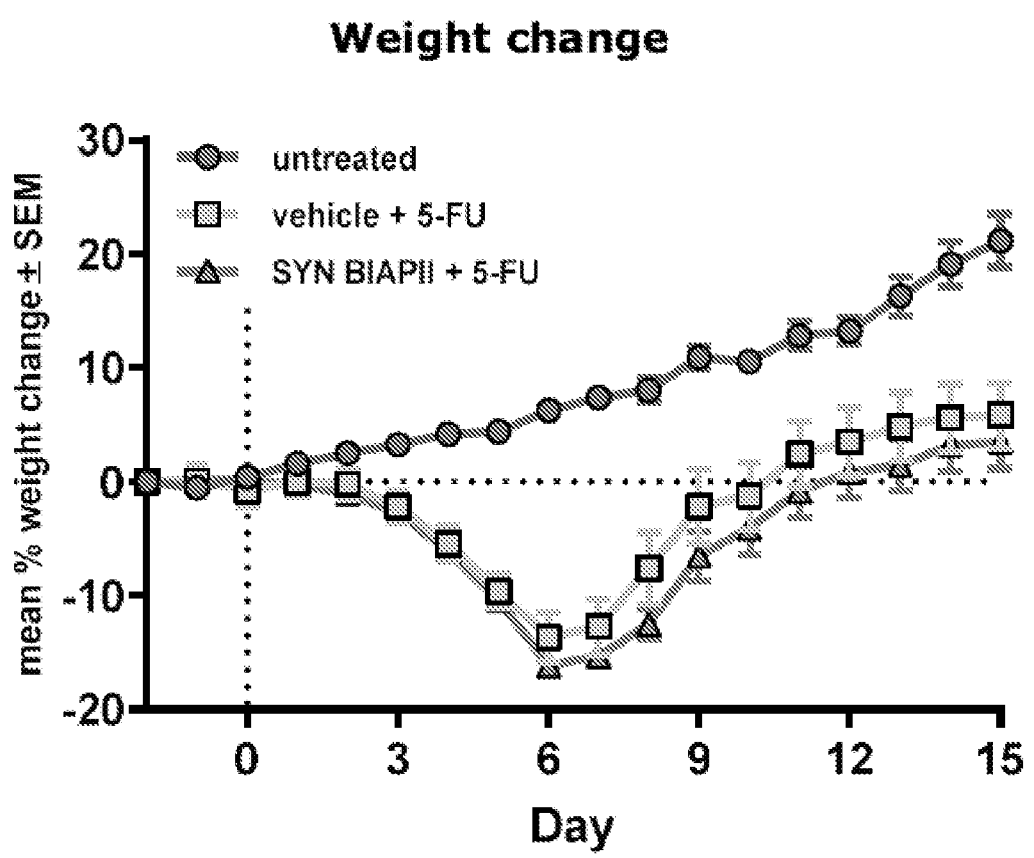
FIGS. 1A and 1B illustrate that administration of IAP reduces side effects of 5-FU.

The present invention is based, inter alia, on the discovery that alkaline phosphatase (AP)-based agents, including without limitation intestinal alkaline phosphatase (IAP), can practically be used in conjunction with anti-cancer treatments that include the use of various chemotherapuetic treatments such as, for example, nucleoside analogs. The inventors have discovered that the use of IAP, which can be administered sequentially, simultaneously, or intermittedly with one or more chemotherapuetic treatments, or in a combination with one of these regimens, does not interfere with the action of the chemotherapeutic agent(s) and, more so, enhances the overall response of a subject to the chemotherapy, based on the discovery that IAP mitigates side effects of cancer treatments such as chemotherapy.

Chemotherapeutic exposure may lead to, for instance, gastrointestinal (GI) tract disruption, including, without limitation, dysbiosis, diarrhea, mucositis, leaky gut, endotoxemia, altered intestinal transit, malabsorption, and dysmotility. The present AP-based agents, including without limitation IAP, optionally orally administered, may reduce or prevent these and other side effects. Accordingly, the present invention relates, in various embodiments, to the treatment or prevention of the effects of chemotherapy with the present AP-based agents, including without limitation IAP, which can be administered orally. The inventors have discovered that IAP finds use in preventing, reducing, or eliminating chemotherapy-mediated GI side effects, such as diarrhea and/or mucositis colitis, in patients. Such use of IAP, as mentioned above, allows for more efficacious cancer treatment, as chemotherapy is not limited by dose- and regimen-limiting GI and other side effects.

Chemotherapuetic treatments involve use of various agents, including, without limitation, nucleoside analogs that are a class of antimetabolites widely used in the treatment of various malignancies, including blood cancers and solid tumors. The nucleoside analogs mimic physiological nucleosides and are incorporated into newly synthesized DNA, resulting in synthesis inhibition and chain termination. Some of the nucleoside analogs inhibit key enzymes involved in the generation of the purine and pyrimidine nucleotides and RNA synthesis, and directly activate the caspase cascade. The effects of the action of nucleoside analogs may lead to cell death. Non-limiting examples of the nucleoside analog include 5-fluorouracil, 5'-deoxyfluorouridine, 5-fluoro-2'-deoxyuridine triphosphate, fluorouridine, 5-fluoro-2'-deoxycytidine, luoropyrimidine, 2'-deoxyfluorouridine, fluorocytosine, trifluoro-methyl-2'-deoxyuridine, cyclocytidine, arabinosyl cytosine, 5-aza-2'-deoxycytidine, arabinosyl-5-azacytosine, azacytidine, 6-azacytidine, N-phosphonoacetyl-L-asparticacid, pyrazofurin, 6-azauridine, azaribine, thymidine, fazarabine, and 3-deazauridine, cytarabine, gemcitabine, troxacitabine, decitabine, pseudoisocytidine, zebularine, ancitabine, capecitabine, N4-octadecyl-cytarabine, elaidic acid-cytarabine, cladribine, acyclovir, clofarabine, nelarabine, forodesine, 8-chloroadenosine, sapacitabine, thiarabine, and derivatives thereof.

Most nucleoside analogs may cause potentially harmful side effects that include, but are not limited to, diarrhea and/mucositis. Other examples of side effects of a chemotherapeutic treatment with one or more nucleoside analogs comprise diarrhea, colitis, mucositis, weight loss, pain, nausea, vomiting, constipation, anemia, malnutrition, alopecia, myelosuppression, renal toxicity, hair loss, numbness, changes in tastes, loss of appetite, thinned or brittle hair, mouth sores, memory loss, hemorrhage, cardiotoxicity, hepatotoxicity, ototoxicity, and post-chemotherapy cognitive impairment.

IAP is an endogenous protein expressed by the intestinal epithelium that promotes GI homeostasis by detoxifying inflammatory mediators, and can be used to mitigate inflammation, tighten the gut barrier, and maintain gut homeostasis by promoting a healthy microbiome. For example, loss of IAP expression or function is associated with increased intestinal inflammation, dysbiosis, bacterial translocation, and systemic inflammation.

Its primary functions, among others, in maintaining intestinal homeostasis are generally recognized as the regulation of bicarbonate secretion and duodenal surface pH, long chain fatty acid absorption, mitigation of intestinal inflammation through detoxification of pathogen-associated molecular patterns, and regulation of the gut microbiome. Several substrates that are acted on by IAP's phosphatase functions include, without wishing to be bound by theory, lipopolysaccharide (LPS), flagellin, CpG DNA, and nucleotide di- and tri-phosphates. Specifically, IAP is a target for therapeutics due to its ability to downregulate inflammation, regulate the microbiome, tighten the gut barrier through enhanced expression of claudins and occludins, and affect metabolism of adenosine tri-phosphate and diphosphate (ATP and ADP). The present invention contemplates a composition comprising IAP that does not hinder cancer treatment to the patient. In fact, according to the present invention, the methods described herein enhance the overall response of a subject to a chemotherapeutic treatment with a nucleoside analog.

Accordingly, the present invention is directed, in part, to a method for treating or preventing at least one side effect of a chemotherapeutic treatment with a nucleoside analog in a subject in need thereof, comprising administering to the subject an IAP, wherein the subject has undergone or is undergoing a treatment of a cancer using the chemotherapeutic treatment.

Alkaline Phosphatases (APs)

The present disclosure is directed, in part, to pharmaceutical compositions, formulations, and uses of one or more alkaline phosphatase-based agents (AP-based agents). Alkaline phosphatases are dimeric metalloenzymes that catalyze the hydrolysis of phosphate esters and dephosphorylate a variety of target substrates at physiological and higher pHs. Illustrative APs that may be utilized in the present invention include, but are not limited to, IAP (e.g., calf IAP or bovine IAP, chicken IAP, goat IAP), placental alkaline phosphatase (PLAP), placental-like alkaline phosphatase, germ cell alkaline phosphatase (GCAP), tissue non-specific alkaline phosphatase (TNAP; which is primarily found in the liver, kidney, and bone), bone alkaline phosphatase, liver alkaline phosphatase, kidney alkaline phosphatase, bacterial alkaline phosphatase, fungal alkaline phosphatase, shrimp alkaline phosphatase, modified IAP, recombinant IAP, or any polypeptide comprising alkaline phosphatase activity.

In various embodiments, the present invention contemplates the use of mammalian alkaline phosphatases including, but not limited to, IAP, placental alkaline phosphatase (PLAP), germ cell alkaline phosphatase (GCAP), and the tissue non-specific alkaline phosphatase (TNAP).

In some embodiments, the AP-based agent is IAP. IAP is produced in the proximal small intestine and it bound to the enterocytes via a GPI anchor. Some IAP is released into the intestinal lumen in conjunction with vesicles shed by the cells and as soluble protein stripped from the cells via phospholipases. The enzyme then traverses the small and large intestine such that some active enzyme can be detected in the feces. In an embodiment, the IAP is human IAP (hIAP). In an embodiment, the IAP is calf IAP (cIAP), also known as bovine IAP (bIAP). There are multiple isozymes of bIAP, for example, with bIAP II and IV having higher specific activity than bIAP I. In an embodiment, the IAP is any one of the cIAP or bIAP isozymes (e.g., bIAP I, II, and IV). In an embodiment, the IAP is bIAP II. In another embodiment, the IAP is bIAP IV.

Also included within the definition of IAPs are IAP variants. An IAP variant has at least one or more amino acid modifications, generally amino acid substitutions, as compared to the parental wild-type sequence. In some embodiments, an IAP of the invention comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein. In addition, IAP variants retain most or all of their biochemical activity, measured as described herein.

In various embodiments, the AP-based agent is hIAP or a variant thereof. In some embodiments, the AP-based agent is hIAP comprising the amino acid sequence of SEQ ID NO: 1 as depicted below.

HIAP

```
                                    SEQ ID NO: 1
  1 mqgpwvllll glrlqlslgy ipaeeenpaf wnrqaaeald
    aakklqpiqk vaknlilflg 61 dglgyptvta trilkgqkng klgpetplam drfpylalsk
    tynydrqvpd saatataylc
```

-continued
```
121 gvkanfqtig lsaaarfnqc nttrgnevis vmnrakqagk
    svgvvtttrv qhaspagtya 181 htvnrnwysd admpasarqe gcqdiatqli snmdidvilg
    ggrkymfpmg tpdpeypada 241 sqngirldgk nlyqewlakh qgawyvwnrt elmqasldqs
    vthlmglfep gdtkyeihrd 301 ptldpslmem teaalrllsr nprgfylfve ggridhghhe
    gvayqaltea vmfddaiera 361 gqltseedtl tlytadhshv fsfggytlrg ssifglapsk
    aqdskaytsi lygngpgyvf 421 nsgyrpdyne sesgspdyqq qaavplsset hggedvavfa
    rgpqahlvhg vqeqsfvahv 481 mafaaclepy tacdlappac ttdaahpvaa slpllagtll
    llgasaap
```

Without wishing to be bound by theory, it is believed that a cysteine at the carboxy terminus of the AP-based agent (e.g., at position 500 of SEQ ID NO: 1) may interfere with protein folding. Accordingly, in some embodiments, the AP-based agent includes a mutation of the cysteine (e.g., at position 500 of SEQ ID NO: 1). In some embodiments, the cysteine is replaced with glycine.

In various embodiments, the AP-based agent is bIAP II or a variant thereof. In an embodiment, the bIAP II comprises the signal peptide and carboxy terminus of bIAP I. In an embodiment, the bIAP II comprises an aspartate and position 248 (similar to bIAP IV). In an embodiment, the bIAP II comprises the amino acid sequence of SEQ ID NO: 2:

```
BIAP 11 with 248D assignment.
The signal peptide and sequence past 480 are
derived from blAP I
                                    SEQ ID NO: 2
  1 mqgacvllll glhlqlslgl ipaeeenpaf wnrgaagald
    vakklqpiqt aaknvilflg 61 dgmgvptvta trilkgqmng klgpetplam dqfpyvalsk
    tynvdrqvpd sagtataylc 121 gvkgnyrtig vsaaarynqc nttrgnevts vinrakkagk
    avgvvtttry qhaspagaya 181 htvnrnwysd adlpadaqkn gcgdiaaglv ynmdidvilg
    ggrmymfpeg tpdpeypdda 241 svngvrkdkq nlvqewqakh qgagyvwnrt allqaaddss
    vthlmglfep admkynvqqd 301 htkdptlaem teaalqvlsr nprgfylfve ggridhghhd
    gkaymaltea imfdnaiaka 361 neltseldtl ilvtadhshv fsfggytlrg tsifglapgk
    aldsksytsi lygngpgyal 421 gggsrpdvng stseepsyrq qaavplaset hggedvavfa
    rgpqahlvhg vqeetfvahi 481 mafagcvepy tdcnlpapat atsipdaahl aasppplall
    agamllllap tly
```

In various embodiments, the bIAP II comprises the amino acid sequence of SEQ ID NO: 41.

BIAP II with stop codon and no leader sequence
(SYN-020) (SEQ ID NO: 41):
LIPAEEENPAFWNRQAAQALDVAKKLQPIQTAAKNVILFLGDGMGVPTVT

ATRILKGQMNGKLGPETPLAMDQFPYVALSKTYNVDRQVPDSAGTATAYL

-continued

```
CGVKGNYRTIGVSAAARYNQCNTTRGNEVTSVINRAKKAGKAVGVVTTTR

VQHASPAGAYAHTVNRNWYSDADLPADAQKNGCQDIAAQLVYNMDIDVIL

GGGRMYMFPEGTPDPEYPDDASVNGVRKDKQNLVQEWQAKHQGAQYVWNR

TALLQAADDSSVTHLMGLFEPADMKYNVQQDHTKDPTLAEMTEAALQVLS

RNPRGFYLFVEGGRIDHGHHDGKAYMALTEAIMFDNAIAKANELTSELDT

LILVTADHSHVFSFGGYTLRGTSIFGLAPGKALDSKSYTSILYGNGPGYA

LGGGSRPDVNGSTSEEPSYRQQAAVPLASETHGGEDVAVFARGPQAHLVH

GVQEETFVAHIMAFAGCVEPYTDCNLPAPATATSIPD
```

In various embodiments, the AP-based agent is bIAP IV or a variant thereof. In an embodiment, the bIAP IV comprises the amino acid sequence of SEQ ID NO: 3:

```
BIAP IV
                                             SEQ ID NO: 3
   1  mgwacvllll  glwlqlsltf  ipaeeedpaf  wnrgaagald
      vakklqpiqt  aaknvilflg 61  dgmgvptvta  trilkgqmng  klgpetplam  dqfpyvalsk
      tynvdrqvpd  sagtataylc 121  gvkgnyktig  vsaaarynqc  nttsgnevts  vmnrakkagk
      svgvvttsrv  qhaspagaya 181  htvnrnwysd  adlpadaqty  gcqdiatqlv  nnmdidvilg
      ggrmymfpeg  tpdpeypydv 241  nqtgvrkdkr  nlvqewqakh  qgagyvwnrt  ellqaandps
      vthlmglfep  admkynvqqd 301  ptkdptleem  teaalqvlsr  npqgfylfve  ggridhghhe
      gkaymaltdt  vmfdnaiaka 361  neltseldtl  ilatadhshv  fsfggytlrg  tsifglapsk
      asdnksytsi  lygngpgyvl 421  ggglrpdvnd  sisedpsyrq  qaavplsses  hggedvavfa
      rgpqahlvhg  vqeetfvahv 481  mafagcvepy  tdcnlpapsg  lsdaahlaas  ppslallaga
      mlllapaly
```

Mammalian alkaline phosphatases are glycosylphosphatidyl-inositol (GPI) anchored proteins. They have signal peptides and are translated into the secretory pathway. Once in the endoplasmic reticulum (ER), the proteins are glycosylated and folded. There are two disulfide bonds as well as a single free cysteine that is apparently not accessible on the surface. In the late ER, the carboxy terminus is removed and the GPI anchor is appended. GPI anchoring is therefore a process that occurs at the carboxy terminus of the alkaline phosphatase. The inclusion of stop codons at the anchor site enables secretion of biologically active protein (presumably the homodimer). While there is no consensus sequence, the carboxy terminus includes three amino acids, termed omega, omega +1, and omega +2 which are followed by a short stretch of hydrophilic amino acids and then a stretch of hydrophobic amino acids. Without wishing to be bound by theory, it is believed that the hydrophobicity is critical for embedding the carboxy terminus in the ER membrane. Then an enzymatic reaction replaces the carboxy terminus with the GPI anchor.

Within hPLAP, the GPI anchor is attached at an aspartate in the sequence, DAAH. Similarly, hIAP, bIAP II, and bIAP IV also have this DAAH sequence conserved, potentially serving as the GPI anchor site. Mutational studies with hPLA indicate that preventing GPI anchoring results in intracellular retention. In addition, mutations around the anchor site or in the hydrophobic domain either 1) prevent anchor attachment leading to intracellular retention or 2) do not block anchor attachment. Without wishing to be bound by theory, it is believed that the hydrophobic domain serves as a signal for GPI anchor attachment. Truncating or eliminating the hydrophobic domain leads to secretion. Finally, there is a single mutation in the hydrophobic domain that, in hPLAP, enables secretion of a protein with its hydrophobic domain intact.

In various embodiments, the AP-based agent of the invention is GPI anchored to a host cell. For example, the AP-based agent may be GPI anchored to the cell membrane of the host cell. In other embodiments, the AP-based agent of the invention is a secreted rather than an anchored protein. In some embodiments, the AP-based agent is not GPI anchored. In some embodiments, the AP-based agent may lack the GPI anchor site. In some embodiments, the AP-based agent comprises a stop codon that is inserted immediately after the GPI anchor site. In an embodiment, the AP-based agent comprises a stop codon after the aspartate in the DAAH consensus site (e.g., at amino acid 503 of hIAP and bIAP IV or amino acid 506 of bIAP II).

```
HIAP with stop codon
                                             (SEQ ID NO: 4)
   1  mqgpwvllll  glrlqlslgv  ipaeeenpaf  wnrqaaeald
      aakklqpiqk  vaknlilflg 61  dglgvptvta  trilkgqkng  klgpetplam  drfpylalsk
      tynvdrqvpd  saatataylc 121  gvkanfqtig  lsaaarfnqc  nttrgnevis  vmnrakqagk
      svgvvtttrv  qhaspagtya 181  htvnrnwysd  admpasarqe  gcqdiatqli  snmdidvilg
      ggrkymfpmg  tpdpeypada 241  sqngirldgk  nlvqewlakh  qgawyvwnrt  elmqasldqs
      vthlmglfep  gdtkyeihrd 301  ptldpslmem  teaalrllsr  nprgfylfve  ggridhghhe
      gvayqaltea  vmfddaiera 361  gqltseedtl  tlvtadhshv  fsfggytlrg  ssifglapsk
      aqdskaytsi  lygngpgyvf 421  nsgvrpdvne  sesgspdyqq  qaavplsset  hggedvavfa
      rgpqahlvhg  vqeqsfvahv 481  mafaaclepy  tacdlappag  ttd BIAP II with stop codon
                                             (SEQ ID NO: 5)
   1  mqgacvllll  glhlqlslgl  ipaeeenpaf  wnrqaaqald
      vakklqpiqt  aaknvilflg 61  dgmgvptvta  trilkgqmng  klgpetplam  dqfpyvalsk
      tynvdrqvpd  sagtataylc 121  gvkgnyrtig  vsaaarynqc  nttrgnevts  vinrakkagk
      avgvvtttrv  qhaspagaya 181  htvnrnwysd  adlpadaqkn  gcqdiaaqlv  ynmdidvilg
      ggrmymfpeg  tpdpeypdda 241  svngvrkdkq  nlvqewqakh  qgaqyvwnrt  allqaaddss
      vthlmglfep  admkynvqqd 301  htkdptlaem  teaalqvlsr  nprgfylfve  ggridhghhd
      gkaymaltea  imfdnaiaka 361  neltseldtl  ilvtadhshv  fsfggytlrg  tsifglapgk
      aldsksytsi  lygngpgyal
```

```
421  gggsrpdvng  stseepsyrq  qaavplaset  hggedvavfa
     rgpqahlvhg  vqeetfvahi 481  mafagcvepy  tdcnlpapat  atsipd BIAP IV with stop codon
                                        (SEQ ID NO: 6)
  1  mqwacvllll  glwlqlsltf  ipaeeedpaf  wnrqaaqald
     vakklqpiqt  aaknvilflg 61  dgmgvptvta  trilkgqmng  klgpetplam  dqfpyvalsk
     tynvdrqvpd  sagtataylc 121  gvkgnyktig  vsaaarynqc  nttsgnevts  vmnrakkagk
     svgvvttsry  qhaspagaya 181  htvnrnwysd  adlpadaqty  gcqdiatqlv  nnmdidvilg
     ggrmymfpeg  tpdpeypydv 241  nqtgvrkdkr  nlvqewqakh  qgaqyvwnrt  ellqaandps
     vthlmglfep  admkynvqqd 301  ptkdptleem  teaalqvlsr  npqgfylfve  ggridhghhe
     gkaymaltdt  vmfdnaiaka 361  neltseldtl  ilatadhshv  fsfggytlrg  tsifglapsk
     asdnksytsi  lygngpgyvl 421  ggglrpdvnd  sisedpsyrq  qaavplsses  hggedvavfa
     rgpqahlvhg  vqeetfvahv 481  mafagcvepy  tdcnlpapsg  lsd
```

In an embodiment, the AP-based agent is bIAP IV and includes a stop codon after amino acid 508 to mimic a secreted PLAP construct as depicted below:

```
BIAP IV with stop codon after amino acid 508
                                        (SEQ ID NO: 7)
  1  mgwacvllll  glwlqlsltf  ipaeeedpaf  wnrqaagald
     vakklqpiqt  aaknvilflg 61  dgmgvptvta  trilkgqmng  klgpetplam  dqfpyvalsk
     tynvdrqvpd  sagtataylc 121  gvkgnyktig  vsaaarynqc  nttsgnevts  vmnrakkagk
     svgvvttsry  qhaspagaya 181  htvnrnwysd  adlpadaqty  gcqdiatqlv  nnmdidvilg
     ggrmymfpeg  tpdpeypydv 241  nqtgvrkdkr  nlvqewqakh  qgagyvwnrt  ellqaandps
     vthlmglfep  admkynvqqd 301  ptkdptleem  teaalqvlsr  npqgfylfve  ggridhghhe
     gkaymaltdt  vmfdnaiaka 361  neltseldtl  ilatadhshv  fsfggytlrg  tsifglapsk
     asdnksytsi  lygngpgyvl 421  ggglrpdynd  sisedpsyrq  qaavplsses  hggedvavfa
     rgpqahlvhg  vqeetfyahv 481  mafagcvepy  tdcnlpapsg  lsdaahla
```

In various embodiments, the AP-based agent of the invention is a fusion protein. In some embodiments, the AP-based agent comprises an alkaline phosphatase fused to a protein domain that replaces the GPI anchor sequence. In some embodiments, the alkaline phosphatase is fused to a protein domain that promotes protein folding and/or protein purification and/or protein dimerization and/or protein stability. In various embodiments, the AP-based agent fusion protein has an extended serum half-life.

In an embodiment, the alkaline phosphatase is fused to an immunoglobulin Fc domain and/or hinge region. In various embodiments, the immunoglobulin Fc domain and/or hinge region is derived from the Fc domain and/or hinge region of an antibody (e.g., of IgG, IgA, IgD, and IgE, inclusive of subclasses (e.g. IgG1, IgG2, IgG3, and IgG4, and IgA1 and IgA2)). In an embodiment, the AP-based agent of the invention comprises an alkaline phosphatase fused to the hinge region and/or Fc domain of IgG.

In various embodiments, the AP-based agent is fused to a Fc domain of IgG comprising one or more mutations. In some embodiments, the one or more mutations in the Fc domain of IgG function to increase serum half-life and longevity. In some embodiments, the Fc domain of IgG comprises one or more mutations at amino acid residues 251-256, 285-290, 308-314, 385-389 and 428-436, numbered according to the EU index as in Kabat (see Kabat et al., (1991) Sequences of Proteins of Immunological Interest, U.S. Public Health Service, National Institutes of Health, Washington, DC). In some embodiments, at least one of the amino acid substitutions is at amino acid residue 252, 254, 256, 309, 311, 433 or 434. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In some embodiments, the Fc domain of IgG comprises one or more mutations at amino acid residue 252, 254, 256, 433, 434, or 436. In an embodiment, the Fc domain of IgG includes a triple M252Y/S254T/T256E mutation or YTE mutation. In another embodiment, the Fc domain of IgG includes a triple H433K/N434F/Y436H mutation or KFH mutation. In a further embodiment, the Fc domain of IgG includes a YTE and KFH mutation in combination.

In some embodiments, the Fc domain of IgG contains one or more mutations at amino acid residues 250, 253, 307, 310, 380, 428, 433, 434, and 435. Exemplary mutations include T250Q, M428L, T307A, E380A, I253A, H310A, M428L, H433K, N434A, N434F, N434S, and H435A. In an embodiment, the Fc domain of IgG comprises a M428L/N434S mutation or LS mutation. In another embodiment, the Fc domain of IgG comprises a T250Q/M428L mutation or QL mutation. In another embodiment, the Fc domain of IgG comprises an N434A mutation. In another embodiment, the Fc domain of IgG comprises a T307A/E380A/N434A mutation or AAA mutation. In another embodiment, the Fc domain of IgG comprises an I253A/H310A/H435A mutation or IHH mutation. In another embodiment, the Fc domain of IgG comprises a H433K/N434F mutation. In another embodiment, the Fc domain of IgG region comprises a M252Y/S254T/T256E and a H433K/N434F mutation in combination.

Exemplary mutations in the Fc domain of IgG are described, for example, in Robbie, et al., Antimicrobial Agents and Chemotherapy (2013), 57(12):6147-6153, Dall'Acqua et al., JBC (2006), 281(33):23514-24, Dall'Acqua et al., Journal of Immunology (2002), 169:5171-80, Ko et al. Nature (2014) 514:642-645, Grevys et al Journal of Immunology. (2015), 194(11):5497-508, and U.S. Pat. No. 7,083,784, the entire contents of which are hereby incorporated by reference.

In various embodiments, the one or more mutations in the Fc domain of IgG increases affinity for the neonatal Fc receptor (FcRn). In some embodiments, the one or more mutations in the Fc domain of IgG increases affinity for FcRn at a pH of about 6.0, about 6.1, about 6.2, about 6.3, about 6.4, or about 6.5.

In various embodiments, the alkaline phosphatase is fused to one or more of PEG, XTENylation (e.g., as rPEG), polysialic acid (POLYXEN), albumin, elastin-like protein, elastin like protein (ELP), PAS, HAP, GLK, CTP, and transferrin. In various embodiments, the alkaline phosphatase is fused to one or more of the agents described in BioDrugs (2015) 29:215-239, the entire contents of which are hereby incorporated by reference.

In an embodiment, the alkaline phosphatase is fused to a protein domain (e.g., an immunoglobulin Fc domain) via a linker to the GPI anchor site. For example, the alkaline phosphatase may be fused to a protein domain via the aspartate at the GPI anchor sequence. The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present AP-based agent. In another example, the linker may function to target the AP-based agent to a particular cell type or location.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). In an embodiment, the linker sequence is GGSGGSGGGGSGGGGS (SEQ ID NO: 19). Additional illustrative linkers include, but are not limited to, linkers having the sequence LE, GGGGS (SEQ ID NO: 20), $(GGGGS)_n$ (n=2-4) (SEQ ID NO: 21-23), $(Gly)_8$ (SEQ ID NO: 24), $(Gly)_6$ (SEQ ID NO: 25), $(EAAAK)_n$ (n=1-3) ((SEQ ID NO: 26-28), $A(EAAAK)_nA$ (n=2-5) (SEQ ID NO: 29-32), AEAAAKEAAAKA (SEQ ID NO: 30), $A(EAAAK)_4ALEA(EAAAK)_4A$ (SEQ ID NO: 33), PAPAP (SEQ ID NO: 34), KESGSVSSEQLAQFRSLD (SEQ ID NO: 35), EGKSSGSGSESKST (SEQ ID NO: 36), GSAGSAAGSGEF (SEQ ID NO: 37), and $(XP)_n$, with X designating any amino acid, e.g., Ala, Lys, or Glu. In various embodiments, the linker is GGS.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

According to crystallographic studies, the immunoglobulin hinge region can be further subdivided functionally into three regions: the upper hinge region, the core region, and the lower hinge region. See Shin et al., 1992 *Immunological Reviews* 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. The core hinge region of wild-type human IgG1 contains the sequence Cys-Pro-Pro-Cys which, when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin.

In various embodiments, the linker of the present invention comprises one or more glycosylation sites.

In some embodiments, the linker is a synthetic linker such as PEG.

Illustrative Fc Fusion Constructs of the Invention Include:

```
BIAP II with Fc Fusion - Fc domain is underlined
                                                            (SEQ ID NO: 8)
   1 mqgacvllll glhlqlslgl ipaeeenpaf wnrqaaqald vakklqpiqt aaknvilflg
  61 dgmgvptvta trilkgqmng klgpetplam dqfpyvalsk tynvdrqvpd sagtataylc
 121 gvkgnyrtig vsaaarynqc nttrgnevts vinrakkagk avgvvtttry qhaspagaya
 181 htvnrnwysd adlpadaqkn gcgdiaaglv ynmdidvilg ggrmymfpeg tpdpeypdda
 241 svngvrkdkq nlvqewqakh qgagyvwnrt allqaaddss vthlmglfep admkynvqqd
 301 htkdptlaem teaalqvlsr nprgfylfve ggridhghhd gkaymaltea imfdnaiaka
 361 neltseldtl ilvtadhshv fsfggytlrg tsifglapgk aldsksytsi lygngpgyal
 421 gggsrpdvng stseepsyrq qaavplaset hggedvavfa rgpqahlvhg vqeetfvahi
 481 mafagcvepy tdcnlpapat atsipdGGSGGSGGGGSGGGGSEPKSCDKTHTCPPCPAPE
     LLGGPSVFLFPPKPKDTLMI SRTPEVTCVVVDVSHEDPQV KFNWYVDGVQVHNAKTKPRE
     QQYNSTYRVVSVLTVLHQNW LDGKEYKCKVSNKALPAPIE KTISKAKGQPREPQVYTLPP
     SREEMTKNQVSLTCLVKGFY PSDIAVEWESNGQPENNYKT TPPVLDSDGSFFLYSKLTVD
     KSRWQQGNVFSCSVMHEALH NHYTQKSLSLSPGK BIAP IV with Fc Fusion - Fc domain is underlined
                                                            (SEQ ID NO: 9)
   1 mgwacvllll glwlqlsltf ipaeeedpaf wnrgaagald vakklqpiqt aaknvilflg
  61 dgmgvptvta trilkgqmng klgpetplam dqfpyvalsk tynvdrqvpd sagtataylc
 121 gvkgnyktig vsaaarynqc nttsgnevts vmnrakkagk svgvvttsry qhaspagaya
 181 htvnrnwysd adlpadaqty gcqdiatqlv nnmdidvilg ggrmymfpeg tpdpeypydv
 241 nqtgvrkdkr nlvqewqakh qgagyvwnrt ellqaandps vthlmglfep admkynvqqd
 301 ptkdptleem teaalqvlsr npqgfylfve ggridhghhe gkaymaltdt vmfdnaiaka
 361 neltseldtl ilatadhshv fsfggytlrg tsifglapsk asdnksytsi lygngpgyvl
 421 ggglrpdynd sisedpsyrq qaavplsses hggedvavfa rgpqahlvhg vqeetfyahv
 481 mafagcvepy tdcnlpapsg lsdGGSGGSGGGGSGGGGSEPKSCDKTHTCPPCPAPE
     LLGGPSVFLFPPKPKDTLMI SRTPEVTCVVVDVSHEDPQV KFNWYVDGVQVHNAKTKPRE
     QQYNSTYRVVSVLTVLHQNW LDGKEYKCKVSNKALPAPIE KTISKAKGQPREPQVYTLPP
     SREEMTKNQVSLTCLVKGFY PSDIAVEWESNGQPENNYKT TPPVLDSDGSFFLYSKLTVD
     KSRWQQGNVFSCSVMHEALH NHYTQKSLSLSPGK HIAP with Fc Fusion - Fc domain is underlined:
                                                             SEQ ID NO: 18
   1 mqgpwvllll glrlqlslgy ipaeeenpaf wnrqaaeald aakklqpiqk vaknlilflg
  61 dglgyptvta trilkgqkng klgpetplam drfpylalsk tynydrqvpd saatataylc
 121 gvkanfqtig lsaaarfnqc nttrgnevis ymnrakgagk svgyytttry qhaspagtya
 181 htvnrnwysd admpasarqe gcgdiatqli snmdidvilg ggrkymfpmg tpdpeypada
 241 sqngirldgk nlygewlakh qgawyywnrt elmgasldqs vthlmglfep gdtkyeihrd
 301 ptldpslmem teaalrllsr nprgfylfve ggridhghhe gvaygaltea vmfddaiera
 361 gqltseedtl tlytadhshy fsfggytlrg ssifglapsk aqdskaytsi lygngpgyvf
 421 nsgyrpdyne sesgspdygq qaavplsset hggedvavfa rgpqahlvhg vqeqsfvahv
 481 mafaaclepy tacdlappac ttdaahpvaa slpllagtll llgasaap
     GGSGGSGGGGSGGGGSEPKSCDKTHTCPPCPAPE LLGGPSVFLFPPKPKDTLMI
     SRTPEVTCVVVDVSHEDPQV KFNWYVDGVQVHNAKTKPRE QQYNSTYRVVSVLTVLHQNW
     LDGKEYKCKVSNKALPAPIE KTISKAKGQPREPQVYTLPP SREEMTKNQVSLTCLVKGFY
```

-continued

PSDIAVEWESNGQPENNYKT TPPVLDSDGSFFLYSKLTVD KSRWQQGNVFSCSVMHEALH
NHYTQKSLSLSPGK

In various embodiments, the linker can be substituted with any other linker disclosed herein.

A *Saccharomyces* alkaline phosphatase, Pho8, is produced as an inactive pro-enzyme. It is not GPI anchored, but is a transmembrane protein with its amino terminus extending out of a lysosome into the cytoplasm. Within the lysosome, an enzyme, PEP4, cleaves the carboxy terminus to activate the enzyme. Without wishing to be bound by theory, it is believed that mammalian alkaline phosphatases may also be generated as inactive pro-enzymes. This is because alkaline phosphatases can dephosphorylate ATP, so that activity in the ER could drain the ER of its major energy source. Without wishing to be bound by theory, it is believed that the inhibitory function is located to the carboxy terminus that would be relieved upon GPI anchor addition. Alternatively, other activities such as folding or metal (Zn or Mg) inclusion could control activity.

In various embodiments, the AP-based agent of the invention is a pro-enzyme. In an embodiment, the activity of the proenzyme is suppressed by a carboxy terminus. In an embodiment, protease removal of the carboxy terminus reactivates the enzymatic activity of the alkaline phosphatase. In an embodiment, the pro-enzyme is more efficiently secreted than the enzyme without the carboxy terminus.

In some embodiments, for generation of the pro-enzyme, the native carboxy terminus of the alkaline phosphatase is replaced with the analogous sequence from hPLAP. In some embodiments, a mutation is made in the hydrophobic carboxy tail to promote protein secretion without cleavage of the carboxy terminus. In an illustrative embodiment, a single point mutation such as a substitution of leucine with e.g., arginine is generated in the hydrophobic carboxy terminus (e.g. allpllagtl is changed to e.g., allplragtl) to result in secretion of the enzyme without removal of the carboxy terminus.

In an embodiment, the AP-based agent is altered to include a specific enzyme cleavage site which allows subsequent removal of the carboxy terminus. In an embodiment, the AP-based agent includes a protease cleavage site. Illustrative protease cleavage sites include, but are not limited to, cleavage sites recognized by furin, Rhinovirus 16 3C protease, factor Xa protease, trpysin, chymotrypsin, elastase, pepsin, papain subtilisin, thermolysin, V-8 protease, submaxillaris protease, clostripain, thrombin, collagenase, and any other endoproteases. In an alternative embodiment, the AP-based agent includes a cleavage site recognized by a digestive enzyme present in the GI tract. In such embodiments, the AP-based agent may be administered as a prodrug that is subsequently activated in the GI tract.

In an illustrative embodiment, the proenzyme is a proenzyme of bIAP IV having the following sequences:

BIAP IV with the hPLAP Carboxy Terminus and Mutation for Unprocessed Secretion and RV3C Cleavage (at . . . LEVLFQGP . . . ):

SEQ ID NO: 10

```
  1 mqwacvllll glwlqlsltf ipaeeedpaf wnrqaaqald
    vakklqpiqt aaknvilflg 61 dgmgvptvta trilkgqmng klgpetplam dqfpyvalsk
    tynvdrqvpd sagtataylc
```

-continued

```
121 gvkgnyktig vsaaarynqc nttsgnevts vmnrakkagk
    svgvvttsrv qhaspagaya 181 htvnrnwysd adlpadaqty gcqdiatqlv nnmdidvilg
    ggrmymfpeg tpdpeypydv 241 nqtgvrkdkr nlvqewqakh qgagyvwnrt ellqaandps
    vthlmglfep admkynvqqd 301 ptkdptleem teaalqvlsr npqgfylfve ggridhghhe
    gkaymaltdt vmfdnaiaka 361 neltseldtl ilatadhshv fsfggytlrg tsifglapsk
    asdnksytsi lygngpgyvl 421 ggglrpdvnd sisedpsyrq qaavplsses hggedvavfa
    rgpqahlvhg vqeetfvahv 481 mafagcvepy tdcnlevlfq gpappagttd aahpgrsvvp
    allplragtl llletatap
```

BIAP IV with hPLAP Carboxy Terminus and Mutation for Unprocessed Secretion and FXa Cleavage (at . . . IEGR . . . ):

SEQ ID NO: 11

```
  1 mqwacvllll glwlqlsltf ipaeeedpaf wnrqaaqald
    vakklqpiqt aaknvilflg 61 dgmgvptvta trilkgqmng klgpetplam dqfpyvalsk
    tynvdrqvpd sagtataylc 121 gvkgnyktig vsaaarynqc nttsgnevts vmnrakkagk
    svgvvttsry qhaspagaya 181 htvnrnwysd adlpadaqty gcqdiatqlv nnmdidvilg
    ggrmymfpeg tpdpeypydv 241 nqtgvrkdkr nlvqewqakh qgagyvwnrt ellqaandps
    vthlmglfep admkynvqqd 301 ptkdptleem teaalqvlsr npqgfylfve ggridhghhe
    gkaymaltdt vmfdnaiaka 361 neltseldtl ilatadhshv fsfggytlrg tsifglapsk
    asdnksytsi lygngpgyvl 421 ggglrpdvnd sisedpsyrq qaavplsses hggedvavfa
    rgpqahlvhg vqeetfvahv 481 mafagcvepy tdcnlappag ttdaahpieg rsvvpallpl
    ragtlllet atap
```

In various embodiments, the AP-based agent of the invention is efficiently expressed and secreted from a host cell. In an embodiment, the AP-based agent of the invention is efficiently transcribed in the host cell. In another embodiment, the AP-based agent exhibits enhanced RNA stability and/or transport in the host cell. In another embodiment, the AP-based agent is efficiently translated in the host cell. In a further embodiment, the AP-based agent is efficiently folded and/or transits efficiently through the ER, pre-golgi, and golgi. In another embodiment, the AP-based agent exhibits enhanced protein stability.

In various embodiments, the AP-based agent of the invention is GPI anchored to the cell membrane of a host cell. In other embodiments, the AP-based agent is secreted from the host cell. In such embodiments, the AP-based agent may include a protease cleavage site just upstream from the GPI anchor site. Illustrative protease cleavage sites are described previously. In an embodiment, the protease cleavage site is a furin cleavage site. In another embodiment, the AP-based agent may include a cleavage site recognized by a digestive enzyme in the GI tract just upstream from the GPI anchor site. In these embodiments, the AP-based agent is anchored in the ER and released in the late golgi and secreted.

In various embodiments, the AP-based agents are efficiently expressed in a host cell. In an embodiment, the Kozak sequence of the DNA construct encoding the AP-based agent is optimized. The Kozak sequence is the nucleotide sequence flanking the ATG start codon that instructs the ribosome to start translation. There is flexibility in the design of a Kozak sequence, but one canonical sequence is GCCGCCACCATGG (SEQ ID NO: 38). The purine in the −3 position and the G in the +4 position are the most important bases for translation initiation. For hIAP, bIAP II, and bIAP IV, the second amino acid, that is, the one after the initiator methionine, is glutamine. Codons for glutamine all have a C in the first position. Thus, their Kozak sequences all have an ATGC (SEQ ID NO: 39) sequence. Accordingly, in various embodiments, the ATGC (SEQ ID NO: 39) sequence is changed to ATGG (SEQ ID NO: 40). This can be achieved by changing the second amino acid to a glycine, alanine, valine, aspartate, or glutamic acid, all of whose codons have a G in the first position. These amino acids may be compatible with signal peptide function. In alternative embodiments, the entire signal peptide is substituted for peptide having a canonical Kozak sequence and is derived from a highly expressed protein such as an immunoglobulin.

In various embodiments, the signal peptide of the AP-based agent may be deleted and/or substituted. For example, the signal peptide may be deleted, mutated, and/or substituted (e.g., with another signal peptide) to ensure protein expression.

In some embodiments, The DNA construct encoding the AP-based agent of the invention comprises untranslated DNA sequences. Such sequences include an intron, which may be heterologous to the IAP protein or native to the IAP protein including the native first and/or second intron and/or a native 3' UTR. Without wishing to be bound by theory, it is believed that include of these sequences enhance protein expression by stabilizing the mRNA. Accordingly, in various embodiments, the DNA construct encoding the AP-based agent of the invention comprises the 5'UTR and/or the 3'UTR.

Provided below are illustrative IAP DNA sequences with a first intron and a 3'UTR:

```
hIAP with native first intron (shown as bolded and underlined)
                                                    SEQ ID NO: 12
ATGCAGGGGCCCTGGGTGCTGCTGCTGCTGGGCCTGAGGCTACAGCTCTCCCTGGGCG

TCATCCCAGGTAATGAGGCTCCCCAAGCTGTTCCACACACAGGGCACCCCCTCAGCCA

GGCTGACCTGATCTCTACTCTCCCCCTGGCCAGCTGAGGAGGAGAACCCGGCCTTCTGG

AACCGCCAGGCAGCTGAGGCCCTGGATGCTGCCAAGAAGCTGCAGCCCATCCAGAAGGT

CGCCAAGAACCTCATCCTCTTCCTGGGCGATGGGTTGGGGGTGCCCACGGTGACAGCCA

CCAGGATCCTAAAGGGGCAGAAGAATGGCAAACTGGGGCCTGAGACGCCCCTGGCCAT

GGACCGCTTCCCATACCTGGCTCTGTCCAAGACATACAATGTGGACAGACAGGTGCCAG

ACAGCGCAGCCACAGCCACGGCCTACCTGTGCGGGGTCAAGGCCAACTTCCAGACCATC

GGCTTGAGTGCAGCCGCCCGCTTTAACCAGTGCAACACGACACGCGGCAATGAGGTCAT

CTCCGTGATGAACCGGGCCAAGCAAGCAGGAAAGTCAGTAGGAGTGGTGACCACCACAC

GGGTGCAGCACGCCTCGCCAGCCGGCACCTACGCACACACAGTGAACCGCAACTGGTA

CTCAGATGCTGACATGCCTGCCTCAGCCCGCCAGGAGGGGTGCCAGGACATCGCCACTC

AGCTCATCTCCAACATGGACATTGACGTGATCCTTGGCGGAGGCCGCAAGTACATGTTTC

CCATGGGGACCCCAGACCCTGAGTACCCAGCTGATGCCAGCCAGAATGGAATCAGGCTG

GACGGGAAGAACCTGGTGCAGGAATGGCTGGCAAAGCACCAGGGTGCCTGGTATGTGT

GGAACCGCACTGAGCTCATGCAGGCGTCCCTGGACCAGTCTGTGACCCATCTCATGGGC

CTCTTTGAGCCCGGAGACACGAAATATGAGATCCACCGAGACCCCACACTGGACCCCTC

CCTGATGGAGATGACAGAGGCTGCCCTGCGCCTGCTGAGCAGGAACCCCCGCGGCTTCT

ACCTCTTTGTGGAGGGCGGCCGCATCGACCATGGTCATCATGAGGGTGTGGCTTACCAG

GCACTCACTGAGGCGGTCATGTTCGACGACGCCATTGAGAGGGCGGGCCAGCTCACCA

GCGAGGAGGACACGCTGACCCTCGTCACCGCTGACCACTCCCATGTCTTCTCCTTTGGT

GGCTACACCTTGCGAGGGAGCTCCATCTTCGGGTTGGCCCCCAGCAAGGCTCAGGACAG

CAAAGCCTACACGTCCATCCTGTACGGCAATGGCCCGGGCTACGTGTTCAACTCAGGCG

TGCGACCAGACGTGAATGAGAGCGAGAGCGGGAGCCCCGATTACCAGCAGCAGGCGGC

GGTGCCCCTGTCGTCCGAGACCCACGGAGGCGAAGACGTGGCGGTGTTTGCGCGCGGC
```

```
CCGCAGGCGCACCTGGTGCATGGTGTGCAGGAGCAGAGCTTCGTAGCGCATGTCATGG

CCTTCGCTGCCTGTCTGGAGCCCTACACGGCCTGCGACCTGGCGCCTCCCGCCTGCACC

ACCGACGCCGCGCACCCAGTTGCCGCGTCGCTGCCACTGCTGGCCGGGACCCTGCTGC

TGCTGGGGCGTCCGCTGCTCCCTGA
``` hIAP with native 3' UTR (shown as bolded and underlined)
SEQ ID NO: 13
```
ATGCAGGGGCCCTGGGTGCTGCTGCTGCTGGGCCTGAGGCTACAGCTCTCCCTGGGCG

TCATCCCAGCTGAGGAGGAGAACCCGGCCTTCTGGAACCGCCAGGCAGCTGAGGCCCT

GGATGCTGCCAAGAAGCTGCAGCCCATCCAGAAGGTCGCCAAGAACCTCATCCTCTTCCT

GGGCGATGGGTTGGGGGTGCCCACGGTGACAGCCACCAGGATCCTAAAGGGGCAGAAG

AATGGCAAACTGGGGCCTGAGACGCCCCTGGCCATGGACCGCTTCCCATACCTGGCTCT

GTCCAAGACATACAATGTGGACAGACAGGTGCCAGACAGCGCAGCCACAGCCACGGCCT

ACCTGTGCGGGGTCAAGGCCAACTTCCAGACCATCGGCTTGAGTGCAGCCGCCCGCTTT

AACCAGTGCAACACGACACGCGGCAATGAGGTCATCTCCGTGATGAACCGGGCCAAGCA

AGCAGGAAAGTCAGTAGGAGTGGTGACCACCACACGGGTGCAGCACGCCTCGCCAGCC

GGCACCTACGCACACAGTGAACCGCAACTGGTACTCAGATGCTGACATGCCTGCCTC

AGCCCGCCAGGAGGGGTGCCAGGACATCGCCACTCAGCTCATCTCCAACATGGACATTG

ACGTGATCCTTGGCGGAGGCCGCAAGTACATGTTTCCCATGGGGACCCCAGACCCTGAG

TACCCAGCTGATGCCAGCCAGAATGGAATCAGGCTGGACGGGAAGAACCTGGTGCAGGA

ATGGCTGGCAAAGCACCAGGGTGCCTGGTATGTGTGGAACCGCACTGAGCTCATGCAGG

CGTCCCTGGACCAGTCTGTGACCCATCTCATGGGCCTCTTTGAGCCCGGAGACACGAAA

TATGAGATCCACCGAGACCCCACACTGGACCCCTCCCTGATGGAGATGACAGAGGCTGC

CCTGCGCCTGCTGAGCAGGAACCCCCGCGGCTTCTACCTCTTTGTGGAGGGCGGCCGC

ATCGACCATGGTCATCATGAGGGTGTGGCTTACCAGGCACTCACTGAGGCGGTCATGTTC

GACGACGCCATTGAGAGGGCGGGCCAGCTCACCAGCGAGGAGGACACGCTGACCCTCG

TCACCGCTGACCACTCCCATGTCTTCTCCTTTGGTGGCTACACCTTGCGAGGGAGCTCCA

TCTTCGGGTTGGCCCCCAGCAAGGCTCAGGACAGCAAAGCCTACACGTCCATCCTGTAC

GGCAATGGCCCGGGCTACGTGTTCAACTCAGGCGTGCGACCAGACGTGAATGAGAGCGA

GAGCGGGAGCCCCGATTACCAGCAGCAGGCGGCGGTGCCCCTGTCGTCCGAGACCCAC

GGAGGCGAAGACGTGGCGGTGTTTGCGCGCGGCCCGCAGGCGCACCTGGTGCATGGTG

TGCAGGAGCAGAGCTTCGTAGCGCATGTCATGGCCTTCGCTGCCTGTCTGGAGCCCTAC

ACGGCCTGCGACCTGGCGCCTCCCGCCTGCACCACCGACGCCGCGCACCCAGTTGCCG

CGTCGCTGCCACTGCTGGCCGGGACCCTGCTGCTGCTGGGGGCGTCCGCTGCTCCCTG

ATTTACTAAAACCTTGAAATAAAATTGTAAAACATCAGTTTGAAGGCCTGACTCTCAGGG

TAGTTCTTTTTAATTCTGGGTTTT
``` blAP IV with the first intron from blAP I (shown as bolded and underlined)
SEQ ID NO: 14
```
ATGCAGTGGGCCTGTGTGCTGCTGCTGCTGGGCCTGTGGCTACAGCTCTCCCTCACCTT

CATCCCAG**GTAATCAGGCGGCTCCCAGCAGCCCCTACTCACAGGGGCGGCTCTAGGCT

GACCTGACCAACACTCTCCCCTTGGGCAG**CTGAGGAGGAAGACCCCGCCTTCTGGAACC

GCCAGGCAGCCCAGGCCCTTGATGTAGCCAAGAAGTTGCAGCCGATCCAGACAGCTGCC

AAGAATGTCATCCTCTTCTTGGGGGATGGGATGGGGGTGCCTACGGTGACAGCCACTCG
```

-continued

```
GATCCTAAAGGGGCAGATGAATGGTAAGCTGGGACCTGAGACACCCCTGGCCATGGACC

AGTTCCCATACGTGGCTCTGTCCAAGACATACAACGTGGACAGACAGGTGCCAGACAGC

GCAGGCACTGCCACTGCCTACCTGTGTGGGGTCAAGGGCAACTACAAAACCATTGGTGT

AAGTGCAGCCGCCCGCTACAACCAGTGCAACACAACAAGTGGCAATGAGGTCACGTCTG

TGATGAACCGGGCCAAGAAAGCAGGAAAGTCAGTGGGAGTGGTGACCACCTCCAGGGTG

CAGCATGCCTCCCCAGCCGGTGCTTATGCACACACGGTGAACCGAAACTGGTACTCAGA

TGCCGACCTGCCTGCCGATGCACAGACGTATGGCTGCCAGGACATCGCCACACAACTGG

TCAACAACATGGATATTGACGTGATCCTGGGTGGAGGCCGAATGTACATGTTTCCTGAGG

GGACCCCGGATCCTGAATACCCATACGATGTCAATCAGACTGGAGTCCGGAAGGACAAG

CGGAATCTGGTGCAGGAGTGGCAGGCCAAGCACCAGGGAGCCCAGTATGTGTGGAACC

GCACGGAGCTCCTTCAGGCAGCCAATGACCCCAGTGTAACACACCTCATGGGCCTCTTT

GAGCCGGCAGACATGAAGTATAATGTTCAGCAAGACCCCACCAAGGACCCGACCCTGGA

GGAGATGACGGAGGCGGCCCTGCAAGTGCTGAGCAGGAACCCCCAGGGCTTCTACCTC

TTCGTGGAGGGAGGCCGCATTGACCACGGTCACCATGAAGGCAAAGCTTATATGGCACT

GACTGATACAGTCATGTTTGACAATGCCATCGCCAAGGCTAACGAGCTCACTAGCGAACT

GGACACGCTGATCCTTGCCACTGCAGACCACTCCCATGTCTTCTCTTTTGGTGGCTACAC

ACTGCGTGGGACCTCCATTTTCGGTCTGGCCCCCAGCAAGGCCTCAGACAACAAGTCCT

ACACCTCCATCCTCTATGGCAATGCCCTGGCTACGTGCTTGGTGGGGCTTAAGGCCC

GATGTTAATGACAGCATAAGCGAGGACCCCTCGTACCGGCAGCAGGCGGCCGTGCCCCT

GTCTAGTGAGTCCCACGGGGGCGAGGACGTGGCGGTGTTCGCGCGAGGCCCGCAGGC

GCACCTGGTGCACGGCGTGCAGGAGGAGACCTTCGTGGCGCACGTCATGGCCTTTGCG

GGCTGCGTGGAGCCCTACACCGACTGCAATCTGCCGGCCCCCTCTGGCCTCTCCGACGC

CGCGCACCTGGCGGCCAGCCCGCCTTCGCTGGCGCTGCTGGCCGGGGCGATGCTGCTG

CTGCTGGCGCCTGCCTTGTACTGA
``` blAP IV with the 3' UTR from blAP I (shown as bolded and underlined)
SEQ ID NO: 15

```
ATGCAGTGGGCCTGTGTGCTGCTGCTGCTGGGCCTGTGGCTACAGCTCTCCCTCACCTT

CATCCCAGCTGAGGAGGAAGACCCCGCCTTCTGGAACCGCCAGGCAGCCCAGGCCCTT

GATGTAGCCAAGAAGTTGCAGCCGATCCAGACAGCTGCCAAGAATGTCATCCTCTTCTTG

GGGGATGGGATGGGGGTGCCTACGGTGACAGCCACTCGGATCCTAAAGGGGCAGATGA

ATGGTAAGCTGGGACCTGAGACACCCCTGGCCATGGACCAGTTCCCATACGTGGCTCTG

TCCAAGACATACAACGTGGACAGACAGGTGCCAGACAGCGCAGGCACTGCCACTGCCTA

CCTGTGTGGGGTCAAGGGCAACTACAAAACCATTGGTGTAAGTGCAGCCGCCCGCTACA

ACCAGTGCAACACAACAAGTGGCAATGAGGTCACGTCTGTGATGAACCGGGCCAAGAAA

GCAGGAAAGTCAGTGGGAGTGGTGACCACCTCCAGGGTGCAGCATGCCTCCCCAGCCG

GTGCTTATGCACACACGGTGAACCGAAACTGGTACTCAGATGCCGACCTGCCTGCCGAT

GCACAGACGTATGGCTGCCAGGACATCGCCACACAACTGGTCAACAACATGGATATTGAC

GTGATCCTGGGTGGAGGCCGAATGTACATGTTTCCTGAGGGGACCCCGGATCCTGAATA

CCCATACGATGTCAATCAGACTGGAGTCCGGAAGGACAAGCGGAATCTGGTGCAGGAGT

GGCAGGCCAAGCACCAGGGAGCCCAGTATGTGTGGAACCGCACGGAGCTCCTTCAGGC

AGCCAATGACCCCAGTGTAACACACCTCATGGGCCTCTTTGAGCCGGCAGACATGAAGTA
```

-continued

```
TAATGTTCAGCAAGACCCCACCAAGGACCCGACCCTGGAGGAGATGACGGAGGCGGCC

CTGCAAGTGCTGAGCAGGAACCCCCAGGGCTTCTACCTCTTCGTGGAGGGAGGCCGCAT

TGACCACGGTCACCATGAAGGCAAAGCTTATATGGCACTGACTGATACAGTCATGTTTGA

CAATGCCATCGCCAAGGCTAACGAGCTCACTAGCGAACTGGACACGCTGATCCTTGCCA

CTGCAGACCACTCCCATGTCTTCTCTTTTGGTGGCTACACACTGCGTGGGACCTCCATTTT

CGGTCTGGCCCCCAGCAAGGCCTCAGACAACAAGTCCTACACCTCCATCCTCTATGGCAA

TGGCCCTGGCTACGTGCTTGGTGGGGGCTTAAGGCCCGATGTTAATGACAGCATAAGCG

AGGACCCCTCGTACCGGCAGCAGGCGGCCGTGCCCCTGTCTAGTGAGTCCCACGGGGG

CGAGGACGTGGCGGTGTTCGCGCGAGGCCCGCAGGCGCACCTGGTGCACGGCGTGCA

GGAGGAGACCTTCGTGGCGCACGTCATGGCCTTTGCGGGCTGCGTGGAGCCCTACACC

GACTGCAATCTGCCGGCCCCCTCTGGCCTCTCCGACGCCGCGCACCTGGCGGCCAGCC

CGCCTTCGCTGGCGCTGCTGGCCGGGGCGATGCTGCTGCTGCTGGCGCCTGCCTTGTA

CTGAGGGGACCCGGGGGTGGGGACACAGGCCCCGCCTCCTGGGAGGCAGGAAGC

AGCTCTCAAATAAACTGTTCTAAGTATGATACAGGAGTGATACATGTGTGAAGAGAAGC

CCTTAGGTGGGGGCACAGAGTGTCTGGGTGAGGGGGGTCAGGGTCACATCAGGAGGT

TAGGGAGGGGTTGATGAAGGGCTGACGTTGAGCAAACACCAAAGGCAACTCAGAAGG

ACAGTGGTGCAGGACTGGGTGTGGTCAGCAGGGGGACTGGTTGGGGGATCC
```

In various embodiments, the present invention contemplates the use of bacterial alkaline phosphatases. In some embodiments, the AP-based agent of the invention is derived from *Bacillus subtilis*. *Bacillus subtilis* is a Gram-positive bacterium found in soil and the gastrointestinal tract of humans. *Bacillus subtilis* secretes high levels of proteins into the environment and in the human GI tract that are properly folded. Without wishing to be bound by theory, it is believed that *Bacillus subtilis* secreted proteins in the GI tract may be resistant to degradation by common gastrointestinal proteases. *Bacillus subtilis* expresses at high levels an alkaline phosphatase multigene family. Among those isozymes, alkaline phosphatase IV is responsible for the majority of total alkaline phosphatase expression and activity in *B. subtilis*. In some embodiments, the AP-based agent of the invention is derived from *Bacillus licheniformis*. In some embodiments, the AP-based agent of the invention is derived from *Escherichia coli*.

Accordingly, in an illustrative embodiment, the AP-based agent of the invention is derived from alkaline phosphatase IV of *Bacillus subtilis*. In an embodiment, the bacterial alkaline phosphatase may have the following nucleotide and amino acid sequences:

*Bacillus subtilis* JH642 alkaline phosphatase IV,
mature protein nucleotide sequence -
SEQ ID NO: 16

```
AAAAAACAAGACAAAGCTGAGATCAGAAATGTCATTGTGATGATAGGCGA

CGGCATGGGGACGCCTTACATAAGAGCCTACCGTTCCATGAAAAATAACG

GTGACACACCGAATAACCCGAAGTTAACAGAATTTGACCGGAACCTGACA

GGCATGATGATGACGCATCCGGATGACCCTGACTATAATATTACAGATTC

AGCAGCAGCCGGAACAGCATTAGCGACAGGCGTTAAGACATATAACAATG

CAATTGGCGTCGATAAAAACGGAAAAAAAGTGAAATCTGTACTTGAAGAG
```

-continued

```
GCCAAACAGCAAGGCAAGTCAACAGGGCTTGTCGCCACGTCTGAAATTAA

CCACGCCACTCCAGCCGCATATGGCGCCCACAATGAATCACGGAAAAACA

TGGACCAAATCGCCAACAGCTATATGGATGACAAGATAAAAGGCAAACAT

AAAATAGACGTGCTGCTCGGCGGCGGAAAATCTTATTTTAACCGCAAGAA

CAGAAACTTGACAAAGGAATTCAAACAAGCCGGCTACAGCTATGTGACAA

CTAAACAAGCATTGAAAAAAATAAAGATCAGCAGGTGCTCGGGCTTTTC

GCAGATGGAGGGCTTGCTAAAGCGCTCGACCGTGACAGTAAAACACCGTC

TCTCAAAGACATGACGGTTTCAGCAATTGATCGCCTGAACCAAAATAAAA

AAGGATTTTTCTTGATGGTCGAAGGGAGCCAGATTGACTGGGCGGCCCAT

GACAATGATACAGTAGGAGCCATGAGCGAGGTTAAAGATTTTGAACAGGC

CTATAAAGCCGCGATTGAATTTGCGAAAAAAGACAAACATACACTTGTGA

TTGCAACTGCTGACCATACAACCGGCGGCTTTACCATTGGCGCAAACGGG

GAAAAGAATTGGCACGCAGAACCGATTCTCTCCGCTAAGAAAACACCTGA

ATTCATGGCCAAAAAAATCAGTGAAGGCAAGCCGGTTAAAGATGTGCTCG

CCCGCTATGCCAATCTGAAAGTCACATCTGAAGAAATCAAAAGCGTTGAA

GCAGCTGCACAGGCTGACAAAAGCAAAGGGGCCTCCAAAGCCATCATCAA

GATTTTTAATACCCGCTCCAACAGCGGATGGACGAGTACCGATCATACCG

GCGAAGAAGTACCGGTATACGCGTACGGCCCCGGAAAAGAAAAATTCCGC

GGATTGATTAACAATACGGACCAGGCAAACATCATATTTAAGATTTTAAA

AACTGGAAAA
```

-continued

Bacillus subtilis JH642 alkaline phosphatase IV,
mature protein amino acid sequence -
SEQ ID NO: 17
KKQDKAEIRNVIVMIGDGMGTPYIRAYRSMKNNGDTPNNPKLTEFDRNLT

GMMMTHPDDPDYNITDSAAAGTALATGVKTYNNAIGVDKNGKKVKSVLEE

AKQQGKSTGLVATSEINHATPAAYGAHNESRKNMDQIANSYMDDKIKGKH

KIDVLLGGGKSYFNRKNRNLTKEFKQAGYSYVTTKQALKKNKDQQVLGLF

ADGGLAKALDRDSKTPSLKDMTVSAIDRLNQNKKGFFLMVEGSQIDWAAH

DNDTVGAMSEVKDFEQAYKAAIEFAKKDKHTLVIATADHTTGGFTIGANG

EKNWHAEPILSAKKTPEFMAKKISEGKPVKDVLARYANLKVTSEEIKSVE

AAAQADKSKGASKAIIKIFNTRSNSGWTSTDHTGEEVPVYAYGPGKEKFR

GLINNTDQANIIFKILKTGK

In some embodiments, the AP-based agent includes bacterial alkaline phosphatases that has one or more mutations that alter catalytic activity. In some embodiments, the bacterial alkaline phosphatases include one or more mutations such that their catalytic activity is similar or higher than mammalian alkaline phosphatases. In some embodiments, the bacterial alkaline phosphatases include one or more mutations that alter their de-phosphorylation profile. In an embodiment, the bacterial alkaline phosphatases of the invention exhibits similar de-phosphorylation profile as mammalian alkaline phosphatases. In some embodiments, the bacterial alkaline phosphatases include one or more mutations that alter their activity at higher pH. In an embodiment, the bacterial alkaline phosphatases of the invention exhibits similar activity at higher pH as mammalian alkaline phosphatases. In some embodiments, the bacterial alkaline phosphatases include one or more mutations that alter their metal requirements. In an embodiment, the bacterial alkaline phosphatases of the invention exhibits metal requirements (e.g., Mg) as mammalian alkaline phosphatases.

For example, in certain embodiments, the AP-based agent of the invention is derived from Bacillus subtilis JH642 alkaline phosphatase IV, and has one or more mutations at positions 101, 328, A330, and 374. For example, the AP-based agent may include one or more of the following mutations: D101A, W328H, A330N and G374C.

In various embodiments, the AP-based agent of the invention comprises a nucleotide sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein.

In some embodiments, the AP-based agent of the invention comprises an amino sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein.

In various embodiments, the AP-based agent of the invention may comprise an amino acid sequence having one or more amino acid mutations relative any of the protein sequences described herein. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, 3-alanine, fluoro-amino acids, designer amino acids such as β methyl amino acids, C α-methyl amino acids, N α-methyl amino acids, and amino acid analogs in general).

Mutations may also be made to the nucleotide sequences of the alkaline phosphatases by reference to the genetic code, including taking into account codon degeneracy. In various embodiments, the DNA construct encoding the AP-based agent is codon optimized for protein expression in the host cell.

Mutations may be made to the AP-based agent of the invention to select for agents with desired characteristics. For examples, mutations may be made to generate AP-based agents with enhanced catalytic activity or protein stability. In various embodiments, directed evolution may be utilized to generate AP-based agents of the invention. For example, error-prone PCR and DNA shuffling may be used to identify mutations in the bacterial alkaline phosphatases that confer enhanced activity.

In various embodiments, the AP-based agent of the invention possesses desirable characteristics, including, for example, high specific activity. In various embodiments, the alkaline phosphatase of the invention possesses a specific activity of at least about 100 U/mg to about 20,000 U/mg. In various embodiments, the alkaline phosphatase of the invention possesses a specific activity of at least about 100 U/mg, about 200 U/mg, about 300 U/mg, about 400 U/mg, about 500 U/mg, about 600 U/mg, about 700 U/mg, about 800 U/mg, about 900 U/mg, about 1,000 U/mg, about 2,000 U/mg, about 3,000 U/mg, about 4,000 U/mg, about 5,000 U/mg, about 6,000 U/mg, about 7,000 U/mg, about 8,000 U/mg, about 9,000 U/mg, about 10,000 U/mg, about 11,000 U/mg, about 12,000 U/mg, about 13,000 U/mg, about 14,000 U/mg, about 15,000 U/mg, about 16,000 U/mg, about 17,000 U/mg, about 18,000 U/mg, about 19,000 U/mg, or about 20,000 U/mg.

In various embodiments, the AP-based agent of the invention is stable and/or active in the GI tract, e.g. in one or more of the mouth, esophagus, stomach, duodenum, small intestine, duodenum, jejunum, ileum, large intestine, colon transversum, colon descendens, colon ascendens, colon sigmoidenum, cecum, and rectum. In a specific embodiment, the alkaline phosphatase is stable in the large intestine, optionally selected from one or more of colon transversum, colon descendens, colon ascendens, colon sigmoidenum and cecum. In a specific embodiment, the alkaline phosphatase is stable in the small intestine, optionally selected from one or more of duodenum, jejunum, and ileum. In some embodiments, the alkaline phosphatase is resistant to proteases in the GI tract, including for example, the small intestine. In some embodiments, the alkaline phosphatase is substantially active at a pH of about 5.0 or above. For example, the alkaline phosphatase may be substantially active at a pH about 6.0 to about 12, e.g. about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5, or about 8.0, or about 8.5, or about 9.0, or about 9.5, or about 10.0, or about 10.5, or about 11.0, or about 11.5, or about 12.0 (including, for example, via formulation, as described herein). In some embodiments, stable refers to an enzyme that has a long enough half-life and maintains sufficient activity for therapeutic effectiveness.

In various embodiments, the AP-based agent of the invention is stable in chyme.

In some embodiments, the AP-based agent described herein, include derivatives that are modified, i.e., by the covalent attachment of any type of molecule to the alkaline phosphatase such that covalent attachment does not prevent the activity of the enzyme. For example, but not by way of limitation, derivatives include alkaline phosphatases that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out, including, but not limited to specific chemical cleavage, acetylation, formylation, metabolic synthesis of tunicamycin, etc. Additionally, the derivative can contain one or more non-classical amino acids. In various embodiments, the AP-based agent is glycosylated to ensure proper protein folding.

In still other embodiments, the AP-based agents of the invention may be modified to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

The AP-based agent described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the alkaline phosphatases having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Further, any AP-based agent described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, cellulose, hypromellose, lactose, sucrose, malt, rice, flour, chalk, silica gel, sodium stearate, glycerol monostearate, talc, sodium chloride, dried skim milk, glycerol, propylene, glycol, povidone, crosspovidone, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the AP-based agent and/or pharmaceutical compositions (and/or additional therapeutic agents) can include a solubilizing agent. Also, the agents can be delivered with a suitable vehicle or delivery device. Compositions for administration can optionally include a local anesthetic such as, for example, lignocaine to lessen pain at the site of the injection. Combination therapies outlined herein can be co-delivered in a single delivery vehicle or delivery device.

Methods of Making IAP

The IAPs of the invention are made using standard molecular biology techniques. For example, nucleic acid compositions encoding the IAPs of the invention are also provided, as well as expression vectors containing the nucleic acids and host cells transformed with the nucleic acid and/or expression vector compositions. As will be appreciated by those in the art, the protein sequences depicted herein can be encoded by any number of possible nucleic acid sequences, due to the degeneracy of the genetic code.

As is known in the art, the nucleic acids encoding the components of the invention can be incorporated into expression vectors as is known in the art, and depending on the host cells, used to produce the IAP compositions of the invention. Generally, the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with mammalian cells (e.g. CHO cells), finding use in many embodiments.

The IAPs of the invention are made by culturing host cells comprising the expression vector(s) as is well known in the art. Once produced, traditional purification steps are done.

Formulations Comprising AP-Based Agents

The present invention provides the described AP-based agent and/or pharmaceutical compositions (and/or additional therapeutic agents) in various formulations. Any AP-based agent and/or pharmaceutical composition (and/or additional therapeutic agents) described herein can take the form of tablets, pills, pellets, capsules, capsules containing liquids, capsules containing multiparticulates, powders, solutions, emulsion, drops, suppositories, emulsions, aerosols, sprays, suspensions, delayed-release formulations, sustained-release formulations, controlled-release formulations, or any other form suitable for use.

The formulations comprising the AP-based agent and/or pharmaceutical compositions (and/or additional therapeutic agents) may conveniently be presented in unit dosage forms. For example, the dosage forms may be prepared by methods which include the step of bringing the therapeutic agents into association with a carrier, which constitutes one or more accessory ingredients. For example, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by press tableting)

In one embodiment, an IAP (and/or additional therapeutic agents) described herein is formulated as a composition adapted for a mode of administration described herein.

In some embodiments, the administration an IAP and/or pharmaceutical compositions (and/or additional therapeutic agents) is any one of oral, intravenous, and parenteral. For example, routes of administration include, but are not limited to, oral, intradermal, intramuscular, intraperitoneal, intravenous, subcutaneous, intranasal, epidural, sublingual, intranasal, intracerebral, intravaginal, transdermal, rectally, by inhalation, or topically (e.g., to the ears, nose, eyes, or skin).

In some embodiments, an IAP and/or pharmaceutical compositions (and/or additional therapeutic agents) described herein is formulated as a composition adapted for oral administration. Compositions for oral delivery can be in the form of tablets, lozenges, aqueous or oily suspensions, granules, powders, sprinkles, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration to provide a sustained action over an extended period of time. Selectively permeable membranes surrounding an osmotically active agent driving any alkaline phosphatase (and/or additional therapeutic agents) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, ethacrylic acid and derivative polymers thereof, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

In various embodiments, the AP-based agent and/or pharmaceutical compositions (and/or additional therapeutic agent) are formulated as solid dosage forms such as tablets, dispersible powders, granules, and capsules. In one embodiment, the AP-based agent and/or pharmaceutical compositions (and/or additional therapeutic agent) are formulated as a capsule. In another embodiment, the AP-based agent and/or pharmaceutical compositions (and/or additional therapeutic agent) are formulated as a tablet. In yet another embodiment, the AP-based agent and/or pharmaceutical compositions (and/or additional therapeutic agent) are formulated as a soft-gel capsule. In a further embodiment, the AP-based agent and/or pharmaceutical compositions (and/or additional therapeutic agent) are formulated as a gelatin capsule.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g., lyophilized composition), which can be dissolved or suspended in sterile injectable medium immediately before use. They may contain, for example, suspending or dispersing agents.

In various embodiments, the formulations of the AP-based agents, such as an IAP, may additionally comprise a pharmaceutically acceptable carrier or excipient. As one skilled in the art will recognize, the formulations can be in any suitable form appropriate for the desired use and route of administration.

In some dosage forms, the agents described herein are mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

The formulation can additionally include a surface active agent. Surface active agents suitable for use in the present invention include, but are not limited to, any pharmaceutically acceptable, non-toxic surfactant. Classes of surfactants suitable for use in the compositions of the invention include, but are not limited to polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof. In some embodiments, compositions of the invention may comprise one or more surfactants including, but not limited to, sodium lauryl sulfate, polysorbate 20, polysorbate 40, polysorbate 60, polysorbate 80, and triethyl citrate.

The formulation can also contain pharmaceutically acceptable plasticizers to obtain the desired mechanical properties such as flexibility and hardness. Such plasticizers include, but are not limited to, triacetin, citric acid esters, triethyl citrate, phthalic acid esters, dibutyl sebacate, cetyl alcohol, polyethylene glycols, polysorbates or other plasticizers.

The formulation can also include one or more application solvents. Some of the more common solvents that can be used to apply, for example, a delayed-release coating composition include isopropyl alcohol, acetone, methylene chloride and the like.

The formulation can also include one or more alkaline materials. Alkaline material suitable for use in compositions of the invention include, but are not limited to, sodium, potassium, calcium, magnesium and aluminum salts of acids such as phosphoric acid, carbonic acid, citric acid and other aluminum/magnesium compounds. In addition, the alkaline material may be selected from antacid materials such as aluminum hydroxides, calcium hydroxides, magnesium hydroxides and magnesium oxide.

In various embodiments, the formulation can additionally include magnesium and/or zinc. The inclusion of magnesium and/or zinc in the formulation may promote protein folding (e.g., dimer formation) and bioactivity of the AP-based agent. In some embodiments, the formulation can include magnesium at a concentration of from about 1 μM to greater than 500 mM (e.g., from about 1 μM to more than 5 mM), inclusive of all ranges and values therebetween. In some embodiments, the formulation can include zinc at a concentration of about 1 μM to greater than 100 mM (e.g., from about 1 μM to more than 1 mM), inclusive of all ranges and values therebetween. In various embodiments, the formulation of the present invention is substantially free of metal chelators.

In various embodiments, the pH of the formulation ensures that the AP-based agent is properly folded (e.g., dimer formation) and is bioactive. In some embodiments, the formulation is maintained at a pH such that the amino acids which coordinate the binding of magnesium and/or zinc within the AP-based agent are not protonated. Protonation of such coordinating amino acids may lead to loss of metal ions and bioactivity and dimer disassociation. In various embodiments, the pH of the formulation is greater than about 6, about 6.5, about 7, about 7.5, about 8, about 8.5, about 9, about 9.5, about 10, about 10.5, about 11, about 11.5, or about 12.

Besides inert diluents, the oral compositions can also include adjuvants such as sweetening, flavoring, and perfuming agents.

In various embodiments, the AP-based agent and/or pharmaceutical compositions (and/or additional therapeutic agents) are formulated for systemic or local delivery. In an embodiment, administration is systemic. In another embodiment, it may be desirable to administer locally to the area in need of treatment.

Various methods may be used to formulate and/or deliver the agents described herein to a location of interest. For example, the intestinal alkaline phosphatase and/or pharmaceutical compositions (and/or additional therapeutic agents) described herein may be formulated for delivery to the gastrointestinal tract. The gastrointestinal tract includes organs of the digestive system such as mouth, esophagus, stomach, duodenum, small intestine, large intestine and rectum and includes all subsections thereof (e.g., the small intestine may include the duodenum, jejunum and ileum; the large intestine may include the colon transversum, colon descendens, colon ascendens, colon sigmoidenum and cecum). For example, the alkaline phosphatases and/or pharmaceutical compositions (and/or additional therapeutic agents) described herein may be formulated for delivery to one or more of the stomach, small intestine, large intestine and rectum and includes all subsections thereof (e.g., duodenum, jejunum and ileum, colon transversum, colon descendens, colon ascendens, colon sigmoidenum and cecum). In some embodiments, the compositions described herein may be formulated to deliver to the upper or lower GI tract. In an embodiment, the alkaline phosphatases and/or pharmaceutical compositions (and/or additional therapeutic agents) may be administered to a subject, by, for example, directly or indirectly contacting the mucosal tissues of the gastrointestinal tract.

In various embodiments, the administration the AP-based agent and/or pharmaceutical compositions (and/or additional therapeutic agents) is into the GI tract via, for example, oral delivery, nasogastral tube, intestinal intubation (e.g., an enteral tube or feeding tube such as, for example, a jejunal tube or gastro-jejunal tube, etc.), direct infusion (e.g., duodenal infusion), endoscopy, colonoscopy, or enema.

Administration and Dosages

As a person of skill in the art will appreciate, the actual dose of an IAP to be administered according to the present invention will vary according to the particular compound, the particular dosage form, and the mode of administration. Many factors that may modify the action of the IAP (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Administration rates for a given set of conditions can be ascertained by those skilled in the art using conventional dosage administration tests.

Individual doses of the AP-based agent, such as the IAP, can be administered in unit dosage forms (e.g., tablets or capsules) containing, for example, from about 0.01 mg to about 1,000 mg, about 0.01 mg to about 900 mg, about 0.01 mg to about 800 mg, about 0.01 mg to about 700 mg, about 0.01 mg to about 600 mg, about 0.01 mg to about 500 mg, about 0.01 mg to about 400 mg, about 0.01 mg to about 300 mg, about 0.01 mg to about 200 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg, from about 0.1 mg to about 30 mg, from about 0.1 mg to about 20 mg, from about 0.1 mg to about 10 mg, from about 0.1 mg to about 5 mg, from about 0.1 mg to about 3 mg, or from about 0.1 mg to about 1 mg active ingredient per unit dosage for. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 200 mg, about 300 mg, about 400 mg, about 500 mg, about 600 mg, about 700 mg, about 800 mg, about 900 mg, or about 1,000 mg of the AP-based agent, inclusive of all values and ranges therebetween.

In one embodiment, the AP-based agent, such as the IAP, is administered at an amount of from about 0.01 mg to about 1,000 mg daily, about 0.01 mg to about 900 mg daily, about 0.01 mg to about 800 mg daily, about 0.01 mg to about 700 mg daily, about 0.01 mg to about 600 mg daily, about 0.01 mg to about 500 mg daily, about 0.01 mg to about 400 mg daily, about 0.01 mg to about 300 mg daily, about 0.01 mg to about 200 mg daily, about 0.01 mg to about 100 mg daily, an amount of from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the AP-based agent is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 200 mg, about 300 mg, about 400 mg, about 500 mg, about 600 mg, about 700 mg, about 800 mg, about 900 mg, or about 1,000 mg, inclusive of all values and ranges therebetween.

In some embodiments, a suitable dosage of the AP-based agent is in a range of about 0.01 mg/kg to about 100 mg/kg of body weight of the subject, about 0.01 mg/kg to about 90 mg/kg of body weight of the subject, about 0.01 mg/kg to about 80 mg/kg of body weight of the subject, about 0.01 mg/kg to about 70 mg/kg of body weight of the subject, about 0.01 mg/kg to about 60 mg/kg of body weight of the subject, about 0.01 mg/kg to about 50 mg/kg of body weight of the subject, about 0.01 mg/kg to about 40 mg/kg of body weight of the subject, about 0.01 mg/kg to about 30 mg/kg of body weight of the subject, about 0.01 mg/kg to about 20 mg/kg of body weight of the subject, about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 20 mg/kg body weight, about 30 mg/kg body weight, about 40 mg/kg body weight, about 50 mg/kg body weight, about 60 mg/kg body weight, about 70 mg/kg body weight, about 80 mg/kg body weight, about 90 mg/kg body weight, or about 100 mg/kg body weight, inclusive of all values and ranges therebetween. In other embodiments, a suitable dosage of the AP-based agent is in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the AP-based agent may be administered, for example, more than once daily (e.g., about two, about three, about four, about five, about six, about seven, about eight, about nine, or about ten times per day), about once per day, about every other day, about every third day, about once a week, about once every two weeks, about once every month, about once every two months, about once every three months, about once every six months, or about once every year.

Methods of Treatment, Prevention, or Reduction of Side Effects of a Chemotherapeutic Treatment In some aspects, a method of treating or preventing at least one side effect of a chemotherapeutic treatment with a nucleoside analog in a subject is provided that comprises administering to the subject an IAP, wherein the subject has undergone or is undergoing a treatment of a cancer using the chemotherapeutic treatment. The IAP is administered, simultaneously, intermittently, or in any combination thereof, with respect to the administration of the chemotherapeutic treatment with the nucleoside analog.

In various embodiments, the invention provides a method of treating, preventing, mitigating, or eliminating a side effect of a chemotherapeutic treatment in a cancer patient, comprising administering IAP to the patient. In a non-limiting example, the IAP comprises an amino acid sequence having at least about 90% sequence identity with SEQ ID NO: 41. In a further non-limiting example, the chemotherapeutic treatment comprises a nucleoside analog, optionally 5-FU. In another non-limiting example, the side effect of the chemotherapeutic treatment is diarrhea.

In various embodiments, a method of treating or preventing at least one side effect of a chemotherapeutic treatment with a nucleoside analog in a subject is provided that comprises administering to the subject an IAP, wherein the subject has undergone or is undergoing a treatment of a cancer using the chemotherapeutic treatment. In some embodiments, the effect of administering the IAP is compared to the side effect profile of a subject receiving a chemotherapeutic treatment but not receiving IAP. In a non-limiting example, the IAP comprises an amino acid sequence having at least about 90% sequence identity with SEQ ID NO: 41. In a further non-limiting example, the chemotherapeutic treatment comprises a nucleoside analog, optionally 5-FU. In another non-limiting example, the side effect of the chemotherapeutic treatment is diarrhea.

In some embodiments, the IAP is administered sequentially with the administration of the nucleoside analog, which can be prior to the administration of the nucleoside analog or after the administration of the nucleoside analog. In some cases, the administration of the IAP can at least partially overlap with the administration of the nucleoside analog. In some embodiments, the IAP is administered simultaneously with the administration of the nucleoside analog. For instance, in some embodiments, the IAP administration can begin prior to the nucleoside analog treatment (e.g., 1, 2, 3, 4, 5, 6, 7, 8, 9, 10, or more than 10 days prior to the beginning of the administration of the nucleoside analog) and can continue throughout entire nucleoside analog treatment. In some embodiments, the administration of the IAP (which can begin before or after the nucleoside analog administration begins) can continue after the completion of the administration of the nucleoside analog. For example, the administration of the IAP can continue for 1, 2, 3, 4, 5, 6, 7, 8, 9, 10, or more than 10 days after the completion of the administration of the nucleoside analog to the subject. In other embodiments, the IAP can be administered intermittently with the administration of the nucleoside analog.

In some cases, side effects, including gastrointestinal (GI) side effects of chemotherapeutic agents such as, for example, 5-FU, can be severe and life-threatening. GI side effects include, e.g., diarrhea, anorexia, nausea, emesis, stomatitis and esophagopharyngitis, and various other side effects. For example, mucositis and diarrhea are common GI side effects that are dose limiting. Various side effects associated with cancer treatments that make use of nucleoside analogs may also limit the frequency and duration of chemotherapy, thereby compromising the success of the cancer treatment.

Accordingly, the methods in accordance with some embodiments of the present disclosure can prevent, reduce, or eliminate one or more side effects associated with a chemotherapeutic treatment, including GI side effects. Non-limiting examples of side effects of the chemotherapeutic treatment comprise diarrhea, colitis, mucositis, weight loss, pain, nausea, vomiting, constipation, anemia, malnutrition, alopecia, myelosuppression, renal toxicity, hair loss, numbness, changes in tastes, loss of appetite, thinned or brittle hair, mouth sores, memory loss, hemorrhage, cardiotoxicity, hepatotoxicity, ototoxicity, and post-chemotherapy cognitive impairment.

The method in accordance with embodiments of the present disclosure, which include administration of an effective dose of an IAP, allows reducing a likelihood of onset of the side effects and reducing their length and/or severity. Also, a speed of recovery of a patient from the symptoms of the side effects can be increased.

The IAP, which can be administered orally, can be selected from human IAP or calf/bovine IAP. In some embodiments, the IAP comprises an amino acid sequence having at least about 60%, or at least about 65%, or at least about 70%, or at least about 75%, or at least about 80%, or at least about 85%, or at least about 90%, or at least about 95%, or at least about 96%, or at least about 97%, or at least about 98%, or at least about 99%, or at least about 100% identity with any one of SEQ ID NOs: 11-11, 17, 18, or 41. In some embodiments, the IAP comprises an amino acid sequence having at least about 60%, or at least about 65%, or at least about 70%, or at least about 75%, or at least about 80%, or at least about 85%, or at least about 90%, or at least about 95%, or at least about 96%, or at least about 97%, or at least about 98%, or at least about 99%, or at least about 100% identity with SEQ ID NO: 2. In some embodiments, the IAP comprises an amino acid sequence having at least 90% identity with SEQ ID NO: 2 or SEQ ID NO: 5 or SEQ ID NO: 41.

For example, in some embodiments, the methods in accordance with some embodiments of the present disclosure can prevent, reduce, or eliminate the side of the chemotherapeutic treatment, comprising diarrhea. In some embodiments, the Bristol stool scale is used to determine whether the stool from a subject administered with IAP is trending back to normal (e.g., a score of 3 or 4) from diarrhea (e.g., a score of 6 or 7). In various embodiments, the stool of a subject undergoing a chemotherapeutic treatment is scored as 6 or 7, according to the Bristol stool scale. In some embodiments, a subject undergoing a chemotherapeutic treatment and having been administered IAP has stool that is scored as 3 or 4 or 5, according to the Bristol stool scale.

The nucleoside analog can be any suitable nucleoside analog, including, without limitation, to 5-fluorouracil (5-FU), 5'-deoxyfluorouridine, 5-fluoro-2'-deoxyuridine triphosphate, fluorouridine, 2'-deoxyfluorouridine, fluorocytosine, trifluoro-methyl-2'-deoxyuridine, cytarabine, cyclocytidine, arabinosyl cytosine, 5-aza-2'-deoxycytidine, arabinosyl-5-azacytosine, 6-azacytidine, N-phosphono-acetyl-L-asparticacid, pyrazofurin, 6-azauridine, azaribine, thymidine, Fazarabine, and 3-deazauridine. In some embodiments, the nucleoside analog comprises at least one of fluoropyrimidine, 5-fluorouracil, 5-fluoro-2'-deoxycytidine, 5-fluoro-2'-deoxyuridine triphosphate, gemcitabine, troxacitabine, decitabine, cytarabine, pseudoisocytidine, Azacytidine, Decitabine, Zebularine, Ancitabine, Fazarabine, 6-azacytidine, capecitabine, N4-octadecyl-cytarabine, elaidic acid-cytarabine, cladribine, acyclovir, clofarabine, nelarabine, forodesine, 8-chloroadenosine, sapacitabine, thiarabine, and derivatives thereof. In at least some embodiments, the nucleoside analog is a pyrimidine analog such as 5-FU.

In some embodiments, the nucleoside analog is 5-fluorouracil (5-FU). In some embodiments, the standard 5-FU treatment regimen comprises administering about 12 mg/kg once daily for four successive days and optionally about 6 mg/kg on the sixth, eighth, tenth and twelfth days unless toxicity occurs. In various embodiments, administration of an IAP may allow a patient to be administered a full regimen without having to cease treatment because of side effects. In some embodiments, administration of an IAP allows a patient to be administered increased dosages (e.g. greater than about 20 mg/kg once daily, or about 18 mg/kg once daily, or about 16 mg/kg once daily, or about 14 mg/kg once daily, or about 12 mg/kg once daily) on greater than four (e.g. about 10, about 9, about 8, about 7, about 6, or about 5) successive days; greater than about 15 mg/kg once daily, or about 12 mg/kg once daily, or about 10 mg/kg once daily, or about 8 mg/kg once daily, or about 6 mg/kg once daily on the sixth, eighth, tenth and twelfth day; and/or length of administration (e.g. beyond 12 days, including, for example, about 13, about 14, about 15, about 16, about 17, about 18, about 19, about 20, about 21, about 22, about 23, about 24, about 4 weeks, or about one month).

In some embodiments, administration of an IAP may allow a patient to be administered a dose of 5-FU that exceeds about 200 mg daily, about 300 mg daily, about 400 mg daily, about 500 mg daily, about 600 mg daily, about 700 mg daily, or about 800 mg daily, or about 900 mg daily, or about 1000 mg daily.

The method of treating or preventing at least one side effect of a chemotherapeutic treatment with a nucleoside analog in a subject can be used in treatments of various cancers, including colorectal, breast, bowel, stomach, colon, anal, head and neck cancers, skin, oesophageal (gullet), and pancreatic cancer. The nucleoside analog can be (co)administered in combination of one or more of other nucleoside analogs or other therapeutic agents. For example, in some embodiments, the method further comprise administering one or more corticosteroids.

In some embodiments, the administration of the IAP allows reducing a dose, length, and/or frequency of administration of the nucleoside analog. In some embodiments, the reduced dose of the nucleoside analog can be a sub-therapeutic dose of the nucleoside analog. In some embodiments, the use of the IP allows increasing a therapeutic window of the nucleoside analog. The increased therapeutic window of the nucleoside analog may comprise one or more of increasing a subject's likelihood of receiving nucleoside analog maintenance therapy; increasing a subject's likelihood of receiving a complete regimen of the nucleoside analog; increasing a subject's likelihood of receiving more than a complete regimen of the nucleoside analog; and increasing a dose, length, and/or frequency of a nucleoside analog treatment.

In some embodiments, administering an effective amount of an IAP increases the ability of a cancer patient to receive a complete regimen of a combination therapy with 5-FU and not have to cease treatment because of, for example, side effects which are discussed in more detail below. In some embodiments, administering an effective amount of an IAP increases the ability of a cancer patient to receive a greater dose or longer duration of combination therapy with 5-FU. For example, a combination therapy regimen 5-fluorouracil/leucovorin may be (a) 6 week cycle with infusional 5-fluorouracil/leucovorin: 180 mg/m$^2$ IV infusion over 30-90 minutes once on days 1, 15, and 29 IV (infuse over 30-90 min), followed by infusion with leucovorin and 5-fluorouracil; next cycle begins on day 43 or (b) 6 week cycle with bolus 5-fluorouracil/leucovorin: 125 mg/m$^2$ on days 1, 8, 15, and 22 (infuse over 90 min), followed by bolus doses of leucovorin and 5-fluorouracil. In various embodiments, administering an effective amount of an IAP increases the dose and/or frequency of this regimen. For example, this regimen can be extended beyond 6 weeks to about 45, or about 50, or about 55, or about 60, or about 65, or about 70, or about 75, or about 100 days (including about 7, or about 8, or about 9, or about 10, or about 11, or about 12 weeks).

In some embodiments, administering an effective amount of an IAP increases the ability of a cancer patient to receive a complete regimen of any one of the FOLFOX, FOLFIRI, IFL, FL (Mayo), QUASAR, Machover schedule, CAF, CMF, ECF, and FEC regimens and not have to cease treatment because of side effects. In some embodiments, administering an effective amount of an IAP increases the ability of a cancer patient to receive a greater dose or longer duration of therapy in the FOLFOX, FOLFIRI, IFL, FL (Mayo), QUASAR, Machover schedule, CAF, CMF, ECF, and FEC regimens.

In some embodiments, the present methods pertain to prevention or reduction of reduced diversity in the gut microbiome, which may be a side effect or result of chemotherapuetic treatment. In some embodiments, the present methods relate to repairing and/or repopulating the gut microbiome of a subject after chemotherapuetic treatment.

In various embodiments, the present methods prevent, reduce or eliminate a side effect of chemotherapuetic treatment, including acute side effects, long-term side effects), or cumulative side effects. In various embodiments, the present methods reduce or eliminate a local or systemic side effect of chemotherapuetic treatment. In various embodiments, the side effect of chemotherapuetic treatment is one or more of diarrhea, colitis, mucositis, weight loss, pain, nausea, vomiting, constipation, anemia, malnutrition, alopecia, myelosuppression, renal toxicity, hair loss, numbness, changes in tastes, loss of appetite, thinned or brittle hair, mouth sores, memory loss, hemorrhage, cardiotoxicity, hepatotoxicity, ototoxicity, and post-chemotherapy cognitive impairment. The side effects can also include fatigue, damage to the epithelial surfaces infertility, fibrosis, epilation, dryness (e.g. without limitation, dry mouth (xerostomia) and dry eyes (xerophthalmia), and dryness of the armpit and vaginal mucosa), lymphedema, heart disease, cognitive decline, and vitamin B12 malabsorption.

In some embodiments, an IAP is administered in combination with an additional agent, which can be any of the agents described herein or another agent, including but not limited to a corticosteroid, an antioxidant (e.g., amifostine and vitamin E), a cytokine (e.g., a stem cell factor), etc.

In various embodiments, administration of an AP-based agent stimulates and protects stem cells. For example, the present invention and composition may stimulate and protect hematopoietic stem cells including various hematopoietic progenitor cells. In another example, the present methods and compositions may stimulate and protect gastrointestinal stem cells such epithelial cells (e.g., Goblet cells) and intestinal crypt stem cells. In some embodiments, the present methods and compositions protect small intestinal cells such as Goblet cells from hypoplasia and loss (e.g., apoptosis or necrosis). In various embodiments, methods and compositions of the present invention significantly enhance recovery of the GI system following chemotherapuetic treatment.

In various embodiments, the subject is a cancer patient. The cancer can comprise colon and rectum cancer; basal cell carcinoma, biliary tract cancer; bladder cancer; bone cancer; brain and central nervous system cancer; breast cancer; cancer of the peritoneum; cervical cancer; choriocarcinoma; connective tissue cancer; cancer of the digestive system; endometrial cancer; esophageal cancer; eye cancer; cancer of the head and neck; gastric cancer (including GI cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), or Meigs' syndrome.

Additional Therapeutic Agents and Combination Therapy

Administration of the present compositions and formulations comprising the AP-based agent may be combined with additional agents. Co-administration of the additional agent and the present compositions/formulations may be simultaneous, sequential, or combinations thereof. Further, the present compositions/formulations may comprise an additional agent (e.g., via co-formulation). For example, the additional agent and the AP-based agent may be combined into a single formulation. Alternatively, the additional agent and the AP-based agent may be formulated separately.

In one embodiment, the additional agent and the AP-based agent are administered to a subject simultaneously. The term "simultaneously" as used herein, means that the additional gent and the AP-based agent are administered with a time separation of no more than about 60 minutes, such as no more than about 30 minutes, no more than about 20 minutes, no more than about 10 minutes, no more than about 5 minutes, or no more than about 1 minute. Administration of the additional agent and the AP-based agent can be by simultaneous administration of a single formulation (e.g., a formulation comprising the additional agent and the alkaline phosphatase) or of separate formulations (e.g., a first formulation including the additional agent and a second formulation including the AP-based agent).

In a further embodiment, the additional agent and the AP-based agent are administered to a subject simultaneously but the release of the additional agent and the alkaline phosphatase from their respective dosage forms (or single unit dosage form if co-formulated) may occur sequentially.

Co-administration does not require the additional agent and the AP-based agent to be administered simultaneously, if the timing of their administration is such that the pharmacological activities of the additional agent and the AP-based agent overlap in time. For example, the additional agent and the AP-based agent can be administered sequentially. The term "sequentially" as used herein means that the additional agent and the AP-based agent are administered with a time separation of more than about 60 minutes. For example, the time between the sequential administration of the additional agent and the AP-based agent can be more than about 60 minutes, more than about 2 hours, more than about 5 hours, more than about 10 hours, more than about 1 day, more than about 2 days, more than about 3 days, or more than about 1 week apart. The administration times will depend on the rates of metabolism, excretion, and/or the pharmacodynamic activity of the additional agent and the AP-based agent being administered. Either the additional agent or the AP-based agent may be administered first.

Co-administration also does not require the additional agent and the AP-based agent to be administered to the subject by the same route of administration. Rather, each therapeutic agent can be administered by any appropriate route, for example, parenterally or non-parenterally.

In various embodiments, the additional agents include one or more of blood products, colony stimulating factors, cytokines and/or growth factors, antibiotics, diluting and/or blocking agents, mobilizing or chelating agents, stem cell transplants, and antioxidants or free radicals. Also, in embodiments in which a chemotherapy is used in combination with a radiation therapy, the additional agents include various radioprotectants.

In some embodiments, the blood product is one or more of hematopoietic growth factors, such as filgrastim (e.g. NEUPOGEN), a granulocyte colony-stimulating factor (G-CSF), which may be optionally pegylated (e.g. NEULASTA); sargramostim (LEUKINE); and a granulocyte-macrophage colony-stimulating factor (GM-CSF) and a KSF.

In some embodiments, the additional agent is one or more cytokines and/or growth factors that may confer cell protection by replenishing and/or protecting the stem cell populations. In some cases, stem cell factor (SCF, c-kit ligand), Flt-3 ligand, and/or interleukin-1 fragment IL-1b-rd may be used. Several factors, while not cytokines by nature, stimulate the proliferation of the immunocytes and may be used in combination with the AP-based agent. For example, 5-AED (5-androstenediol) is a steroid that stimulates the expression of cytokines and increases resistance to bacterial and viral infections. Synthetic compounds, such as ammonium tri-chloro(dioxoethylene-O,O'-) tellurate (AS-101), may also be used to induce secretion of numerous cytokines and for combination with the AP-based agent. Growth factors and cytokines may also be used to provide protection against the gastrointestinal syndrome. Keratinocyte growth factor (KGF) promotes proliferation and differentiation in the intestinal mucosa, and increases the post-irradiation cell survival in the intestinal crypts. Hematopoietic cytokine SCF may also increase intestinal stem cell survival and associated short-term organism survival.

In certain embodiments, the AP-based agent may be added to a regimen of cytokines (e.g. for FILGRASTIM (G-CSF) 2.5-5 µg/kg/d QD s.c. (100-200 µg/m$^2$/d); for SARGRAMOSTIM (GM-CSF) 5-10 µg/kg/d QD s.c. (200-400 µg/m$^2$/d); and/or for PEGFILGRASTIM (pegG-CSF) 6 mg once s.c.).

In some embodiments, the additional agent is an interleukin, such as IL-12 (e.g., HEMAMAX (NEUMEDICINES, INC.)).

In some embodiments, the antibiotic is one or more of an anti-bacterial (anti-gram positive and anti-gram negative agents), and/or anti-fungal, and/or anti-viral agent. By way of non-limiting example, in some embodiments, the antibiotic may be a quinolone, e.g. ciprofloxacin, levofloxacin, a third- or fourth-generation cephalosporin with pseudomonal coverage: e.g., cefepime, ceftazidime, or an aminoglycoside: e.g. gentamicin, amikacin, penicillin or amoxicillin, acyclovir, vanomycin. In various embodiments, the antibiotic targets *Pseudomonas aeruginosa*.

In some embodiments, the additional agent is a stem cell transplant (e.g. bone marrow transplant, PBSCT, MSCT). In some embodiments, the stem cell transplant is Remestemcel-L (Osiris) of CLT-008 (Cellerant).

In some embodiments, the additional agent is an antioxidant or free radical. Antioxidants and free radical scavengers that may be used in the practice of the invention include, but are not limited to, thiols, such as cysteine, cysteamine, glutathione and bilirubin; amifostine (WR-2721); vitamin A; vitamin C; vitamin E; and flavonoids such as Indian holy basil (*Ocimum sanctum*), orientin and vicenin.

In some embodiments, the additional agent may be a steroid (e.g. 5-androstenediol), an antioxidant (e.g., amifostine and vitamin E, gamma tocotrienol (a vitamin-E moiety), and genistein (a soy byproduct)), a cytokine (e.g., a stem cell factor), a growth factor (e.g., keratinocyte growth factor), ammonium trichloro(dioxoethylene-O,O')tellurate, anti-nausea agents, anti-diarrhea agents, antiemetics ((e.g. oral prophylactic antiemetics) such as granisetron (KYTRIL), ondansetron (ZOFRAN), and 5-HT3 blockers with or without dexamethasone), analgesics, anxiolytics, sedatives, cytokine therapy, and antibiotics.

Further examples of combination agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; def of amine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50%" covers the range of 45% to 55%.

An "effective amount," when used in connection with medical uses is an amount that is effective for providing a measurable treatment, prevention, or reduction in the rate of pathogenesis of a disorder of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

In some embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

The amount of compositions described herein needed for achieving a therapeutic effect may be determined empirically in accordance with conventional procedures for the particular purpose. Generally, for administering therapeutic agents (e.g., microbiome-modulating agents and/or additional therapeutic agents described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures, tissue samples, tissue homogenates or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays or measurements or methane production in stool samples. Also, a dose can be formulated in animal models to achieve a circulating plasma concentration range that includes the 1050 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EXAMPLES

Example 1: IAP Reduces Side Effects of 5-FU

Experiments were performed in order to assess the effect of IAP treatment on diarrhea and weight change side effects of using a chemotherapeutic agent comprising a nucleoside analog for treating cancer.

The study conducted included evaluation of the effects of administration of an IAP ("SYN-020" is synonymous with IAP and SYN BIAPII) along with a chemotherapeutic treatment with 5-fluorouracil (5-FU) in a murine model. Taken together, FIGS. 1A-1B and 2A-2C illustrate, based on assessment of mice weight change and stool consistency, that administration of IAP reduces side effects of 5-FU. Stool consistency was scored as the following: Score 0=Normal (no diarrhea); Score 2=Loose, formed stools; and Score 4=Diarrhea.

The first set of experiments included three groups of BALB/c mice inoculated with CT26 murine colorectal cancer cells into the right flank: (1) a no-treatment control group of 18 male mice ("untreated"); (2) a group of 18 male mice ("vehicle+5-FU") that received an intraperitoneal (IP) QD (once daily) dose of 30 mg/kg of 5-FU for 5 consecutive days (days 0-4) and a vehicle was administered PO (orally) BID (twice a day) throughout the study (days −3 to +26); and (3) a group of 18 male mice ("SYN BIAPII+5-FU") that received an IP QD dose of 30 mg/kg of 5-FU for 5 consecutive days (days 0-4) and an IAP (SYN-020) in a dose of 0.5 mg/kg, administered PO BID throughout the study (days −3 to +26).

Figure 1B:
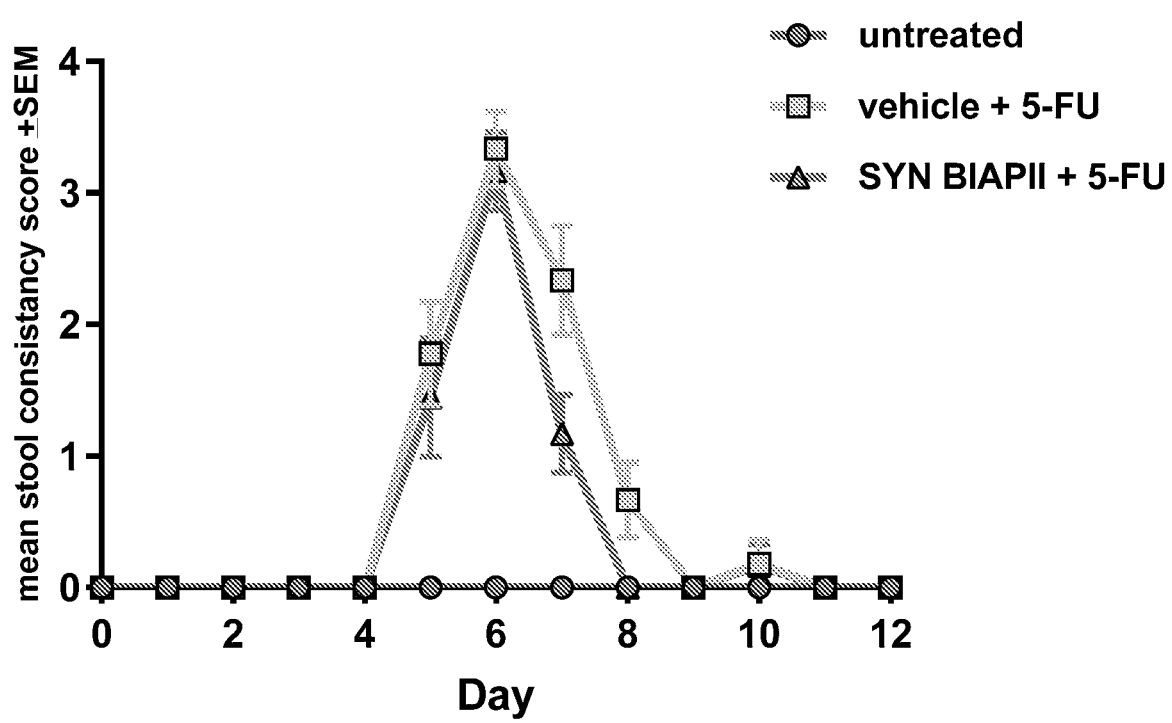

FIG. 1A shows mean percent of weight change±SEM for untreated (top curve), vehicle+5-FU (middle curve), and SYN BIAPII+5-FU (bottom curve) mice versus a number of days of the study. FIG. 1B shows assessment of stool consistency, as a mean stool consistency score±SEM versus a number of days, of vehicle+5-FU and SYN BIAPII+5-FU mice relative to untreated mice data for which is shown as a baseline at the x-axis). As shown, the administration of 5-FU caused loose stools/diarrhea, as well as associated weight loss, in all of the treated animals. These symptoms peaked at day 6 in both of the vehicle+5-FU and SYN BIAPII+5-FU mice groups, and recovered by day 9. The administration of the IAP in the SYN BIAPII+5-FU group shows a significantly faster recovery from the loose stools/diarrhea symptoms and associated weight loss ($p<0.03$).

The second set of experiments included four groups of BALB/c mice inoculated with CT26 murine colorectal cancer cells into the right flank: (1) a vehicle control group of 30 male mice ("vehicle"); (2) a group of 30 male mice that received a daily treatment dose of 100 U/dose, 0.5 mg/kg of SYN BIAP II alone ("SYN BIAP II"); (3) a group of 30 male mice ("vehicle+5-FU") that received an IP QD dose of 30 mg/kg of 5-FU for 5 consecutive days (days 0-4) and vehicle treatment; and (4) a group of 30 male mice ("SYN BIAPII+5-FU") that received an IP QD dose of 30 mg/kg of 5-FU for 5 consecutive days (days 0-4) and an IAP (SYN-020) in a dose of 100 U/dose, 0.5 mg/kg, administered PO BID throughout the study (days −3 to +26).

Figure 2A:
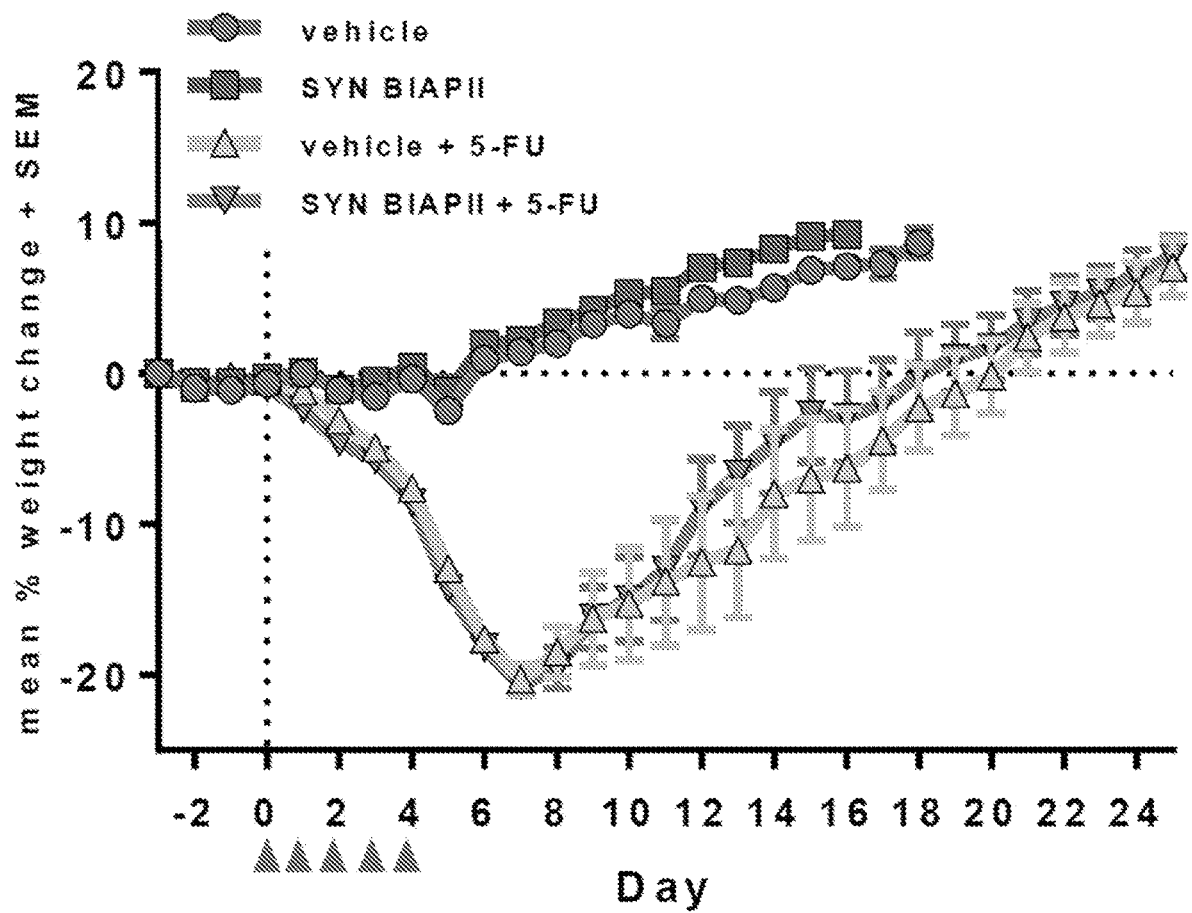
FIGS. 2A, 2B, and 2C further illustrate that administration of IAP reduces side effects of 5-FU.

FIG. 2A depicts the mean daily body weight through 50% group survival, which is displayed as percent change over time compared to body weight at Day 0+SEM. Animals administered vehicle+5-FU over Days 0-4 displayed chemotherapy-induced weight loss that peaked at about (−20%) on Day 7, after which animals regained lost weight by about Day 20. The mean percentage of weight change of animals administered SYN BIAPII+5-FU is not significantly different from that of animals administered vehicle+5-FU. Cumulative differences in body weight change between treatment groups through 50% common group survival (Day (−3)-16) were assessed by calculating the area under the curve (AUC) for each animal using the trapezoidal transformation.

Figure 2B:
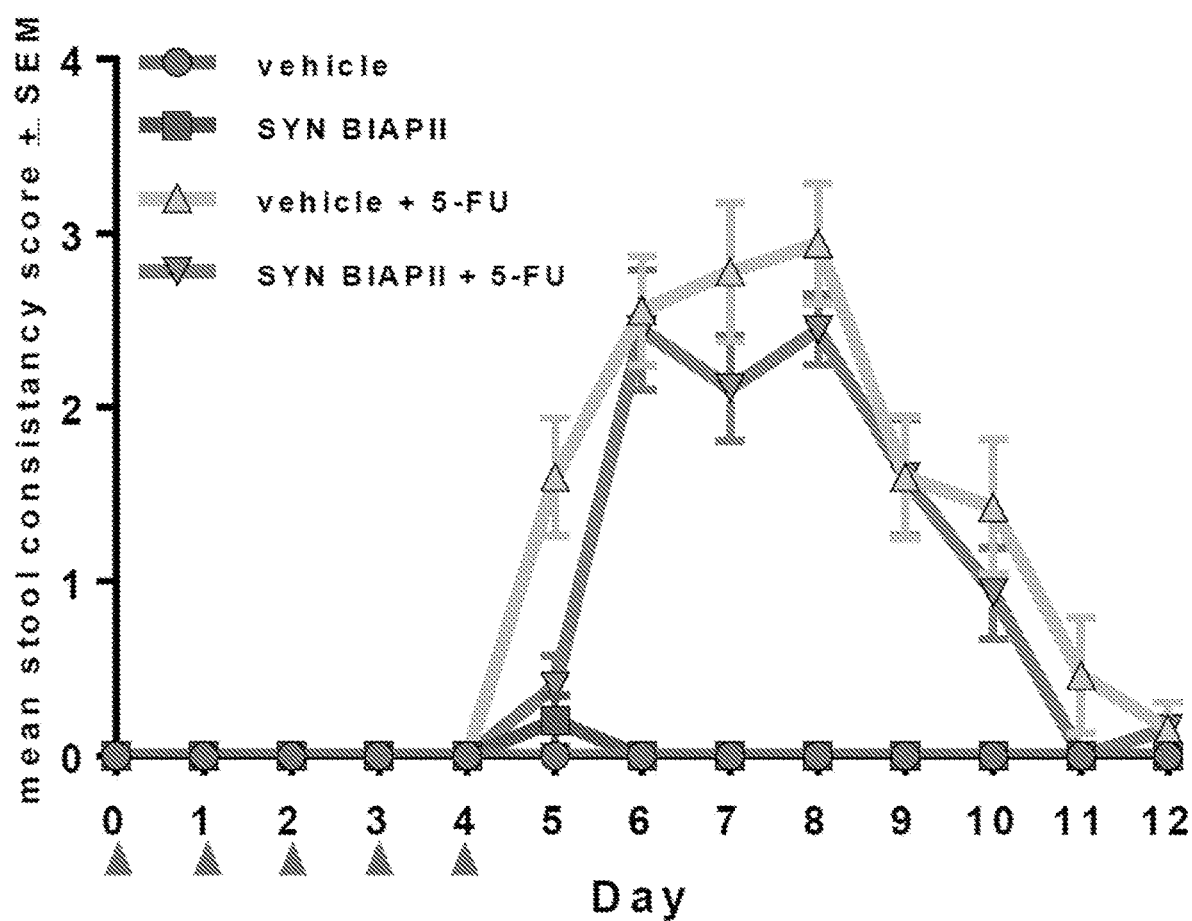

FIG. 2B shows the results of Stool Consistency Scoring daily over Days 0-12; mean scores+SEM are shown. Arrows indicate 5-FU administration days. Animals treated with vehicle or SYN BIAPII alone generally displayed normal stool consistency throughout the course of the analysis. For animals administered vehicle+5-FU or SYN BIAPII+5-FU, incidence of loose stools or diarrhea was first observed on Day 5. For animals administered vehicle+5-FU, incidence of loose stools generally resolved by Day 12; for animals administered SYN BIAPII+5-FU, incidence of loose stools generally resolved by Day 11. Compared to treatment with vehicle+5-FU, an improvement in overall stool score was observed for animals treated with SYN BIAPII+5-FU over days 5-11. The statistical significance of group differences in daily stool scores was assessed on each day by Mann-Whitney rank-sum analysis. Compared to treatment with vehicle+5-FU, animals treated with SYN BIAPII+5-FU showed a statistically significant improvement in overall stool score on Day 5 ($p=0.006$).

Table 1 below compares the duration of 5-FU-induced diarrhea by calculating the percentage of total animal-days with diarrhea (score=4). Groups were compared by chi-square test. Compared to untreated animals, a statistically significant cumulative increase in animal-days with diarrhea was observed both for animals treated with vehicle+5-FU ($p=<0.0001$) and for those treated with SYN BIAPII+5-FU ($p=<0.0001$). Compared to animals treated with vehicle+5-FU, animals treated with SYN BIAPII+5-FU displayed a statistically significant improvement in overall duration of diarrhea ($p=0.0006$).

TABLE 1

Comparison of Duration of Diarrhea amoung Groups 1-4
Duration of Diarrhea (score = 4)

| Group | Treatment | Days = 4 | Days < 4 | Total Animal Days | % Days = 4 | Chi-Sq. vs. Group 1; df | p value vs. Group 1 | Chi-Sq. vs. Group 3 | p value vs. Group 3 |
|---|---|---|---|---|---|---|---|---|---|
| 1 | vehicle | 0 | 306 | 306 | 0 | — | — | — | — |
| 2 | SYN BIAPII | 1 | 299 | 300 | 0.33% | 1.022; 1 | 0.312 | — | — |
| 3 | vehicle + 5-FU | 43 | 245 | 288 | 14.93% | 49.25; 1 | <0.0001**** | — | — |
| 4 | SYN BIAPII + 5-FU | 18 | 273 | 291 | 6.19% | 19.52; 1 | <0.0001**** | 11.74; 1 | 0.0006*** |

Figure 2C:
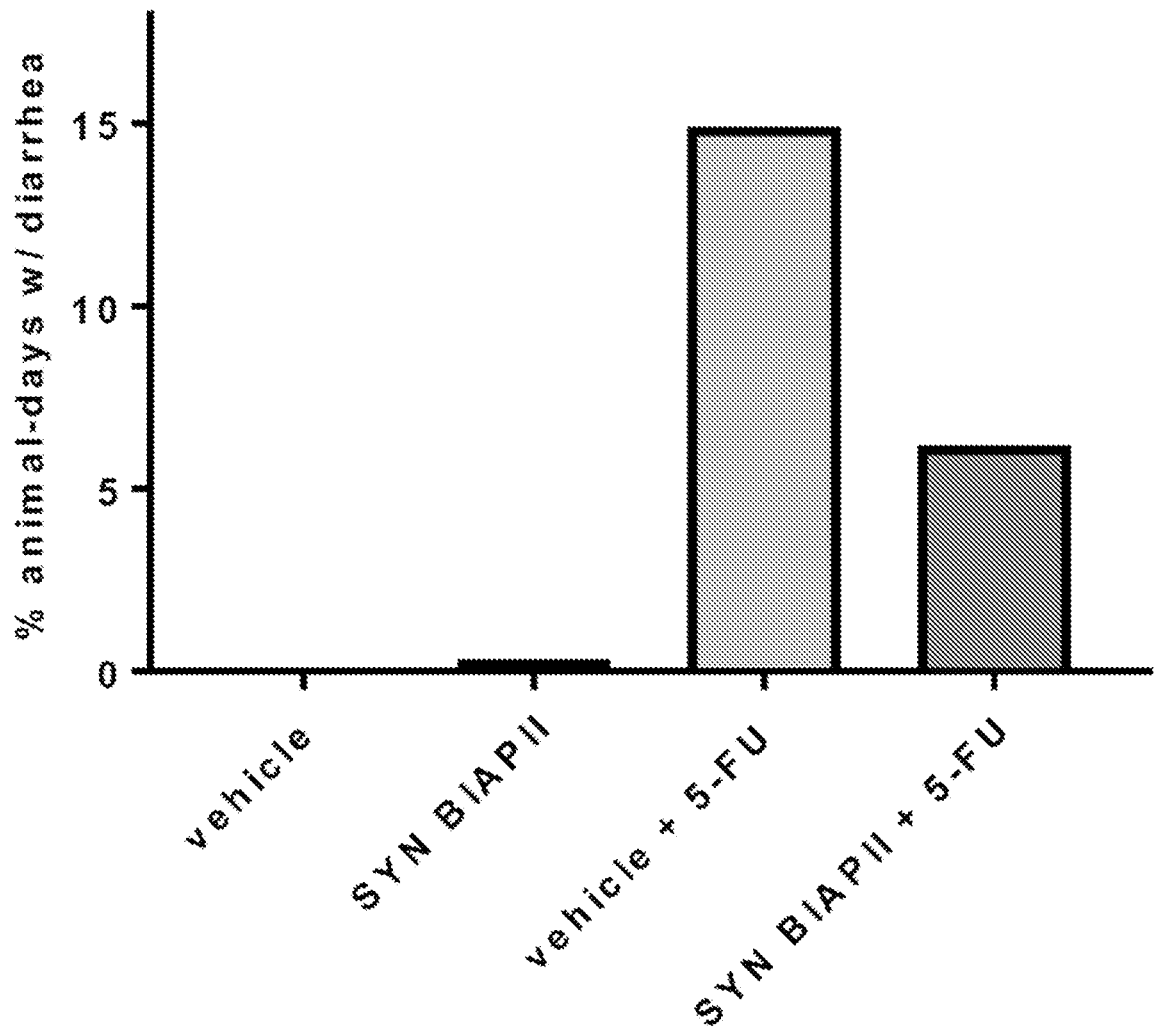

Finally, FIG. 2C depicts a graphical representation of the percentage of total animal-days with diarrhea by treatment group.

Accordingly, the present studies demonstrate that administration of IAP improves side effects associated with 5-FU, such as, e.g., diarrhea and mucositis. Accordingly, IAP can be utilized as a therapeutic agent for use in treatment, prevention, and mitigation of cancer treatment-related side effects and to enhance the overall response of chemotherapeutic agents.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

The invention claimed is:

1. A method of treating or preventing at least one side effect of a chemotherapeutic treatment with a nucleoside analog in a subject, comprising administering to the subject a pharmaceutical composition comprising an intestinal alkaline phosphatase (IAP), wherein the subject has undergone or is undergoing a treatment of a cancer using the chemotherapeutic treatment, wherein the amino acid sequence of the IAP consists of the sequence of SEQ ID NO: 41, and wherein the side effect of the chemotherapeutic treatment is mucositis.

2. The method of claim 1, wherein the pharmaceutical composition is administered sequentially with the chemotherapeutic treatment.

3. The method of claim 1, wherein the pharmaceutical composition is administered simultaneously with the chemotherapeutic treatment.

4. The method of claim 1, wherein the pharmaceutical composition is administered intermittently with the chemotherapeutic treatment.

5. The method of claim 1, wherein the pharmaceutical composition is administered orally.

6. The method of claim 1, wherein the pharmaceutical composition is formulated for gastrointestinal (GI) release.

7. The method of claim 1, wherein the nucleoside analog is a purine or pyrimidine analog or derivatives thereof.

8. The method of claim 7, wherein the pyrimidine analog comprises at least one of 5-fluorouracil, 5'-deoxyfluorouridine, 5-fluoro-2'-deoxyuridine triphosphate, fluorouridine, 2'-deoxyfluorouridine, fluorocytosine, trifluoro-methyl-2'-deoxyuridine, cytarabine, cyclocytidine, arabinosyl cytosine, 5-aza-2'-deoxycytidine, arabinosyl-5-azacytosine, 6-azacytidine, N-phosphonoacetyl-L-asparticacid, pyrazofurin, 6-azauridine, azaribine, thymidine, Fazarabine, 3-deazauridine, and derivatives thereof.

9. The method of claim 1, wherein the nucleoside analog comprises at least one of fluoropyrimidine, 5-fluorouracil, 5-fluoro-2'-deoxycytidine, 5-fluoro-2'-deoxyuridine triphosphate, gemcitabine, troxacitabine, decitabine, cytarabine, pseudoisocytidine, Azacytidine, Decitabine, Zebularine, Ancitabine, Fazarabine, 6-azacytidine, capecitabine, N4-octadecyl-cytarabine, elaidic acid-cytarabine, cladribine, acyclovir, clofarabine, nelarabine, forodesine, 8-chloroadenosine, sapacitabine, thiarabine, and derivatives thereof.

10. The method of claim 1, wherein the administration of the pharmaceutical composition allows reducing a dose, length, and/or frequency of administration of the nucleoside analog.

11. The method of claim 1, wherein the method increases a therapeutic window of the nucleoside analog.

12. The method of claim 1, wherein the IAP does not hinder the treatment of the cancer in the subject.

13. The method of claim 1, wherein the chemotherapeutic treatment is 5-fluorouracil.

* * * * *